US007560226B2

(12) United States Patent
Christopherson et al.

(10) Patent No.: US 7,560,226 B2
(45) Date of Patent: Jul. 14, 2009

(54) ASSAY TO DETECT A BINDING PARTNER

(75) Inventors: Richard Ian Christopherson, Sydney (AU); Cristobal Guillermo Dos Remedios, Sydney (AU)

(73) Assignee: Medsaic Pty Limited, New South Wales (AU)

( * ) Notice: Subject to any disclaimer, the term of this patent is extended or adjusted under 35 U.S.C. 154(b) by 0 days.

(21) Appl. No.: 09/888,959

(22) Filed: Jun. 25, 2001

(65) Prior Publication Data

US 2002/0019018 A1 Feb. 14, 2002

Related U.S. Application Data

(63) Continuation of application No. 09/869,229, filed as application No. PCT/AU99/01156 on Dec. 23, 1999.

(30) Foreign Application Priority Data

Dec. 23, 1998 (AU) .......................... PP7916
May 18, 1999 (AU) .......................... PQ0425

(51) Int. Cl.
*G01N 33/48* (2006.01)
*G01N 33/574* (2006.01)
(52) U.S. Cl. .................... 435/4; 435/7.23; 435/7.24; 436/64
(58) Field of Classification Search .............. 435/4, 435/7.1, 7.2, 7.21, 7.23, 7.24, 7.92; 436/518, 436/524, 527, 528, 529, 530, 532, 63, 64, 436/534, 531
See application file for complete search history.

(56) References Cited

U.S. PATENT DOCUMENTS

| 4,591,570 | A |   | 5/1986  | Chang                      |
|-----------|---|---|---------|----------------------------|
| 4,797,356 | A |   | 1/1989  | Brandt et al.              |
| 5,059,522 | A |   | 10/1991 | Wayne                      |
| 5,234,816 | A | * | 8/1993  | Terstappen                 |
| 5,384,263 | A |   | 1/1995  | Kauvar                     |
| 5,514,558 | A |   | 5/1996  | Ceriani et al.             |
| 5,538,855 | A |   | 7/1996  | Orfao de Matos Correira E. Vale |
| 5,597,735 | A |   | 1/1997  | Laszlo et al.              |
| 5,674,739 | A | * | 10/1997 | Shyjan ............ 435/252.3 |
| 5,726,064 | A |   | 3/1998  | Robinson et al.            |
| 5,968,513 | A |   | 10/1999 | Gallo et al.               |
| 6,087,102 | A |   | 7/2000  | Chenchik et al.            |
| 6,265,150 | B1| * | 7/2001  | Terstappen et al. ...... 435/5 |

FOREIGN PATENT DOCUMENTS

| WO | WO 89/10977 |   | 11/1989 |
|----|-------------|---|---------|
| WO | WO 95/05604 |   | 2/1995  |
| WO | WO95/06909  | * | 3/1995  |
| WO | WO 97/10365 |   | 3/1997  |
| WO | WO 98/08083 |   | 2/1998  |
| WO | WO 99/40434 |   | 8/1999  |

OTHER PUBLICATIONS

Kurec,A.S. et al, British Journal of Haematology, 81: 45-51, 1992.*
Matutes, E. et al, Blood, 83(6): 1558-1562, 1994.*
Morreau, E.J. et al, Am. J. Clin. Pathol. 108: 378-382, 1997.*
Robbins, B.A. et al. Blood, 82(4): 1277-1287, 1993.*
Valet, G.K. et al., Cytometry 30(6): 275-288, 1997.*
Dictionary of Immunology, Third Edition, 1985, W.J. Herbert et al, Ed.s, p. 199.*
Wrightman et al, Blood. 1987, vol. 69, pp. 919-923.*
Abstract of Chang et al, J Pediatr Hematol Oncol. 2003, vol. 25, pp. 735-739.*
Buckland et al, Pathology. Aug. 2001 vol. 33, pp. 386-389.*
Becton Dickenson Acute Leukemia Phenotyping Kit, 1992, pp. 1-57.*
Sundberg et al (Journal of the American Chemical Society, 1995, vol. 117, pp. 12050-12057).*
Paul (Fundamental Immunology, (text) 1993, p. 460).*
Paul (Fundamental Immunology, Third Edition, 1993, p. 107).*
Mauro et al, (Curr Opin Oncol. Jan. 2001;13(1):3-7).*
Abstract of Kolialexi et al, Anticancer Res. Jul.-Aug. 1998;18(4A):2359-64.*
Abstract of Dorak et al (Leuk Lymphoma. Jan. 1994;12(3-4):211-22.*
Bortin et al (Blood. Jul. 1987;70(1):227-32).*
Haas et al (Nature. Oct. 1, 1992;359(6394):414-6).*
Abstract of Wang et al, Am J Hematology, Nov. 1995, 50(3):188-199).*
Lanza et al (European Journal of Histochemistry, 1996, vol. 40 suppl. 1, pp. 7-14).*
Ruiz-Arguelles et al (Cytometry, 1998, vol. 34, pp. 39-42).*
Stewart et al (Cytometry, 1997, vol. 30, pp. 231-235).*
Abstract of Gruber et al (Journal of Immunological Methods, 1993, vol. 163, pp. 173-179).*
Delamarche et al (Science, 1997, vol. 276, pp. 779-781).*
Belov, L., et al., "Immunophenotyping of Leukemias Using a Cluster of Differentiation Antibody Microarray," *Cancer Res.*, 61(11):4483-9, Jun. 1, 2000.
DiGiuseppe, J., et al., "Clinical Utility of Flow Cytometry in the Chronic Lymphoid Leukemias," *Semin Oncol.*, 25(1):6-10, Feb. 1998.

(Continued)

*Primary Examiner*—Karen A Canella
(74) *Attorney, Agent, or Firm*—Nixon Peabody, LLP

(57) ABSTRACT

A method can identify a type of leukemia in a human subject. A biological sample from the human subject that contains CD antigens is obtained. The sample is contacted with an array of immunoglobulin molecules. Each immunoglobulin in the array, with the exception of one or more negative controls, is capable of interaction with a CD antigen on one or more types of leukemia cells. The pattern of interaction between the immunoglobulin molecules and the CD antigens in said sample is then determined, thereby providing an immunophenotype of the cells which is characteristic of the type of leukemia.

14 Claims, 24 Drawing Sheets

OTHER PUBLICATIONS

Ekins, R., "Ligand Assays: From Electrophoresis to Miniaturized Microarrays," *Clin Chem.*, 44(9):2015-30, Sep. 1998.

Khalidi, H., et al., "The Immunophenotype of Adult Acute Myeloid Leukemia: High Frequency of Lymphoid Antigen Expression and Comparison of Immunophenotype, French-American-British Classification, and Karyotypic Abnormalities," *Am J Clin Pathol.*, 109(2):211-20, Feb. 1998.

Martin, B., et al., "Direct Protein Microarray Fabrication Using a Hydrogel Stamper," *Langmuir*, 14(15):3971-3975, Jul. 1998.

Mooney, J., et al., "Patterning of Functional Antibodies and Other Proteins by Photolithography of Silane Monolayers," *Proc Natl Acad Sci U S A.*, 93(22):12287-91, Oct. 29, 1996.

Piedras, J., et al., "Cellular Immunophenotypes in 97 Adults with Acute Leukemia," *Rev Invest Clin.*, 49(6):457-64, Nov.-Dec. 1997. Spanish.

Schmetzer, H., et al., "Immunological Classification of Chronic Myeloid Leukemia Distinguishes Chronic Phase, Imminent Blastic Transformation, and Acute Lymphoblastic Leukemia," *Exp Hematol.*, 25(6):502-8, Jun. 1997.

Silzel, J., et al., "Mass-sensing, Multianalyte Microarray Immunoassay with Imaging Detection," *Clin Chem.*, 44(9):2036-43, Sep. 1998.

Chang, et al., "Binding of Cells to Matrixes of Distinct Antibodies Coated on Solid Surface" *J. Of Immunological Methods* 65:217-223(1983).

Cooper, *The Cancer Book* 158-167 (1993).

Goward et al., "Expression and purification of a truncated recombinant streptococcal Protein G" *Biochem* 267:171-177(1990).

Mage et al, "Mouse Lymphocytes with and without surface immunoglobulin: preparative scale separation in polystyrene tissue culture dishes coated with specifically purified anti-immunoglobulin" *Journal of Immunological Methods* 15:47-56 (1977).

Mendoza et al.,"High-Throughput Microarray-Based Enzyme-Linked Immunisirbent Assay(ELISA)" *BioTechniques* 27:778-788 (Oct. 1999).

van Dongen et al., "Immunophenotyping of leukaemias and non-Hodgkin's lymphomas. Immunological markers and their CD codes" *Netherlands Journal of Medicine* 33:298-314 (1988).

Wysocki and Sato "Planning for lymphocytes: A method for cell selection" *Proc. Natl. Sci USA* 75(6):2844-2848 (1978).

\* cited by examiner

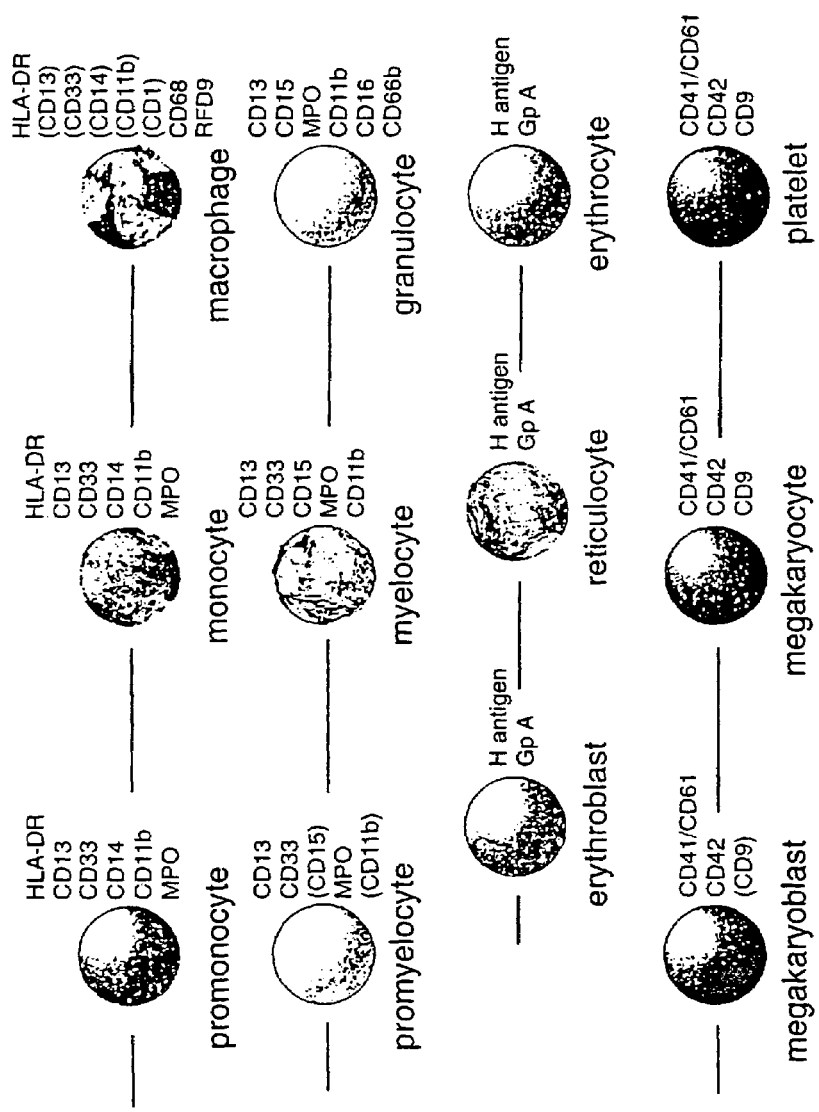
Figure 2 (ii)

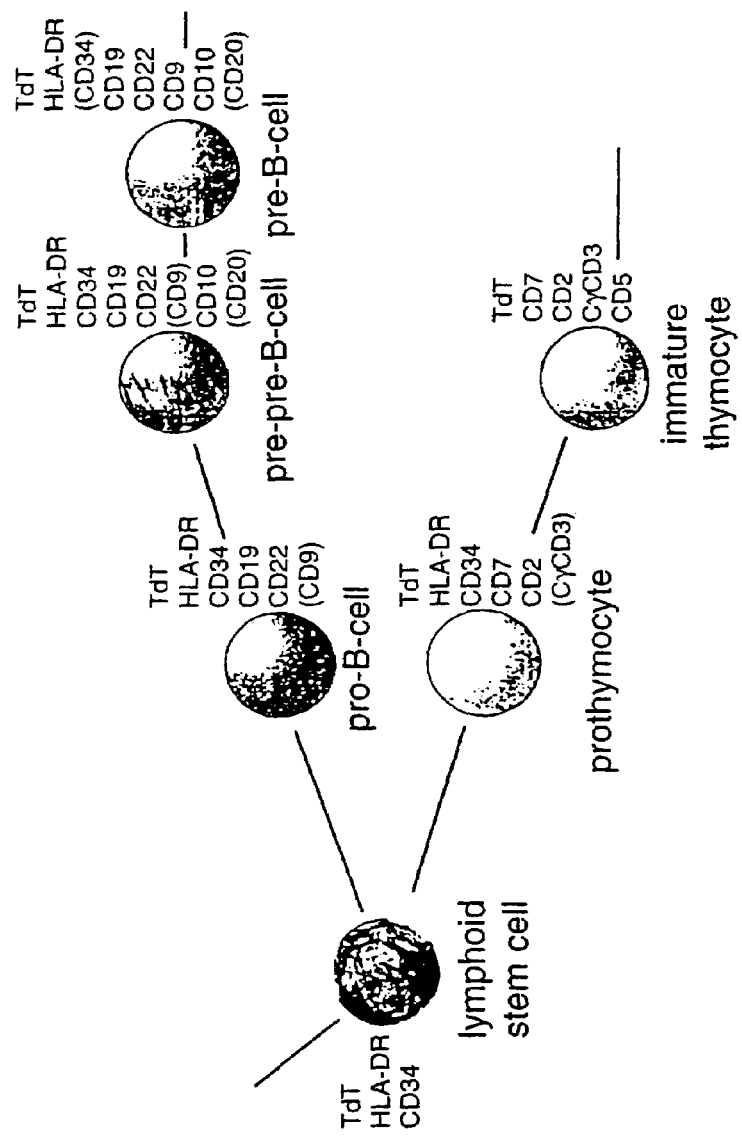
Figure 2 (iii)

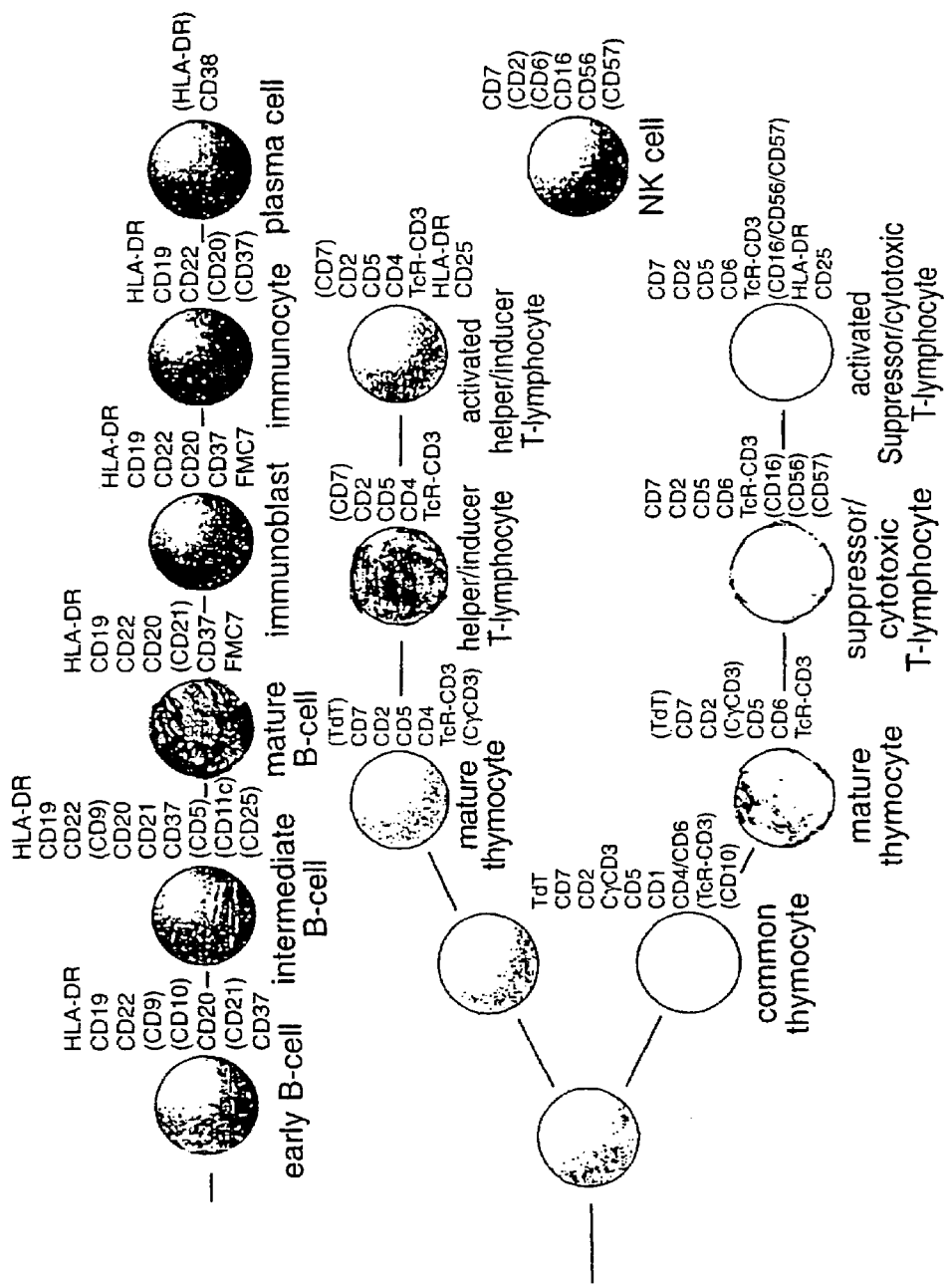
Figure 2 (iv)

Flow diagram for the antibody array procedure

CEM CELL ARRAY: T-cell ALL
Nomarski images

CD3 antibody dot binding a low number of CD3+ cells.

The distinct boundary of a CD4 antibody dot binding CD4+ cells.

CD8 antibody dot binding a low number of CD8+ cells.

CD14 antibody dot is negative.

CD19 antibody dot is negative.

CD56 antibody dot is negative.

*mag. x 20*

RAJI CELL ARRAY: B-cell Burkitt's Lymphoma
Nomarski images

CD3 antibody dot is negative.

CD4 antibody dot is negative.

CD8 antibody dot is negative.

CD14 antibody dot is negative.

CD19 antibody dot binding CD19+ cells.

CD56 antibody dot is negative.

*mag. x 20*

CCRF-CEM cells bound to a CD4 antibody dot and labelled with Alexa-488nm conjugated CD45 antibody.

| | | | | | |
|---|---|---|---|---|---|
| mIgG1 | 2 | 3 | 4 | 5 | 7 |
| 8 | 9 | 10 | 11b | 11c | 13 |
| 14 | 15 | 16 | 19 | 20 | 21 |
| 22 | 23 | 24 | 25 | 33 | 34 |
| 36 | 37 | 38 | 41 | 42a | 44 |
| 44 v3-10 | 44 v6 | 45 | 45 RA | 45 RO | 52 |
| 56 | 57 | 60 | 61 | 71 | 79a |
| 95 | 103 | 117 | 122 | 154 | GPA |
| HLA | KOR | FMC7 | mIgG2a | mIg2b | mIgM |

Figure 7a

| mIgG1 | 2 | 3 | 4 | 5 | 7 |
|---|---|---|---|---|---|
| 8 | 9 | 10 | 11b | 11c | 13 |
| 14 | 15 | 16 | 19 | 20 | 21 |
| 22 | 23 | 24 | 25 | 33 | 34 |
| 36 | 37 | 38 | 41 | 42a | 44 |
| 44 v3-10 | 44 v6 | 45 | 45 RA | 45 RO | 52 |
| 56 | 57 | 60 | 61 | 64 | 71 |
| 79a | 79b | 80 | 95 | 103 | 117 |
| 122 | 134 | 138 | 154 | Kappa | Lambda |
| GPA | HLA | KOR | FMC7 | Anti-Ig | IgG2a |

Figure 8a

ASSAY TO DETECT A BINDING PARTNER

RELATED APPLICATIONS

This application is a Continuation of U.S. application Ser. No. 09/869,229, filed Jun. 25, 2001, which is the U.S. National Phase under 35 U.S.C. §371 of International application PCT/AU99/01156, filed Dec. 23, 1999, which claims priority of Australian application AU/PQ0425/99, filed May 18, 1999, all of which are herein incorporated by reference.

FIELD OF THE INVENTION

The present invention relates generally to an assay to detect a binding partner. The presence or absence of a binding partner can be used to indicate a normal condition or a disease condition or disorder or a propensity for a disease condition or disorder to develop or the presence of a particular cell type, or microbial, viral, parasitic or other pathogenic agent in an animal, avian species or plant or the presence of a particular chemical entity in a sample such as a chemical library, biological specimen or environmental sample or phage display library. In one embodiment, the present invention provides an array of molecules having a binding partner in a biological sample from or derived from said animal, avian species or plant wherein the pattern of binding of the binding partners to the respective molecules on the array including the absence of binding or the density of partner interaction provides an indication of a normal condition or disease condition or disorder or a propensity for a disease condition or disorder to develop or the presence of a particular cell type or microbial, viral, parasitic or other pathogenic agent. In another embodiment, the binding partner is in a chemical, environmental or phage display library sample and the pattern of binding including absence of binding or the density of partner interaction is indicative of the presence, type and/or concentration of a particular binding partner or family of binding partners. The assay of the present invention is useful inter alia for the detection of cancers and neoplasias as well as non-neoplastic disorders in animals, including humans, as well as in avian species and plants. The assay is also useful for detecting cell types, microbial, viral, parasitic or other pathogenic agents and chemical entities in chemical, environmental and phage display samples. In a preferred embodiment, the molecules of the array comprise immunoglobulins capable of interaction with particular soluble, cell bound or synthetic antigens. The pattern of binding in the array including the presence, absence or amount of binding to the respective antigens provides an indication of the expression of antigens on or by cells which in turn provides an indication of a normal condition or disease condition or disorder such as cancer in an animal, avian species or plant. The pattern of binding also provides an indication of the presence and/or concentration of antigens in a chemical library, in an environmental sample or phage display library. In another embodiment, the molecules on the array are genetic molecules and are used to identify corresponding genetic material in particular cells.

BACKGROUND OF THE INVENTION

Bibliographic details of the publications referred to by the author, in this specification are collected at the end of the description.

The increasing sophistication of immunological techniques is greatly facilitating research and development in the medical, veterinary, horticultural and environmental fields. Of fundamental importance is the specificity of the antibody-antigen interaction. Through this interaction, the expression of genes encoding particular antigens can be determined.

Many disease states in avian species, plants and in particular animals, such as humans, have a genetic basis and can be characterised by changes in the patterns and/or levels of expression of various genes. For example, some cancers are associated with changes in the expression of oncogenes and tumor suppressor genes. Furthermore, disease conditions or disorders associated with changes in the cell cycle and development can be attributed to changes in transcriptional regulation of particular genes.

Although there are a number of genetic assays available to assess mutations, the identification of certain genetic changes cannot always be directly indicative of a disease condition or disorder.

Some genetic changes are expressed by alterations in cell surface antigens. Again, however, prior attempts to develop a diagnostic assay for complex disease conditions or disorders such as cancer based on the identification of a single antigen have not been universally successful.

Leukemias and lymphomas cause significant mortality and morbidity in humans. Such cancers result from the continuous proliferation of cells which would otherwise be blocked at various stages of normal differentiation to specialised cell types. Leukemias arise from blood forming cells in the bone marrow due to mutations in any of the precursors in the various lineages of differentiation (see FIG. 1). Lymphomas develop from lymphocytes or macrophages in lymphatic tissue.

Lymphocytes in the peripheral blood express a large number of different antigens on their outer plasma membranes many of which are receptors for growth factors, cell-cell interactions and immunoglobulins; molecules for cell adhesion or complement stimulation; enzymes and ion channels. A single systematic nomenclature has been developed to classify monoclonal antibodies against human leukocyte cell surface antigens known as the cluster of differentiation (CD) antigens (Kishimoto et al., 1997). Detailed information on CD antigens can be found at the website of the National Centre for Biotechnology Information (NCBI), a division of the National Library of Medicine (HLM) at the National Institutes of Health (NIH). The expression of these cell-surface antigens can distinguish different types of mature blood cells found in the peripheral circulation.

Cells in the peripheral blood are produced in the bone marrow by proliferation and differentiation down specific lineages from precursor myeloid or lymphoid stem cells which express the surface antigen CD34 (see FIG. 2).

Currently, a leukemia is diagnosed on the basis of morphology, expression of specific CD, lymphoid (LY) and myeloid (MY) antigens, enzyme activities and cytogenetic abnormalities, such as chromosome translocations. Diagnosis of acute myeloid leukemia (AML) is, for example, made using these four criteria. The expression of up to three CD antigens on leukemia cells is currently determined using fluorescently labelled antibodies against particular CD antigens with analysis by flow cytometry. Thus, screening leukemia cells from patients for expression of the 166 CD antigens is not practical using this labour intensive technique. Recently, de Matos and Vale (1996) developed a flow cytometric procedure for the simultaneous quantification in a single measurement, of the major types of human lymphocytes and their sub-sets. In this procedure, mixed populations of human lymphocytes were incubated with monoclonal antibodies against CD3, CD4, CD8, CD19 and CD56 conjugated with three different fluorochromes. Measurement of the three different fluorescent emissions by flow cytometry enables quantification of the major types of human lymphocytes, T- and B-lymphocytes and natural killer (NK) cells. Since most flow cytometers may only use three different lasers simultaneously for cell analysis, this procedure represents the maximal current use of this technique.

Chang (1983) prepared matrix-like arrays of antibodies of distinct specificities on glass cover slips which acted as minute specific immuno-adsorbants for cells expressing the corresponding antigens on their surface. This procedure was based on the prior observations that cells are able to bind to surfaces coated with antibodies specific for the antigens on the surface of cells (Mage et al, 1977; Wysocki and Sato, 1978). Chang (1983) demonstrated specific binding of peripheral blood mononuclear cells to mouse anti-human HLA-A2 antibody adsorbed to glass cover slips and mouse thymocytes to immobilized anti-Lyt 2.1 and anti-Lyt 2.2 antibodies.

In work leading up to the present invention, the inventors determined that the detection of certain binding partners can be used to diagnose disease conditions and disorders, such as cancers and non-neoplastic disorders, as well as the presence of a normal condition. The detection system can also be used to determine the presence or absence of a range of antigens and can be used to quantitate their relative amounts. This is particularly important in chemical libraries, environmental samples and in phage display libraries.

SUMMARY OF THE INVENTION

One aspect of the present invention provides an assay device comprising an array of molecules wherein each molecule in the array, with the exception of a negative control, is capable of interaction with its respective binding partner putatively in a biological sample from an animal, avian species or plant wherein the pattern of interaction between the molecules and the binding partners is indicative of a normal condition or a disease condition or disorder or a propensity for the development of a disease condition or disorder.

In a related embodiment, the present invention is directed to an assay device comprising an array of molecules wherein each molecule in the array, with the exception of a negative control, is capable of interaction with its respective binding partner putatively in a chemical or phage display library or in an environmental sample wherein the pattern of interaction between the molecules and the binding partners is indicative of the presence, type and/or amount of a particular binding partner in said sample.

Another aspect of the present invention contemplates an assay device for the diagnosis of a normal condition or cancer or a propensity for the development of cancer in an animal such as a human, said assay device comprising an array of molecules immobilized to a solid support wherein each molecule of the array, with the exception of a negative control, is capable of interaction with a respective binding partner if present in a biological sample from said animal wherein the pattern of interaction between the immobilized molecules and their respective binding partners is indicative of the presence of cancer or a propensity to develop cancer.

A related aspect of the present invention provides an assay device for the diagnosis of a non-neoplastic disorder or a propensity for the development of a non-neoplastic disorder in an animal such as a human, said assay device comprising an array of molecules immobilized to a solid support wherein each molecule of the array, with the exception of a negative control, is capable of interaction with a respective binding partner if present in a biological sample from said animal wherein the pattern of interaction between the immobilized molecules and their respective binding partners is indicative of the presence of a non-neoplastic disorder or a propensity to develop a non-neoplastic disorder.

In a related embodiment, there is provided an assay device for the detection of a cell type or microbial, viral or parasitic agent or a pathogen, said assay device comprising an array of molecules immobilized to a solid support wherein each molecule of the array, with the exception of a negative control, is capable of interaction with a respective binding partner if present on said cell type, microbial or viral or parasitic agent or pathogen wherein the pattern of interaction between the immobilized molecules and their respective binding partners is indicative of the presence of said cell type, microbial or viral or parasitic agent or pathogen.

A further aspect of the present invention is directed to an array of molecules immobilized on a solid support said array defined by the formula:

$$[[Px_1]_b^{n_1} [Px_2]_c^{n_2} \cdots [Px_j]_d^{n_i}]_z$$

wherein

P is a member of a binding group capable of interacting with a binding partner;

$n_1$ $n_2$ ... $n_i$ represent different members of the binding group;

$x_1$ $x_2$ ... $x_j$ represent different binding groups;

b, c and d represent the number of different members of the binding groups $x_1$ $x_2$ ... $x_j$; respectively and wherein b, c and d may be the same or different and each is from about 0 to about 100 provided that at least one of b, c or d is not 0;

z is the number of groups of molecules on the array and is from about 1 to about 2000;

wherein the pattern of interaction between the immobilized molecules and their respective binding partners is indicative of a normal condition or disease condition or disorder or a propensity to develop said disease condition or disorder or the presence, type and/or amount of a binding partner.

A further aspect of the present invention contemplates an assay device for cancer said device comprising an array of immunoglobulin molecules or functional derivatives or equivalents thereof immobilized to discrete regions of the solid support such that different discrete regions have specificity for different antigens and wherein the antigens are expressed on the surface of normal cells or cancer cells or are released by normal cells or cancer cells wherein the binding pattern of the immobilized immunoglobulins to their respective antigens is indicative of the presence of cancer or a propensity to develop cancer or the presence of a normal condition.

A related aspect of the present invention provides an assay device for a non-neoplastic disorder said device comprising an array of immunoglobulin molecules or functional derivatives or equivalents thereof immobilized to discrete regions of the solid support such that different discrete regions have specificity for different antigens and wherein the antigens are expressed on the surface of non-neoplastic cells or are released by non-neoplastic cells wherein the binding pattern of the immobilized immunoglobulins to their respective antigens is indicative of the presence of a non-neoplastic disorder or a propensity to develop a non-neoplastic disorder.

In a further related embodiment, there is provided an assay device for a microbial, viral, parasitic or other pathogenic agent said device comprising an array of immunoglobulin molecules or functional derivatives or equivalents thereof immobilized to discrete regions of the solid support such that different discrete regions have specificity for different antigens and wherein the antigens are expressed on the surface of said microbial, viral, parasitic agents or pathogen or are released by same and the pattern of binding of the antigens to the immobilized immunoglobulins is indicative of the presence or absence of said microbe, virus, parasite or pathogen.

Still a further embodiment of the present invention is directed to an assay device for a binding partner in a chemical library, environmental sample or phage display library said device comprising an array of immunoglobulin molecules or functional derivatives or equivalents thereof immobilized to discrete regions of the solid support such that different discrete regions have specificity for different antigens wherein the pattern of binding of the antigens to the immobilized immunoglobulins is indicative of the presence, type and/or amount of said antigen.

Another aspect of the present invention is directed to an array of immunoglobulins or derivatives or chemical equivalents thereof specific for antigens expressed on normal cells or cancer cells or released by normal cells or cancer cells or expressed on microbes, viruses, parasites, pathogens or antigens putatively present in a chemical library or environmental sample wherein each group of immunoglobulins specific for each antigen or part thereof occupies a discrete region of a solid support, said array defined by the formula:

$$\left[ [q_{o_1}]_e^{m_1} [q_{o_2}]_f^{m_2} \cdots [q_{o_k}]_g^{m_i} \right]_y$$

wherein
- q is an immunoglobulin specific for an antigen expressed on a normal cell or cancer cell or antigen released by a normal cell or cancer cell or expressed on microbes, viruses, parasites, pathogens or antigens putatively present in a chemical library, environmental sample or phage display library;
- $m_1 m_2 \ldots m_i$ represent members of the same immunoglobulin group which bind to different parts of the same antigen;
- $o_1 o_2 \ldots o_k$ represent different groups of immunoglobulins defined by specificity to different antigens.
- e, f and g represent the number of different immunoglobulins within each of groups $o_1 o_2 \ldots o_k$, respectively and wherein e, f and g may be the same or different and each is from 0 to 100 provided that at least one of e, f and g is not 0;
- y is the number of groups of immunoglobulins on the array and is from about 1 to about 2000;

wherein the pattern of interaction between the immobilized immunoglobulins and their respective antigens is indicative of a normal condition or the development of cancer or a propensity to develop cancer or the presence of a microbe, virus, parasite or pathogen or the presence, type and/or amount of a binding partner in said chemical or environmental sample or phage display library.

A related aspect of the present invention provides an array of immunoglobulins or derivatives or chemical equivalents thereof specific for antigens expressed on non-neoplastic cells or released by non-neoplastic cells wherein each group of immunoglobulins specific for each antigen or part thereof occupies a discrete region of a solid support, said array defined by the formula:

$$\left[ [q_{o_1}]_e^{m_1} [q_{o_2}]_f^{m_2} \cdots [q_{o_k}]_g^{m_i} \right]_y$$

wherein
- q is an immunoglobulin specific for the antigen;
- $m_1 m_2 \ldots m_i$ represent members of the same immunoglobulin group which bind to different parts of the same antigen;
- $o_1 o_2 \ldots o_k$ represent different groups of immunoglobulins defined by specificity to different antigens.
- e, f and g represent the number of different immunoglobulins within each of groups $o_1 o_2 \ldots o_k$, respectively and wherein e, f and g may be the same or different and each is from 0 to 100 provided that at least one of e, f and g is not 0;
- y is the number of groups of immunoglobulins on the array and is from about 1 to about 2000;

wherein the pattern of interaction between the immobilized immunoglobulins and their respective antigens is indicative of the development of a non-neoplastic disorder or a propensity to develop a non-neoplastic disorder or the presence of a particular microbe, parasite, virus or pathogen.

Yet a further aspect of the present invention contemplates an assay device for cancer said device comprising an array of immunoglobulin molecules or functional derivatives or equivalents thereof immobilized to discrete regions of the solid support such that different discrete regions have specificity for different cluster of differentiation antigens and/or myeloid antigens and/or lymphoid antigens, expressed on leukemic cells wherein the binding pattern of the immobilized immunoglobulins to their respective antigens is indicative of the presence of cancer or a propensity to develop cancer.

Another aspect of the present invention provides a diagnostic assay device comprising an array of molecules wherein in each molecule in the array, with the exception of a negative control, is capable of interaction with its respective binding partner putatively in a biological sample from an animal, avian species or plant wherein the molecules are in an arrangement in said array such that upon interaction between the molecules and the binding partners a differential pattern of density provides an identifiable signal which is indicative of a disease condition or disorder or a propensity for the development of a disease condition or disorder.

A further aspect of the present invention contemplates an assay device for the diagnosis of cancer or a propensity for the development of cancer in an animal such as a human, said assay device comprising an array of molecules immobilized to a solid support wherein each molecule of the array, with the exception of a negative control, is capable of interaction with a respective binding partner if present in a biological sample from said animal wherein the molecules are in an arrangement in said array such that upon interaction between the immobilized molecules and their respective binding partners a differential pattern of density provides an identifiable signal which is indicative of the presence of cancer or a propensity to develop cancer.

Yet another aspect of the present invention is directed to an array of molecules immobilized on a solid support said array defined by the formula:

$$\left[ [Px_1]_b^{n_1} [Px_2]_c^{n_2} \cdots [Px_j]_d^{n_i} \right]_z$$

wherein
- P is a member of a binding group capable of interacting with a binding partner;

$n_1 n_2 \ldots n_i$ represent different members of the binding group;

$x_1 x_2 \ldots x_j$ represent different binding groups;

b, c and d represent the number of different members of the binding groups $x_1 x_2 \ldots x_j$; respectively and wherein b, c and d may be the same or different and each is from about 0 to about 100 provided that at least one of b, c or d is not 0;

z is the total number of groups of molecules on the array and is from about 1 to about 2000;

wherein molecules are in an arrangement in said array such that upon interaction between the immobilized molecules and their respective binding partners a differential pattern of densities within a binding group provides an identifiable signal which is indicative of a disease condition or disorder or a propensity to develop said disease condition or disorder.

A further aspect of the present invention contemplates an assay device for cancer said device comprising an array of immunoglobulin molecules or functional derivatives or equivalents thereof immobilized to discrete regions of the solid support such that different discrete regions have specificity for different antigens and wherein the antigens are expressed on the surface of normal cells or cancer cells or are released by normal cells or cancer cells wherein the binding immunoglobulins are in an arrangement in said array such that the pattern of the immobilized immunoglobulins to their respective antigens provides a differential pattern of density which is in the form of an identifiable signal and is indicative of the presence of cancer or a propensity to develop cancer.

Another further aspect of the present invention is directed to an array of immunoglobulins or derivatives or chemical equivalents thereof specific for antigens expressed on normal cells or cancer cells or released by normal cells or cancer cells wherein each group of immunoglobulins specific for each antigen or part thereof occupies a discrete region of a solid support, said array defined by the formula:

$$\left[[q_{o_1}]_e^{m_1} [q_{o_2}]_f^{m_2} \cdots [q_{o_k}]_g^{m_i}\right]_y$$

wherein q is an immunoglobulin specific for an antigen expressed on a normal cell or cancer cell or antigen released by a normal cell or cancer cell;

$m_1 m_2 \ldots m_i$ represent members of the same immunoglobulin group which bind to different parts of the same antigen;

$o_1 o_2 \ldots o_k$ represent different groups of immunoglobulins defined by specificity to different antigens.

e, f and g represent the number of different immunoglobulins within each of groups $o_1 o_2 \ldots o_k$, respectively and wherein e, f and g may be the same or different and each is from 0 to 100 provided that at least one of e, f and g is not 0;

y is the total number of groups of immunoglobulins on the array and is from about 1 to about 2000;

wherein the molecules are in an arrangement in said array such that upon interaction between the immobilized immunoglobulins and their respective antigens a differential pattern of density provides an identifiable signal which is indicative of the development of cancer or a propensity to develop cancer.

Yet a further aspect of the present invention contemplates an assay device for cancer said device comprising an array of immunoglobulin molecules or functional derivatives or equivalents thereof immobilized to discrete regions of the solid support such that different discrete regions have specificity for different cluster of differentiation (CD) antigens and/or myeloid (MY) and/or lymphoid (LY) antigens expressed on leukemic cells wherein the molecules are in an arrangement in said array such that upon binding of the immobilized immunoglobulins to their respective antigens a differential pattern of density provides an identifiable signal which is indicative of the presence of cancer or a propensity to develop cancer.

Another aspect contemplates a method for determining the presence of a disease condition or disorder or a propensity to develop a disease condition or disorder such as but not limited to cancer in an animal, avian species or plant, said method comprising obtaining a biological sample from said animal, avian species or plant comprising free binding partners or binding partners bound to a cell surface, said binding partners associated directly or indirectly with said disease condition or disorder and contacting said biological sample with a solid support comprising an array of molecules capable of binding to said binding partners wherein the molecules are in an arrangement in said array such that upon interaction with the binding partners a differential pattern of density provides an identifiable signal which is indicative of the disease condition or disorder or a propensity to develop said disease condition or disorder.

A further aspect of the present invention contemplates a method of detecting cancer or a propensity to develop cancer in a human or non-human animal, said method comprising obtaining a biological sample from said human or non-human animal and contacting said biological sample with an array of immunoglobulins or derivatives or chemical equivalents thereof specific for antigens expressed on normal cells or cancer cells or released by normal cells or cancer cells wherein each group of immunoglobulins specific for each antigen or part thereof occupies a discrete region of a solid support, said array defined by the formula:

$$\left[[q_{o_1}]_e^{m_1} [q_{o_2}]_f^{m_2} \cdots [q_{o_k}]_g^{m_i}\right]_y$$

wherein q is an immunoglobulin specific for an antigen expressed on a normal cell or cancer cell or antigen released by a normal cell or cancer cell;

$m_1 m_2 \ldots m_i$ represent members of the same immunoglobulin group which bind to different parts of the same antigen;

$o_1 o_2 \ldots o_k$ represent different groups of immunoglobulins defined by specificity to different antigens;

e, f and g represent the number of different immunoglobulins within each of groups $o_1 o_2 \ldots o_k$, respectively and wherein e, f and g may be the same or different and each is from 0 to 100 provided that at least one of e, f and g is not 0;

y is the total number of groups of immunoglobulins on the array and is from about 2 to about 2000;

wherein the molecules are in an arrangement in said array such that upon interaction between the immobilized immunoglobulins and their respective antigens a differential pattern of density provides an identifiable signal which is indicative of the development of cancer or a propensity to develop cancer.

Another aspect contemplates a method for determining the presence of a disease condition or disorder or a propensity to develop a disease condition or disorder such as but not limited to cancer in an animal, avian species or plant, said method comprising obtaining a biological sample from said animal, avian species or plant comprising free binding partners or binding partners bound to a cell surface, said binding partners associated directly or indirectly with said disease condition or disorder and contacting said biological sample with a solid support comprising an array of molecules capable of binding to said binding partners wherein the pattern of interaction with the binding partners is indicative of the disease condition or disorder or a propensity to develop said disease condition or disorder.

A further aspect of the present invention contemplates a method of detecting cancer or a propensity to develop cancer in a human or non-human animal, said method comprising obtaining a biological sample from said human or non-human animal and contacting said biological sample with an array of immunoglobulins or derivatives or chemical equivalents thereof specific for antigens expressed on normal cells or cancer cells or released by normal cells or cancer cells wherein each group of immunoglobulins specific for each antigen or part thereof occupies a discrete region of a solid support, said array defined by the formula:

$$\left[[q_{o_1}]_e^{m_1} [q_{o_2}]_f^{m_2} \cdots [q_{o_k}]_g^{m_i}\right]_y$$

wherein
q is an immunoglobulin specific for an antigen expressed on a normal cell or cancer cell or antigen release a normal cell or cancer cell;

$m_1$ $m_2$ ... $m_i$ represent members of the same immunoglobulin group which bind to different parts of the same antigen;

$o_1$ $o_2$ ... $o_k$ represent different groups of immunoglobulins defined by specificity to different antigens;

e, f and g represent the number of different immunoglobulins within each of groups $o_1$ $o_2$ ... $o_k$, respectively and wherein e, f and g may be the same or different and each is from 0 to 100 provided that at least one of e, f and g is not 0;

y is the total number of groups of immunoglobulins on the array and is from about 2 to about 2000;

wherein the pattern of interaction between the immobilized immunoglobulins and their respective antigens is indicative of the development of cancer or a propensity to develop cancer.

Still yet another aspect of the present invention is directed to the use of an array of molecules capable of interaction with a respective binding partner putatively in a biological sample to determine the presence of a disease condition or disorder or a propensity for the development of a disease condition or disorder.

Another aspect of the present invention contemplates a method of treating cancer in a human or non-human animal said method comprising obtaining a biological sample from said human or non-human animal and contacting said sample with an array of immunoglobulin molecules or functional derivatives or equivalents thereof immobilized to discrete regions of the solid support such that different discrete regions have specificity for different antigens and wherein the antigens are expressed on the surface of normal cells or cancer cells or are released by normal cells or cancer cells and determining the binding pattern of the immobilized immunoglobulins to their respective antigens and then undertaking immunotherapy such as with, but not limited to, humanized monoclonal antibodies corresponding to an antigen substantially expressed on cancer cells.

BRIEF DESCRIPTION OF THE FIGURES

FIG. 2 is a diagrammatic representation showing lineages for differentiation of blood cells in the bone marrow. Some antigens expressed on precursor cells and mature blood cells are indicated. Adapted from van Dongen et al (1988).

DETAILED DESCRIPTION OF THE PREFERRED EMBODIMENTS

Figure 1:
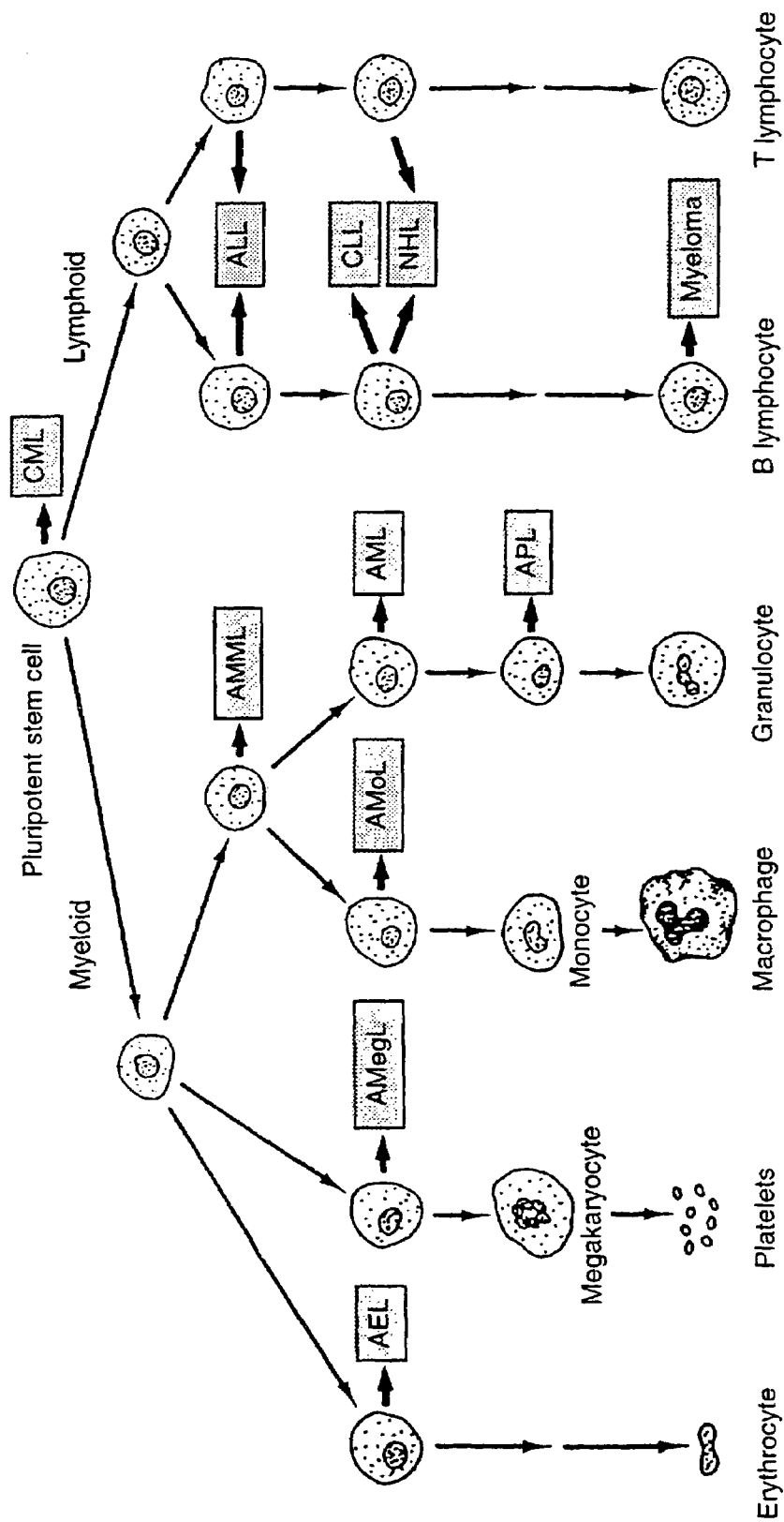
FIG. 1 is a diagrammatic representation showing lineages for blood cell differentiation with precursor cell types from which various types of leukemias arise. Determination of complete antigen expression would enable unequivocal diagnosis of the leukemia (c.f.

The present invention provides an assay device comprising an array of molecules capable of interaction with binding partners potentially present in a sample to be tested. In one embodiment, the presence or absence of interaction of the assay molecules with binding partners or the relative interaction between assay molecules and binding partners provides an indication of a normal condition or disease condition or disorder in the animal, avian species or plant from which the sample is derived. The assay device of the present invention is also useful for detecting changes in non-neoplastic cell populations such as changes in lymphocyte populations indicative of, for example, non-neoplastic disorders of the immune system. This latter aspect encompasses, therefore, the use of the assay device to detect directly or indirectly cell types and pathogens including parasites, viruses and microorganisms. In a further embodiment, the sample is a chemical library, an environmental sample or a phage display library. The pattern of binding then provides an indicator of the presence, type and/or amount of a particular binding partner. This is particularly useful in screening for environmental contaminants or screening natural products or chemical libraries for agents having particular affinities. It is also important for screening phage display libraries for peptide having particular affinities or binding profiles. The identification of such molecules is useful in the development of peptide mimetics.

Accordingly, one aspect of the present invention provides an assay device comprising an array of molecules wherein each molecule in the array, with the exception of a negative control, is capable of interaction with its respective binding partner putatively in a biological sample from an animal, avian species or plant wherein the pattern of interaction between the molecules and the binding partners is indicative of a normal condition or a disease condition or disorder or a propensity for the development of a disease condition or disorder.

The disease condition or disorder is preferably in an animal such as a human, primate, laboratory test animal (e.g. mouse, rabbit, guinea pig, hamster), companion animal (e.g. dog, cat) or captive wild animal.

The preferred animal is a human.

The present invention also extends, however, to the detection of disease conditions or disorders in avian species and plants. Examples of avian species include poultry birds (e.g. chickens, ducks, turkeys, geese), game birds (e.g. pheasants, wild ducks, peacocks) and flightless birds (e.g. emus, ostriches). Examples of plants include monocotyledonous and dicotyledonous plants including crop plants, fruit trees, ornamental plants and plantation trees. Reference herein to a "plant" includes reference to part of a plant such as leaves, flowers, stems and roots.

One type of disease or disorder applicable for detection in accordance with the present invention is cancer in animals such as humans. The term "cancer" is used in its broadest sense and includes benign and malignant leukemias, sarcomas and carcinomas as well as other neoplasias. Neoplasias may be either malignant or benign. The cancers and neoplasias contemplated by the present invention may be simple (monoclonal, i.e. composed of a single neoplastic cell type), mixed (polyclonal, i.e. composed of more than one neoplastic cell type) or compound (i.e. composed of more than one neoplastic cell type and derived from more than one germ layer). Examples of simple cancers encompassed by the present invention include tumors of mesenchymal origin (e.g. tumors of connective tissue, endothelial tissue, blood cells, muscle cells) and tumors of epithelial origin. Particular cancers contemplated by the present invention include but are not limited to fibrosarcoma, myxosarcoma, Ewing's sarcoma, granulocytic leukemia, basal cell carcinoma, colon cancer, gastric cancer and a variety of skin cancers. Even more particularly, the cancers contemplated by the present invention include but are not limited to CML, Chronic Myeloid Leukemia; AMML, Acute Myelomonocytic Leukemia; ALL, Acute Lymphocytic Leukemia; AEL, Acute Erythrocytic Leukemia; AmegL, Acute Megakaryocytic Leukemia; AMoL, Acute Monocytic Leukemia; AML, Acute Myeloid Leukemia; CLL, Chronic Lymphocytic Leukemia; NHL, Non-Hodgkins Lymphoma; APL, Acute Promyelocytic Leukemia and HCL, Hairy Cell Leukemia.

Reference to a "normal" condition includes the presence and/or amounts of particular cell types or antigens including, for example, receptors, ion channels, cell-cell interaction molecules, signalling molecules which, based on statistical analysis can most likely be expected in a substantially healthy population of subjects. This aspect of the present invention is useful, for example, in monitoring patients after chemical or immune therapy, or screening for a state of health in an at risk individual or group or population of individuals. Reference to determining a "normal" condition includes, therefore, detecting an "abnormal" condition.

In a related embodiment, the present invention is directed to an assay device comprising an array of molecules wherein each molecule in the array, with the exception of a negative control, is capable of interaction with its respective binding partner putatively in a chemical or phage display library or environmental sample wherein the pattern of interaction between the molecules and the binding partners is indicative of the presence, type and/or amount of a particular binding partner in said sample.

A "chemical sample" includes a chemical library such as a library of synthetic molecules, biological molecules or molecules produced using combinatorial means. The chemical library may also be synthesized using pin technology (e.g. Chiron). Reference to a chemical library includes a library of naturally occurring molecules for natural product screening.

An "environmental sample" includes a sample from an aquatic, or air or terrestrial environment as well as samples from plants, microorganisms and coral. Accordingly, an environmental sample includes a sample for screening natural products for use, for example, as pharmaceutical or diagnostic agents. It also includes samples such as soil, water and air which may contain a contaminant.

A "phage display library" is used in its broadest sense and includes two or more phage particles having one or more heterologous peptides, polypeptides or proteins on the phage coat. Generally, however, each phage produces one particular peptide, polypeptide or protein fused to a coat protein or functional portion thereof. The phage particles are brought into contact with the immobilized molecules. Where a phage particle comprises a peptide, polypeptide or protein on its coat capable of binding to an immobilized molecule, the phage becomes immobilized. The immobilized phage is then eluted and the genetic material encoding the peptide, polypeptide or protein isolated and cloned. This is a particularly powerful method for isolating peptide, polypeptide or protein mimetics. For example, mimetics can be isolated based on analogous binding characteristics.

In one particular example, if the immobilized molecule is an antibody to CD40 ligand, and a peptide, polypeptide or protein on a phage display or other library binds to the antibody, then this peptide, polypeptide or protein becomes a candidate molecule to act as an activator of B-lymphocytes or as an antagonist. Similarly, the immobilized molecule may be an antibody to CD154 which is elevated in patients suffering from lupus. A molecule identity wheel which is capable of binding to a CD154 antibody or CD154 ligand would be a candidate antagonist of CD154 useful in the treatment of lupus. A similar rationale applies for all other libraries such as chemical or natural product libraries.

Another aspect of the present invention contemplates an assay device for the diagnosis of a normal condition or cancer or a propensity for the development of cancer in an animal such as a human, said assay device comprising an array of molecules immobilized to a solid support wherein each molecule of the array, with the exception of a negative control, is capable of interaction with a respective binding partner if present in a biological sample from said animal wherein the pattern of interaction between the immobilized molecules and their respective binding partners is indicative of the presence of cancer or a propensity to develop cancer.

Another type of condition or disorder contemplated for detection in accordance with the present invention includes non-neoplastic disorders. A non-neoplastic disorder is considered herein to include any disorder or disease which is not characterized by uncontrolled cell proliferation and includes non-neoplastic disorders of the immune system. Such disorders include autoimmune disease including Type 1 diabetes, multiple sclerosis, psoriasis, rheumatoid arthritis, scleroderma and systemic lupus erythematosis. These disorders are caused by sub-sets of T cells which may express CD4, and/or production of antibodies against autoantigens by sub-sets of B cells which may express CD19. For example, abnormalities in lymphocyte populations such as a decrease in CD4+, CD45+ T lymphocytes and an increase in CD8+, CD57+ T lymphocytes are characteristic in patients with systemic lupus erythematosis.

Other non-neoplastic disorders include congenital immunodeficiency in children resulting in recurrent infections. Immunophenotyping by flow cytometry is used to detect deficiencies in lymphocyte sub-sets. Severe Combined Immunodeficiency Syndrome (SCIDS) is caused by a deficiency in the enzyme, adenosine deaminase, with very low levels of peripheral blood lymphocytes, such as T (CD3) and B (CD19) and Natural Killer (CD16) cells. A deficiency of purine nucleoside phosphorylase results in a deficiency of B cells. The antibody array of the present invention provides definitive information on the sub-sets of lymphocytes which are deficient. This facilitates diagnosis of the condition.

The present antibody array is also useful in screening for infection by pathogenic agents such as viruses, bacteria and parasites including malarial parasites. For example, the Human Immunodeficiency Virus (HIV) infects mainly CD4+ lymphocytes because the gp120 protein of HIV binds to CD4. In the course of development of AIDS, there is a depletion of CD4+ lymphocytes. However, many other cell types are infected by HIV including macrophages, B lymphocytes and microglial cells. Currently, the population of CD4 lymphocytes is monitored in patients with HIV, but immunophenotyping should be more extensive as recommended by the Centre for Disease Control (CDC, Atlanta, USA). The following double labelling tests are presently done by flow cytometry: negative controls, CD45/CD14, CD3/CD4, CD3/CD8, CD3/CD19, CD3/CD16, CD3/CD56 and CD4/CD8. This labour-intensive procedure is replaceable, in accordance with the present invention, by a single-step procedure using an array containing antibodies against these CD antigens and additional antigens which further define the sub-sets of affected lymphocytes. When patients are infected with HIV, there is a rapid decline in CD4+lymphocytes to a minimal value at approximately 6 weeks followed by a partial recovery in their levels by 12 weeks. In the longer term, there is a progressive decline in CD4+ lymphocytes leading to death after approximately 11 years (Shinton, 1998). Treatment with zidovudine (AZT) induces a transient increase in CD4+ lymphocytes; the effects of chemotherapy on various sub-sets of lymphocytes are proposed, in accordance with the present invention, to be determined with an antibody array to monitor the clinical progression of HIV patients.

Immunophenotyping is also useful for bone marrow and organ transplantation for determination of the degree of immunosuppression and complications such as rejection or infection. Flow cytometry is used before transplantation for tissue typing using monoclonal antibodies to detect HLA-antigens, or for cross-matching. Tolerance to transplanted tissues is induced by administration of cyclosporin to the patient. Treatment at the time of transplantation forces the level of peripheral blood lymphocytes to almost zero. The disappearance of T cells from the blood is monitored by flow cytometry for CD3+ cells. Following transplantation, an increase in CD8+ cells signals possible rejection. Increases in CD8+ and CD16+, CD56+ and/or CD57+ cells may indicate viral infection. This surveillance of the immune state of the transplant patient is proposed to be done more rapidly and extensively using an antibody array of the present invention.

Some cancer patients receive high-dose chemotherapy and then require a bone marrow transplant to regenerate their depleted immune system. The transplanted marrow then induces haematopoietic reconstitution but unusual sub-sets of lymphocytes sometimes appear, such as CD5+ T cells. Opportunistic infections and graft-versus-host disease may occur in such patients resulting in an increase in CD8+ cells in both cases and an elevation of Natural Killer cells. Replacement of flow cytometry with an antibody array for CD antigens simplifies the monitoring of patients and provides more extensive information.

Antibody arrays for CD antigens are also useful for monitoring changes in lymphocyte sub-sets during desensitisation therapy to insect or spider venom, for example, where the numbers of CD4+ CD45RA+ lymphocytes increase and CD4+ CD45RO+ lymphocytes decrease from elevated levels.

Patients with Chronic Fatigue Syndrome may have immunological abnormalities consistent with a viral infection with activated CD8+ lymphocytes. A detailed analysis of lymphocyte sub-sets establishes enlarged diagnostic criteria and provides extensive information on this disorder.

Accordingly, another aspect of the present invention provides an assay device for the diagnosis of a non-neoplastic disorder or a propensity for the development of a non-neoplastic disorder in an animal such as a human, said assay device comprising an array of molecules immobilized to a solid support wherein each molecule of the array, with the exception of a negative control, is capable of interaction with a respective binding partner if present in a biological sample from said animal wherein the pattern of interaction between the immobilized molecules and their respective binding partners is indicative of the presence of a non-neoplastic disorder or a propensity to develop a non-neoplastic disorder.

In a related embodiment, there is provided an assay device for the detection of a cell type or microbial or viral agent or a pathogen, said assay device comprising an array of molecules immobilized to a solid support wherein each molecule of the array, with the exception of a negative control, is capable of interaction with a respective binding partner if present on said cell type, microbial, viral or parasitic agent or pathogen wherein the pattern of interaction between the immobilized molecules and their respective binding partners is indicative of the presence of said cell type, microbial, viral or parasitic agent or pathogen.

In a further embodiment, the sample screened is a chemical library, phage display library or environmental sample. The pattern of interaction provides the presence, type and/or amount of binding partner. This aspect of the present invention is particularly useful for screening for environmental contaminants or screening a chemical or biological library of molecules for a molecule with a particular affinity, binding profile, immunological profile and/or concentration. A chemical or biological library includes -a phage display library or other form of library. A chemical library may be synthetic or naturally occurring.

The expression "pattern of interaction" is used in its broadest context to include: the presence or absence of interaction relative to background interaction; the relative density of interaction such as the relative density of cells bound to a discrete spot on the array relative to background; the pattern of morphology of cells which are bound to a discrete spot on the array; the presence or absence of internal molecules in cells lysed on a discrete spot on the array; the relative number of cells or antigens on the array; the differential expression of particular antigens, and the number of antigens per cell. Any or all of the above criteria may be used to assess the interaction between an immobilized molecule and its binding partner. The pattern of expression may also be subject to quantitation.

The solid support is typically glass or a polymer, such as but not limited to cellulose, ceramic material, nitrocellulose, polyacrylamide, nylon, polystyrene and its derivatives, polyvinylidene difluoride (PVDF), methacrylate and its derivatives, polyvinyl chloride or polypropylene. Nitrocellulose is particularly useful and preferred in accordance with the present invention. A solid support may also be a hybrid such as a nitrocellulose film supported on a glass or polymer matrix. Reference to a "hybrid" includes reference to a layered arrangement of two or more glass or polymer surfaces listed above. The solid support may be in the form of a membrane or tubes, beads, discs or microplates, or any other surface suitable for conducting an assay. Binding processes to immobilize the molecules are well-known in the art and generally consist of covalently binding (e.g. cross linking) or physically adsorbing the molecules to the solid substrate.

The molecule immobilized to the solid support of the present invention is referred to herein as "P". Molecule P is generally selected from a binding group designated "x". A number, n, of P molecules may be selected from each binding group or one P molecule may be selected from each binding group. P molecules may be arranged in any geometric form on the solid support such as a spot, dot, or group of dots or spots or in a spread or layered format. Generally, the spot or dot format is preferred. The binding groups are selected on the basis of the normal condition or disease condition or disorder being diagnosed or the binding partner sought to be detected or quantitated. In the case of cancer, for example, a particular cancer or the development of cancer in general may be determined on the basis of the expression of certain cell-surface ligands (and more particularly antigens) or the release of soluble ligands (e.g. soluble antigens). The P molecules are then selected as binding partners to the cell surface or soluble ligands. The pattern of interaction between the P molecules and their respective binding partners is indicative of the development of, or a propensity to develop, cancer or other disease conditions or disorders. In the case of detecting a microbial, viral or parasitic agent or a pathogen, the P molecules are generally selected as binding partners to cell surface molecules such as sugars, proteins, lipoproteins, flagella, pilli, receptors or cell wall components. In the case of a chemical library, phage display library or environmental sample, the P molecules are generally, but not necessarily, selected on the basis of a presumed structure or affinity in the sample. In the case of a phage display library, for example, the assay looks for a peptide, polypeptide or protein on the phage which binds to an immobilized molecule thereby becoming an affinity mimetic. Such molecules then become candidates for further analogues as potential protein mimetics.

The array may also comprise a positive and/or negative control to assist in maintaining quality control of the assay procedure. A positive control, for example, may be a P molecule capable of interaction with a binding partner known to be present in the biological or chemical sample.

Another aspect of the present invention is directed to an array of molecules immobilized on a solid support said array defined by the formula:

$$[[Px_1]_b^{n_1} [Px_2]_c^{n_2} \cdots [Px_j]_d^{n_j}]_z$$

wherein
P is a member of a binding group capable of interacting with a binding partner;
$n_1\ n_2\ \ldots\ n_i$ represent different members of the binding group;
$x_1\ x_2\ \ldots\ x_j$ represent different binding groups;
b, c and d represent the number of different members of the binding groups $x_1\ x_2 \ldots x_j$; respectively and wherein b, c and d may be the same or different and each is from about 0 to about 100 provided that at least one of e, f and g is not 0;
z is the total number of groups of molecules on the array and is from about 2 to about 2000;

wherein the pattern of interaction between the immobilized molecules and their respective binding partners is indicative of a normal condition or disease condition or disorder or a propensity to develop said disease condition or disorder or the presence, type and/or amount of a binding partner.

Preferably, the disease condition or disorder is cancer.

Preferably, the molecules on the array are arranged in discrete spots. z is the number of discrete spots of different types of molecules. Conveniently, the spots are arranged in duplicate, hence, the total number of spots on the array is 2z.

The representation ". . ." means optionally further members in the group between, for example, $[Px_2]_c^{n_2}$ and $[Px_j]_d^{n_i}$ The representation of the array by formula is not to imply any limitation as to shape or sequence of the array.

In a particularly preferred embodiment, the P molecules are immunoglobulins and their binding partners are antigens. However, the present invention extends to other classes of P molecules such as but not limited to receptors, ligands for receptors, T cell derived antigen-binding molecules (TABM) or other molecules having affinity for certain ligands such as lectins, nucleic acid binding proteins amongst others. Most preferably, the P molecule is an immunoglobulin capable of interaction with an antigen present, for example, on the surface of a normal cell or cancer cell or a soluble antigen released by a normal cell or cancer cell or present in a chemical library, phage display library or environmental sample.

In a particularly preferred embodiment, the array of P molecules and more particularly immunoglobulin molecules is selected on the basis of antigens likely to be expressed during a disease condition or disorder such as cancer or an antigen generally present on a normal cell or an antigen present on a microbial, viral or parasitic agent or pathogen. The "antigen" may also be part of a chemical library, phage display library or in an environmental sample. The term "antigen" is used in its broadest sense and includes plasma membrane associated proteins with extracellular domains, proteins associated with ion channels, as well as receptors, carbohydrate moieties and the like. The pattern of binding of immunoglobulin molecules to target antigens then assists in the diagnosis of the disease condition or the determination of a normal condition. The array would most preferably further comprise an internal positive and negative control.

Accordingly, another aspect of the present invention contemplates an assay device for cancer said device comprising an array of immunoglobulin molecules or functional derivatives or equivalents thereof immobilized to discrete regions of the solid support such that different discrete regions have specificity for different antigens and wherein the antigens are expressed on the surface of normal cells or cancer cells or are released by normal cells or cancer cells wherein the binding pattern of the immobilized immunoglobulins to their respective antigens is indicative of the presence of cancer or a propensity to develop cancer or the presence of a normal condition.

In a related embodiment, there is provided an assay device for a non-neoplastic disorder said device comprising an array of immunoglobulin molecules or functional derivatives or equivalents thereof immobilized to discrete regions of the solid support such that different discrete regions have specificity for different antigens and wherein the antigens are expressed on the surface of non-neoplastic cells or are released by non-neoplastic cells wherein the binding pattern of the immobilized immunoglobulins to their respective antigens is indicative of the presence of a non-neoplastic disorder or a propensity to develop a non-neoplastic disorder.

In a further related embodiment, there is provided an assay device for a microbial, viral, parasitic or other pathogenic agent said device comprising an array of immunoglobulin molecules or functional derivatives or equivalents thereof immobilized to discrete regions of the solid support such that different discrete regions have specificity for different antigens and wherein the antigens are expressed on the surface of said microbial, viral or parasitic agent or pathogen or are released by same and the pattern of binding of the antigens to the immobilized immunoglobulins is indicative of the present or absence of said microbe, virus, parasite or pathogen.

Still a further embodiment of the present invention is directed to an assay device for a binding partner in a chemical library, phage display library or environmental sample said device comprising an array of immunoglobulin molecules or functional derivatives or equivalents thereof immobilized to discrete regions of the solid support such that different discrete regions have specificity for different antigens wherein the pattern of binding of the antigens to the immobilized immunoglobulins is indicative of the presence, type and/or amount of said binding partner.

Generally, a range of immunoglobulins is selected on the basis of antigens expressed on normal cells, cancer cells, potential cancer cells, microbes, viruses, parasites or other pathogens, cells infected or affected by a pathogen, or antigens sought in a chemical library, phage display library or environmental sample. Each group of immunoglobulins specific for a different antigen is defined by $x_1 x_2 \ldots x_j$. In one embodiment, a sample would contain a mixed population of cells and the immunoglobulin molecules on the array are designed to selectively bind to antigens on particular cell types. In another embodiment, the sample is a mixture of chemical molecules including synthetic compounds (e.g. alkanes, alkenes, aromatics, polymers, cyclic molecules), oligosaccharides, proteins, lipids, lipoproteins and carbohydrates. The immunoglobulins may also be directed to different epitopes on the same antigen. A discrete antibody spot may comprise immunoglobulins with a single epitope specificity or the immunoglobulins may be a heterogeneous group to multiple epitopes on the one antigen. A discrete antibody spot may also contain multiple antibodies to different antigens but all expressed, for example, on a particular cell. This is useful if the capture of the cell is imported for subsequent analysis.

Within each of groups $x_1 x_2 \ldots x_j$, a number of immunoglobulin sub-groups may exist specific for different parts of the same antigen defined by the groups $x_1 x_2 \ldots x_j$. These sub-groups are defined by $n_1 n_2 \ldots n_i$.

Accordingly, another aspect of the present invention is directed to an array of immunoglobulins or derivatives or chemical equivalents thereof specific for antigens expressed on normal cells or cancer cells or released by normal cells or cancer cells or expressed on microbes, viruses, parasites or pathogens or antigens putatively present in a chemical library, phage display library or environmental sample wherein each group of immunoglobulins specific for each antigen or part thereof occupies a discrete region of a solid support, said array defined by the formula:

$$\left[ [q_{o_1}]_e^{m_1} [q_{o_2}]_f^{m_2} \cdots [q_{o_k}]_g^{m_i} \right]_y$$

wherein
- q is an immunoglobulin specific for an antigen expressed on a normal cell or cancer cell or antigen released by a normal cell or cancer cell or expressed on microbes, viruses, parasites or pathogens or antigens putatively present in a chemical library, phage display library or environmental sample;
- $m_1 m_2 \ldots m_i$ represent members of the same immunoglobulin group which bind to different parts of the same antigen;
- $o_1 o_2 \ldots o_k$ represent different groups of immunoglobulins defined by specificity to different antigens.
- e, f and g represent the number of different immunoglobulins within each of groups $o_1 o_2 \ldots o_k$, respectively and wherein e, f and g may be the same or different and each is from 0 to 100;
- y is the total number of groups of immunoglobulins on the array and is from about 2 to about 2000;

wherein the pattern of interaction between the immobilized immunoglobulins and their respective antigens is indicative of a normal condition or the development of cancer or a propensity to develop cancer or the presence of a microbe, virus, parasite or pathogen or the presence, type and/or amount of a binding partner in said chemical or environmental sample.

As stated above, the array may also contain a positive and/or negative control. Generally, the immunoglobulins are arranged in discrete spots where y is the total number of discrete spots of different types of immunoglobulins. Preferably, the spots are arranged in duplicate. The representation "..." is as hereinbefore defined.

In a particularly preferred embodiment, the immunoglobulins interact with cluster of differentiation or cluster designation (CD) antigens or myeloid (MY) or lymphoid (LY) antigens expressed on leukemic cells. Cancer or a propensity to develop cancer is detected by an increase in the population or proportion of cells carrying particular antigens.

Accordingly, another aspect of the present invention contemplates an assay device for cancer said device comprising an array of immunoglobulin molecules or functional derivatives or equivalents thereof immobilised to discrete regions of the solid support such that different discrete regions have specificity for different cluster designation antigens and/or myeloid and/or lymphoid antigens expressed on leukemic cells wherein the binding pattern of the immobilised immunoglobulins to their respective antigens is indicative of the presence of cancer or a propensity to develop cancer.

Preferably, the immunoglobulins are monoclonal antibodies but the present invention extends to polyclonal antibodies or antigen-binding parts (e.g. Fab fragments), derivatives, homologues or analogues thereof as well as fusion or hybrid antibodies, synthetic antibodies or recombinant antibodies.

Still another aspect of the present invention provides an array of immunoglobulins or derivatives or chemical equivalents thereof specific for antigens expressed on non-neoplastic cells or released by non-neoplastic cells or expressed on microbial or parasitic cells or pathogens or on viruses wherein each group of immunoglobulins specific for each antigen or part thereof occupies a discrete region of a solid support, said array defined by the formula:

$$\left[ [q_{o_1}]_e^{m_1} [q_{o_2}]_f^{m_2} \cdots [q_{o_k}]_g^{m_i} \right]_y$$

wherein q is an immunoglobulin specific for the antigen;

$m_1 m_2 \ldots m_i$ represent members of the same immunoglobulin group which bind to different parts of the same antigen;

$o_1 o_2 \ldots o_k$ represent different groups of immunoglobulins defined by specificity to different antigens.

e, f and g represent the number of different immunoglobulins within each of groups $o_1 o_2 \ldots o_k$, respectively and wherein e, f and g may be the same or different and each is from 0 to 100 provided that at least one of e, f and g is not 0;

y is the number of groups of immunoglobulins on the array and is from about 1 to about 2000;

wherein the pattern of interaction between the immobilised immunoglobulins and their respective antigens is indicative of the development of a non-neoplastic disorder or a propensity to develop a non-neoplastic disorder or the presence of a particular microbe, parasite, pathogen or virus.

The detection of antigen-immunoglobulin binding may be accomplished in any number of ways. For example, where the antigens are cell surface antigens, the array may be designed to permit the binding of cells to the immobilised immunoglobulins. The captured cells may then be analysed microscopically, with the use of various stains, biochemically or immunologically.

Alternatively, the immobilised immunoglobulins act as capture molecules for particular cell types and the expression of other antigens on normal or cancer cells is then determined using labelled antibodies (e.g. fluorescently or radioactively labelled antibodies) or by other convenient means. Preferably, the antibodies are in free solution. The capture molecules may also be for soluble antigens or for cells disrupted from solid tumors. In relation to the latter, conveniently, cell suspensions are produced from solid tumor biopsies and the cell suspensions are brought into contact with the immunoglobulin array.

Where the array of immobilised immunoglobulins is designed to bind to free (i.e. soluble antigen), then the captured antigen may be detected immunologically or by other means.

The assay device of the present invention is preferably a solid support having a flat, planar surface. Examples of suitable solid supports include membranes, plastic cover slips, glass slides or the wells of microtitre trays. Nitrocellulose is particularly preferred. The solid support comprises an array of immunoglobulin coated regions, preferably in the form of spots or other geometric pattern. The spots are discrete and surrounded by regions not containing any immunoglobulin molecules. The immunoglobulins within a given region or spot are generally immobilised by covalent or non-covalent bonds. The preferred immunoglobulins are monoclonal antibodies.

Preferably, the spots of the array are arranged in a sequence such as a rectangular, triangular or spherical matrix where the position of an immunoglobulin region is defined by coordinates based on, for example, row and column. The array of immunoglobulins may cover any convenient region such as from about 0.1 $mm^2$ to about 100 $mm^2$, preferably about 0.5 $mm^2$ to about 15 $mm^2$. Generally, each region or spot is made up of immunoglobulins having a single distinct specificity. Specificity in this context is with respect to different antigens or different regions of the one antigen. The preferred number of immunoglobulin spots is from about 7 to about 1000 and more preferably from about 10 to about 1000. Most preferably, the immunoglobulins are arranged in multiples such as duplicates, triplicates or greater.

The immobilised array of immunoglobulins is then contacted by a biological sample comprising cells, cell debris, cell extracts, tissue fluid, serum, blood, cerebrospinal fluid, urine, lymphatic fluid, aspirate, bone marrow aspirate, mucus or other tissue or body fluid. Alternatively, the sample is a chemical sample or environmental sample such as a chemical library, aquatic sample or terrestrial sample. Preferably, the sample would contain a mixed population of cells. The contact is for a time and under conditions sufficient for cells carrying particular antigens to be captured by the immobilised immunoglobulin or for free antigens to be captured by the immobilised immunoglobulins. The captured cells and antigens may then be detected by any convenient means such as biochemically, histochemically, immunologically or microscopically. Immunologic detection is particularly convenient. For example, a second immunoglobulin specific for a captured antigen or cell, labelled with a reporter molecule, may be added. The identification of the reporter molecule indicates that the antigen is captured. Alternatively, after the second immunoglobulin is added and it forms a complex with the captured antigen, an anti-immunoglobulin immunoglobulin labelled with a reporter molecule is added and the presence of a signal from the reporter molecule determined.

By "reporter molecule", as used in the present specification, is meant a molecule which, by its chemical nature, provides an analytically identifiable signal which allows the detection of immunoglobulin bound antigen. Detection may be either qualitative or quantitative. The most commonly used reporter molecules in this type of assay are either enzymes, fluorophores or radionuclide containing molecules (i.e. radioisotopes). In the case of an enzyme immunoassay, an enzyme is conjugated to the second or third immunoglobulin, generally by means of glutaraldehyde or periodate. As will be readily recognised, however, a wide variety of different conjugation techniques exist which are readily available to one skilled in the art. Commonly used enzymes include horseradish peroxidase, glucose oxidase, β-galactosidase and alkaline phosphatase, amongst others. The substrates to be used with specific enzymes are generally chosen for the production, upon hydrolysis by the corresponding enzyme, of a detectable colour change. It is also possible to employ fluorogenic substrates which yield a fluorescent product.

Alternatively, fluorescent compounds, such as fluorescein and rhodamine, may be chemically coupled to immunoglobulins without altering their binding capacity. When activated by illumination with light of a particular wavelength, the fluorochrome-labelled immunoglobulin adsorbs the light energy, inducing a state of excitability in the molecule, followed by emission of the light at a characteristic colour visually detectable microscopically or using other imaging devices such as a confocal microscope or 2 dimensional laser scanner (e.g. Fluorimager or Typhoon, Molecular Dynamics, Inc., Sunnyvale, USA).

The presence of cancer or a propensity to develop cancer or the presence of a non-cancer disease condition may be indicated by a change in particular cell numbers or proportion of cell numbers carrying particular antigens. For example, an increase in certain cell types will be indicative of particular conditions.

Another aspect of the present invention contemplates a method for determining the presence of a disease condition or disorder or a propensity to develop a disease condition or disorder such as but not limited to cancer in an animal, avian species or plant, said method comprising obtaining a biological sample from said animal, avian species or plant comprising free binding partners or binding partners bound to a cell surface, said binding parties associated directly or indirectly with said disease condition or disorder and contacting said biological sample with a solid support comprising an array of molecules capable of binding to said binding partners wherein the pattern of interaction with the binding partners is indicative of the disease condition or disorder or a propensity to develop said disease condition or disorder.

Preferably, the binding partners comprise two or more different antigens associated with the disease condition or disorder and the array of molecules is an array of immunoglobulins having specificity for the different groups of antigens.

The pattern of interaction may be determined by any convenient means such as by immunoassay, microscopic examination or histological or biochemical techniques. The pattern of interaction may also be determined by electrical impulse, electronic emissions and/or radioactive emissions.

In a particularly preferred embodiment, the present invention contemplates a method of detecting cancer or a propensity to develop cancer in a human or non-human animal, said method comprising obtaining a biological sample from said human or non-human animal and contacting said biological sample with an array of immunoglobulins or derivatives or chemical equivalents thereof specific for antigens expressed on normal cells or cancer cells or released by normal cells or cancer cells wherein each group of immunoglobulins specific for each antigen or part thereof occupies a discrete region of a solid support, said array defined by the formula:

$$\left[ [q_{o_1}]_e^{m_1} [q_{o_2}]_f^{m_2} \ldots [q_{o_k}]_g^{m_i} \right]_y$$

wherein
q is an immunoglobulin specific for an antigen expressed on a normal cell or cancer cell or antigen released by a normal cell or cancer cell;
$m_1$ $m_2$ ... $m_i$ represent members of the same immunoglobulin group which bind to different parts of the same antigen;

$o_1$ $o_2$ ... $o_k$ represent different groups of immunoglobulins defined by specificity to different antigens.

e, f and g represent the number of different immunoglobulins within each of groups $o_1$ $o_2$ ... $o_k$, respectively and wherein e, f and g may be the same or different and each is from 0 to 100 provided that at least one of e, f and g is not 0;

y is the total number of groups of immunoglobulins on the array and is from about 2 to about 2000;

wherein the pattern of interaction between the immobilized immunoglobulins and their respective antigens is indicative of the development of cancer or a propensity to develop cancer.

Yet another aspect of the present invention is directed to the use of an array of molecules capable of interaction with a respective binding partner putatively in a biological sample to determine the presence of a disease condition or disorder or a propensity for the development of a disease condition or disorder.

Preferably, the molecules are immunoglobulins.

Preferably, the immunoglobulins are specific for all bound antigens or soluble antigens such as antigens on or shed by cancer cells.

In a particularly preferred embodiment, the pattern of interaction is measured qualitatively or quantitatively as a pattern of density of either cells bound to the molecules in the array or cell-free antigens which have bound to the molecules of the array. The pattern of density may, for example, be determined macroscopically or microscopically or may be made with the aid of artificial intelligence such as using a computer guided densitometer. In addition, the present invention encompasses quantitation of binding pattern. Such computational aspects of the antibody arrays include, for example, numbers of cells, antigen- or cell-binding patterns, densities of binding numbers of cells per spot or numbers of antigens per cell.

Accordingly, another aspect of the present invention provides an assay device comprising an array of molecules wherein in each molecule in the array, with the exception of a negative control, is capable of interaction with its respective binding partner putatively in a biological sample from an animal, avian species or plant wherein the molecules are in an arrangement in said array such that upon interaction between the molecules and the binding partners a differential pattern of density provides an identifiable signal which is indicative of a disease condition or disorder or a propensity for the development of a disease condition or disorder.

More particularly, the present invention contemplates an assay device for the diagnosis of cancer or a propensity for the development of cancer in an animal such as a human, said assay device comprising an array of molecules immobilized to a solid support wherein each molecule of the array, with the exception of a negative control, is capable of interaction with a respective binding partner if present in a biological sample from said animal wherein the molecules are in an arrangement in said array such that upon interaction between the immobilized molecules are their respective binding partners a differential pattern of density provides an identifiable signal which is indicative of the presence of cancer or a propensity to develop cancer.

Preferably, the immobilized molecules are immunoglobulins and the binding partners are cell bound antigens, internal cellular antigens or soluble (i.e. free) antigens.

In a particularly preferred embodiment, the immunoglobulins are arranged on the array such that if a cancer being screened is present, the pattern of interaction provides a differential density which gives an identifiable shape, such as a letter, numeral or geometric design which can be readily detected.

For example, the antigens likely to be expressed during Acute Myeloid Leukemia (AML) can be arranged such that the letter "A" is preferentially shown as more dense dots relative to background. The letter "A" is used for the purposes of exemplification only, since any geometric shape or arrangement may be used.

Yet another aspect of the present invention is directed to an array of molecules immobilized on a solid support said array defined by the formula:

$$\left[ [Px_1]_b^{n_1} [Px_2]_c^{n_2} \ldots [Px_j]_d^{n_j} \right]_z$$

wherein
P is a member of a binding group capable of interacting with a binding partner;
$n_1$ $n_2$ . . . $n_i$ represent different members of the binding group;
$x_1$ $x_2$ . . . $x_j$ represent different binding groups;
b, c and d represent the number of different members of the binding groups $x_1$ $x_2$ . . . $x_j$; respectively and wherein b, c and d may be the same or different and each is from about 0 to about 100 provided that at least one of b, c or d is not 0;
z is the total number of groups of molecules on the array and is from about 1 to about 2000;

wherein molecules are in an arrangement in said array such that upon interaction between the immobilized molecules and their respective binding partners, a differential pattern of densities within a binding group provides an identifiable signal which is indicative of a disease condition or disorder or a propensity to develop said disease condition or disorder.

Still a further aspect of the present invention contemplates an assay device for cancer said device comprising an array of immunoglobulin molecules or functional derivatives or equivalents thereof immobilized to discrete regions of the solid support such that different discrete regions have specificity for different antigens and wherein the antigens are expressed on the surface of normal cells or cancer cells or are released by normal cells or cancer cells wherein the binding immunoglobulins are in an arrangement in said array such that the pattern of the immobilized immunoglobulins to their respective antigens provides a differential pattern of density which is in the form of an identifiable signal and is indicative of the presence of cancer or a propensity to develop cancer.

Even yet another further aspect of the present invention is directed to an array of Immunoglobulins or derivatives or chemical equivalents thereof specific for antigens expressed on normal cells or cancer cells or released by normal cells or cancer cells wherein each group of immunoglobulins specific for each antigen or part thereof occupies a discrete region of a solid support, said array defined by the formula:

$$\left[ [q_{o_1}]_e^{m_1} [q_{o_2}]_f^{m_2} \ldots [q_{o_k}]_g^{m_i} \right]_y$$

wherein
q is an immunoglobulin specific for an antigen expressed on a normal cell or cancer cell or antigen released by a normal cell or cancer cell;
$m_1$ $m_2$ . . . $m_i$ represent members of the same immunoglobulin group which bind to different parts of the same antigen;
$o_1$ $o_2$ . . . $o_k$ represent different groups of immunoglobulins defined by specificity to different antigens.
e, f and g represent the number of different immunoglobulins within each of groups $o_1$ $o_2$ . . . $o_k$, respectively and wherein e, f and g may be the same or different and each is from 0 to 100 provided that at least one of e, f and g is not 0;
y is the total number of groups of immunoglobulins on the array and is from about 1 to about 2000;

wherein the molecules are in an arrangement in said array such that upon interaction between the immobilized immunoglobulins and their respective antigens, a differential pattern of density provides an identifiable signal which is indicative of the development of cancer or a propensity to develop cancer.

Still yet a further aspect of the present invention contemplates an assay device for cancer, said device comprising an array of immunoglobulin molecules or functional derivatives or equivalents thereof immobilized to discrete regions of the solid support such that different discrete regions have specificity for different cluster of differentiation (CD) antigens and/or lymphoid (LY) and/or myeloid (MY) antigens expressed on leukemic cells wherein the molecules are in an arrangement in said array such that upon binding of the immobilized immunoglobulins to their respective antigens a differential pattern of density provides an identifiable signal which is indicative of the presence of cancer or a propensity to develop cancer.

Another aspect contemplates a method for determining the presence of a disease condition or disorder or a propensity to develop a disease condition or disorder such as but not limited to cancer in an animal, avian species or plant, said method comprising obtaining a biological sample from said animal, avian species or plant comprising free binding partners or binding partners bound to a cell surface, said binding partners associated directly or indirectly with said disease condition or disorder and contacting said biological sample with a solid support comprising an array of molecules capable of binding to said binding partners wherein the molecules are in an arrangement in said array such that upon interaction with the binding partners a differential pattern of density provides an identifiable signal which is indicative of the disease condition or disorder or a propensity to develop said disease condition or disorder.

Yet a further aspect of the present invention contemplates a method of treating cancer in a human or non-human animal said method comprising obtaining a biological sample from said human or non-human animal and contacting said sample with an array of immunoglobulin molecules or functional derivatives or equivalents thereof immobilized to discrete regions of the solid support such that different discrete regions have specificity for different antigens and wherein the antigens are expressed on the surface of normal cells or cancer cells or are released by normal cells or cancer cells and determining the binding pattern of the immobilized immunoglobulins to their respective antigens and then undertaking immunotherapy using antibodies against the expressed antigens. These antibodies are preferably humanized monoclonal antibodies. A similar method may also be employed to treat non-neoplastic conditions.

The assay device and the methods for conducting the assays of the present invention are readily adapted for automation. For example, robotic systems may be used to deliver appropriate amounts including nanoliter volumes of immunoglobulins to a solid support such as a nitrocellulose film or microtitre plate. After appropriate treatment, the immobilized immunoglobulins may then be used in any assay. Again, this may be automated or conducted using robotics.

The present invention further contemplates the use of an antibody array as herein described in the manufacture of an assay device for the detection of a disease condition or a propensity for development of a disease condition or to detect a microbe, virus, parasite or pathogen or to screen a chemical library, phage display library or environmental sample.

The array of the present invention may also be adapted for use on a microchip. Microchip technology permits the generation of thousands of antibody patterns for a range of conditions and further permits automation and/or computer analysis. A "microchip" includes a matrix support comprising an array of adapter molecules, ligands or potential binding partners.

The present invention further contemplates a method of treatment comprising identifying an antigen using an antibody array which is specific to a diseased cell or which is specific to a diseased condition or which acts as a protein mimetic, preparing an antibody to said antigen or a cytotoxic agent specific to said antigen and then administering said antibody or cytotoxic agent for a time and under conditions sufficient to effect said treatment.

In one embodiment, the antibody is a humanised form of a non-human-derived antibody. In another embodiment, the human or humanized antigen is conjugated to a cytotoxic molecule. The present invention extends to pharmaceutical compositions comprising the antibody, cytotoxic agent or protein mimetic. Such a composition may also contain one or more pharmaceutically acceptable carriers and/or diluents.

By way of example only, the present invention is now described with reference to one particular embodiment, ie. the use of an array to detect CD antigens. The following description is in no way intended to limit the instant invention to one particular embodiment.

Figure 2:
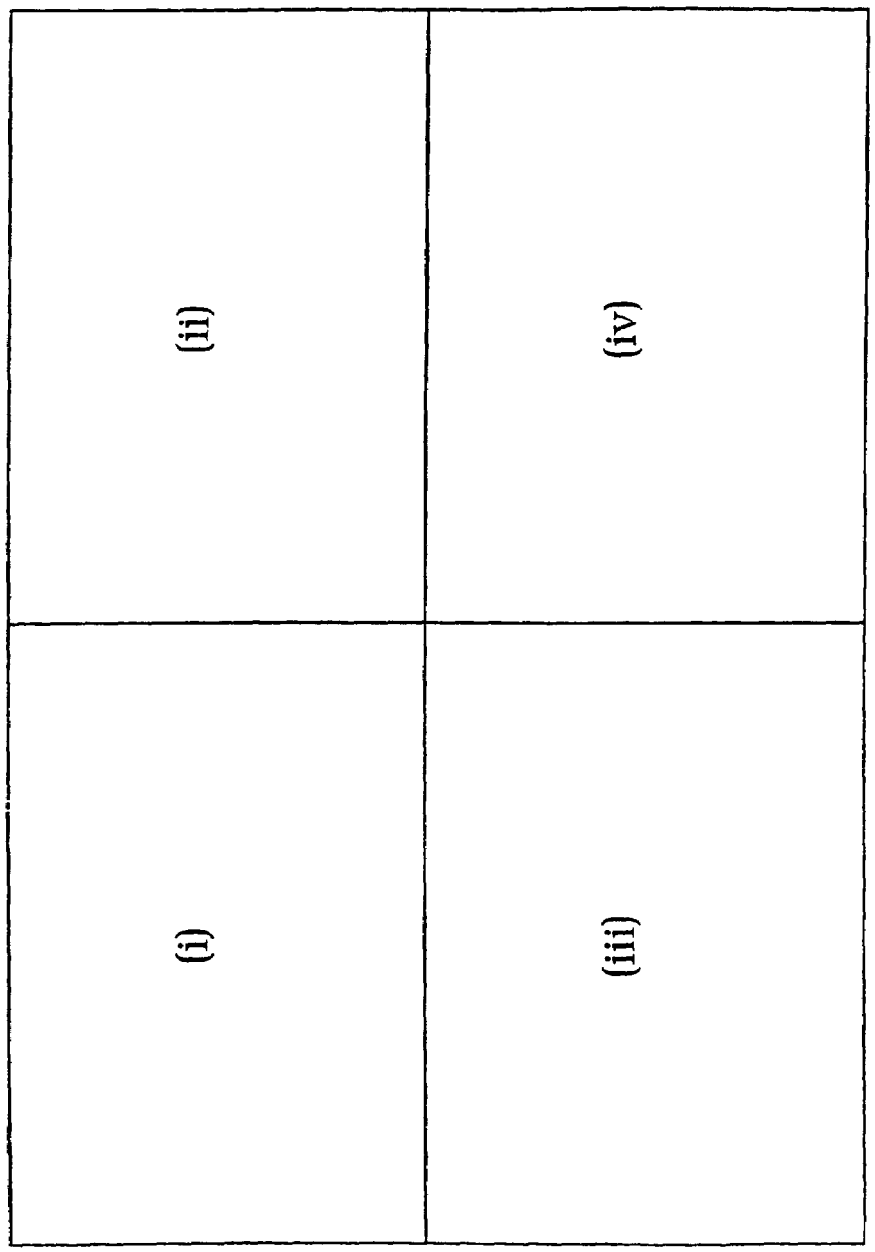
FIG. 2). CML, Chronic Myeloid Leukemia; AMML, Acute Myelomonocytic Leukemia; ALL, Acute Lymphocytic Leukemia; AEL, Acute Erythrocytic Leukemia; AmegL, Acute Megakaryocytic Leukemia; AMoL, Acute Monocytic Leukemia; AML, Acute Myeloid Leukemia; CLL, Chronic Lymphocytic Leukemia; NHL, Non-Hodgkins Lymphoma; APL, Acute Promyelocytic Leukemia. Adapted from Cooper (1993).
Figure 2:
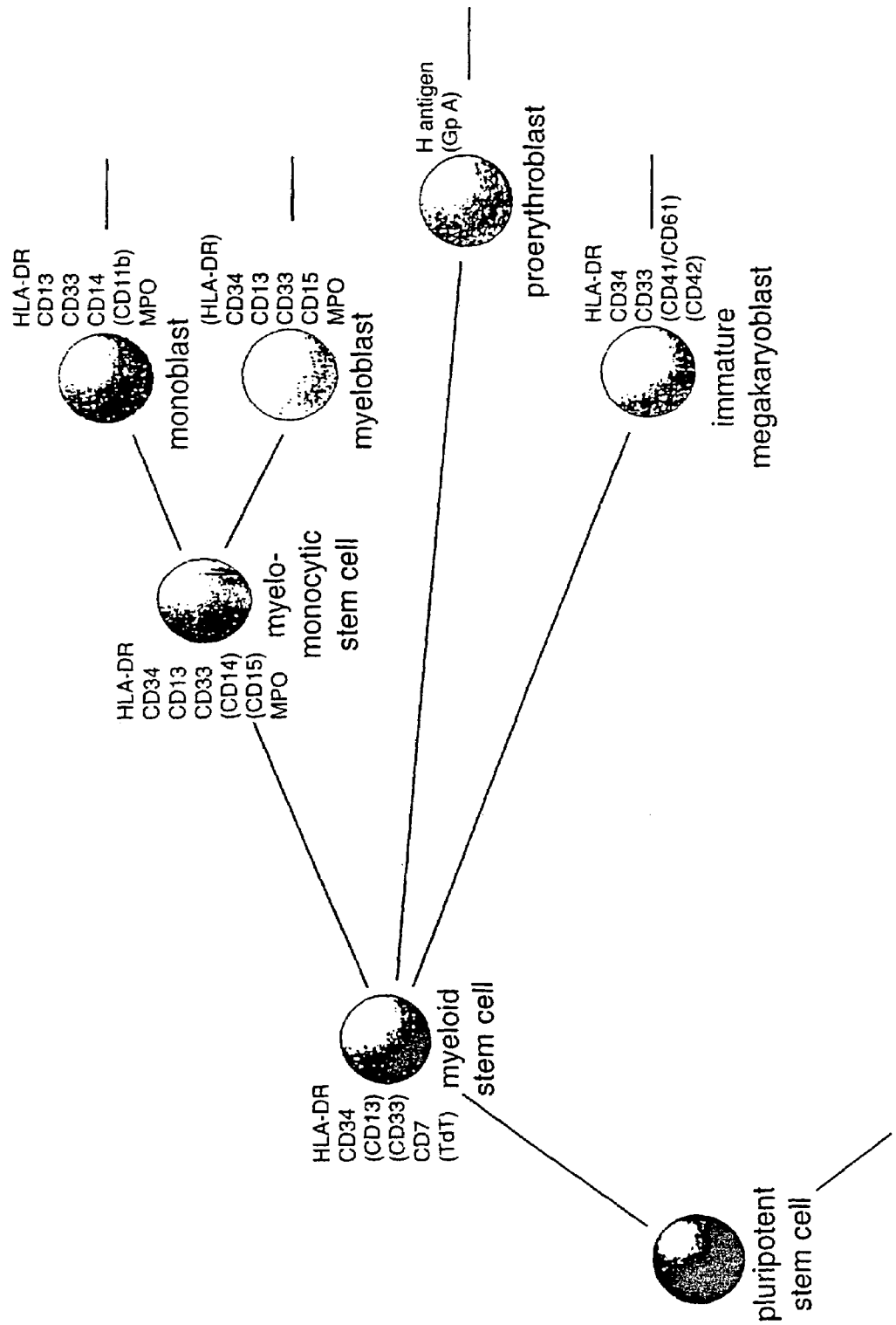
Figure 3A:
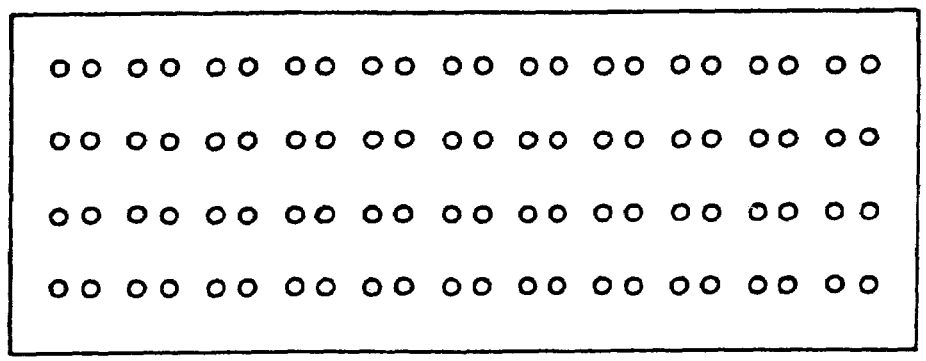
FIG. 3 is a diagrammatic representation of (a) a top view and (b) a perspective view of an immunoassay device comprising an array of discrete antibody spots.
Figure 3B:
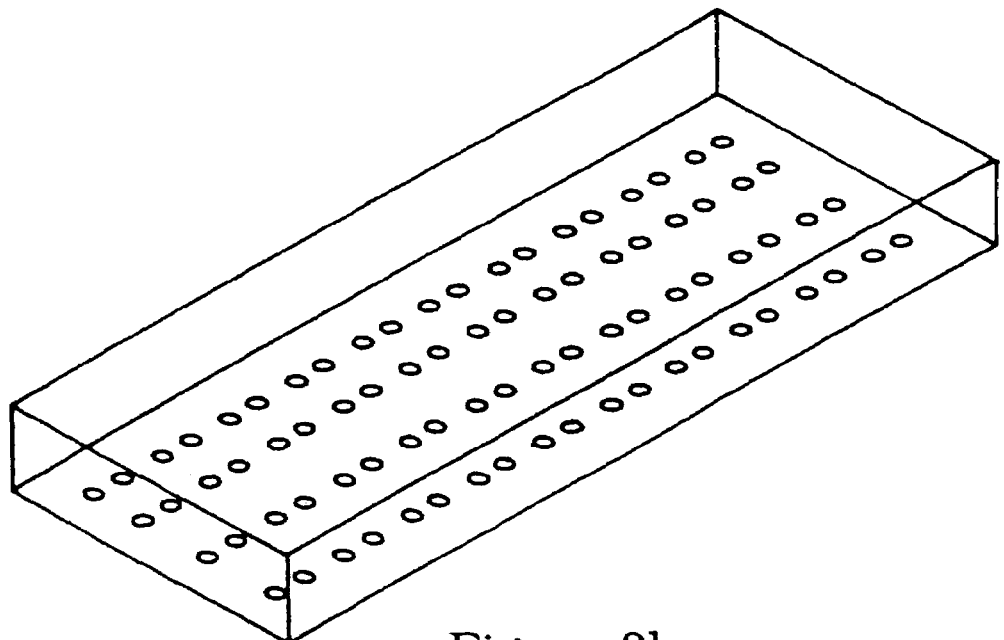

The antibody array of this aspect of the present invention enables rapid and simultaneous detection of the expression of CD antigens on the surface of leukocytes isolated from blood. Antibodies against 51 CD antigens, 4 murine isotype control antibodies (IgG1, IgG2a, IgG2b, IgM) and antibodies against 7 other surface markers important in the diagnosis of leukemias (Glycophorin A, HLA-DR, KOR-SA3544, FMC7, immunoglobulin, kappa and lambda) are attached as 5 nL dots to a film of nitrocellulose on microscope slides. Only leukocytes which express particular CD antigens bind to the corresponding antibody dot. Particular categories of leukocytes expressing specific sub-sets of CD antigens are identified by the dot pattern obtain from the binding of cells to the CD antibody array. Various types of leukocytes and leukemias are identified with a high degree of certainty by the pattern of expression of CD antigens, where different sub-sets of leukocytes express different combinations of approximately 12-20 of the antigens represented in the array (FIGS. 1 and 2). This form of multi-factorial analysis is based upon pattern recognition for different leukocytes or leukemias. The present invention permits a large number of antibodies to be used which makes this identification quite robust with variations of expression tolerated between different samples or individuals.

Mature leukocytes differentiate from stem cells in the bone marrow along particular lineages to myeloid cells and T- and B-lymphocytes. The expression of CD antigens changes as precursor cells differentiate from stem cells along the various lineages to mature sub-populations of leukocytes which express a particular sub-set of CD antigens. Thus, the sub-set of CD antigens expressed on a leukemia may be similar to that of a precursor cell in a particular lineage. Alternatively, blockade of a particular lineage by mutation may result in differentiation of precursors to cells that express an unusual combination of CD antigens.

Application of the subject antibody array is illustrated by determination of the expression of CD antigens on normal peripheral blood leukocytes (PBLs) and Chronic Lymphocytic Leukemia (CLL) cells. The CLL cells bound to the antibody dots with a uniform intensity. In addition, CLL cells bound to fewer antibody dots than normal PBLs. Blood samples were tested from CLL patients with advanced disease with white blood cell (WBC) counts of $30\text{-}86 \times 10^9$ cells/L and also from patients with WBC counts comparable to the density of normal PBLs ($10 \times 10^9$ cells/L). The antibody array pattern for this low level CLL was still distinguishable from that of normal PBLs (see results for CLL patient KB, shown in FIG. 8c).

In summary, a prototype array of 62 antibodies (54 and 60 dot arrays are shown in FIGS. 7 and 8, respectively) was used to enable rapid and reproducible identification of sub-sets of CD antigens on normal PBLs and .CLL cells. This array enables diagnosis of different types of leukemias and lymphomas based upon CD antigen expression. Identification of unusual CD antigens on a leukemia or a lymphoma provides a target for treatment of the patient with a humanised monoclonal antibody against that antigen. For example, Rituximab is anti-CD20 used to treat B-cell lymphomas, such as Non-Hodgkins Lymphoma (NHL). Campath-1H is anti-CD52 used to treat chronic T- and B-cell leukemias such as T-PLL and B-CLL. CD antibody arrays of this type are also useful for diagnosis and treatment of non-neoplastic disorders involving leukocytes such as auto-immune and immuno-deficiency diseases, HIV and mononucleosis. In addition, the method could be used for analysing leukocytes in cord blood and bone marrow aspirates.

The following description provides the most preferred method for preparing the antibody arrays. The panel of antibodies is generally used to construct antibody arrays with the Cartesian Technologies PixSysTM 3200 Aspirate and Dispense System. The antibodies are chosen for use in a particular diagnosis or detection protocol. Each antibody is generally applied in the volume of from about 1 to about 10 nanoliters in a dot format at approximately from 0.5 to 1.5 mm intervals to create an appropriate array on a nitrocellulose film generally laid on a solid support such as but not limited to a microscope slide. After dotting, the supports are assessed on a light box and the corners of the arrays-marked gently using, for example, a lead pencil. The antibody arrays are then immersed in a blocking agent such as but not limited to skim milk, Irish moss extract or other source of carrageenan or gelatin. From about 2% to about 15% w/v skim milk powder in PBS at 4° C. overnight or at 37° C. for from about 60-120 minutes is particularly useful. After application of the blocking agent, the solid supports are washed gently with purified water and allowed to dry at room temperature for a period of time from about 60-120 minutes. The solid supports are then stored in an airtight bag at 4° C. in the dark.

The cells to be tested on the antibody arrays are freshly harvested or reconstituted from liquid nitrogen storage. The cells are washed in PBS and resuspended at a density of from about $1 \times 10^5$ to $1 \times 10^9$ cells/mL. Solid supports are then prepared by warming same to room temperature and moistened with PBS. The nitrocellulose is then wiped dry around the edges of the marked array and placed in a moist environment such as a petri dish lined with damp tissues. From about 100 to about 500 μL of cell suspension is pipetted onto the slide within the wiped edges of the array. The array is then incubated with the cells in the humidified closed petri dish for approximately 30 minutes at room temperature. The time and temperature of incubation at this point may be varied to suit the particular conditions for the convenience of the person conducting the assay.

After incubation with the cells, the solid supports are carefully submerged or immersed in PBS then placed in a petri dish of PBS and gently agitated to wash off cells not bound specifically to the array. If significant background binding has occurred as observed by microscopic examination, then the washing step is repeated.

The array is then observed microscopically, for example, using an Olympus BX60 fluorescence microscope (Olympus Optical Company, Japan), with a UPLan 4× objective with the condensor set at the phase 1 position and a green filter over the light source. Images are captured and analyzed using a SenSys digital cooled CCD camera (1317×1035 Pixels, Photometrics), PCI Frame Grabber and Windows Image Processing and Analysis Software (Digital Optics). Images are processed for presentation using Adobe Photoshop version 3.0 software. The intensities for specific binding of cells to each antibody dot is also recorded using a relative scale of +/−, +, ++, +++.

After recording the results as computer files, the antibody array bound cells are fixed by bathing the slide in FACS fixative (0.94% v/v formaldehyde, 2% D-glucose, 0.03% v/v $NaN_3$, PBS (pH 7.3)) for 30 minutes. After rinsing in PBS, the bound cells are stained for 5 mins with Hemotoxylin counterstain (Inmmunotech, Marseille, France) which stains the nuclei of cells blue. The solid supports are then rinsed in PBS, dried and stored at room temperature. The solid supports may then be subsequently wetted with PBS and re-examined microscopically.

Although the subject invention is particularly exemplified with respect to using the assay to detect cancer, as described above, the assay may also be used to detect or quantitate a particular molecule or class or family of molecules in a chemical sample such as a chemical library, phage display library or in an environmental sample. It may also be used to detect or quantitate particular microbes, viruses, parasites or other pathogens. The present invention extends to all these aspects.

Furthermore, the present invention extends to the use of genetic means to conduct the assays. In this instance, the P molecules would be oligonucleotides. The binding partner would be a DNA or RNA (e.g. mRNA) sequence capable of hybridizing to a P molecule. In a particularly preferred embodiment, the binding partner is DNA produced by reverse transcriptase such as using RT-PCR.

In one particular example, the array may be used to detect CD antigen expression on leukocytes, leukemias or lymphomas. The array would comprise a microarray of oligonucleotides corresponding to all of the CD antigens (166 or a particular sub-set). This microscopic array would consist of tiny (pL) dots of complementary oligonucleotides (~20 nucleotides [nt]) covalently linked to a solid support. mRNA is extracted from 5,000-10,000 leukocytes and amplified by RT-PCR with end-labelling of the resultant DNA transcripts with biotin or $^{32}P$. The labelled DNAs are then hybridized to the oligonucleotide array and unbound DNA removed by washing. The presence of DNA transcripts of mRNAs are detected with a high resolution fluorescence or radioactivity scanner yielding a dot pattern for expression of CD mRNAs. This dot pattern would correspond to that obtained with the antibody array with bound leukocytes.

This alternative procedure for detection of CD antigen expression is more sensitive than that using intact cells, but requires more sophisticated instrumentation. This procedure is particularly useful for detection of minimal residual disease in patients in remission.

The present invention extends to such a genetic assay.

The present invention is further described by the following non-limiting Examples.

EXAMPLE 1

Preparation of Antibody Array

The antibodies may be covalently linked to a suitable membrane such as an Immobilon P membrane (PVDF; Millipore Corporation). Subsequent blocking with an excess of a protein solution such as a skim milk preparation is preferred. A blocking agent is designed to eliminate non-specific binding on the binding surface. Other suitable blocking agents are Irish moss extract or other source of carrageenan or gelatin. The antibodies are also adsorbed to a nitrocellulose film on a glass microscope slide (Schleicher and Schuell, NH, USA) and the unbound nitrocellulose is then blocked with skim milk. Antibodies are also adsorbed to Nylon membranes. To increase the accessibility of bound anti-CD antibodies to antigens on cells, the solid support used for the array is initially coated with a recombinant, truncated form of Protein G from *Streptococcus* which retains its affinity for the Fc portion of IgG but lacks albumin and Fab binding sites, and membrane-binding regions (Goward et al., 1990). Antibodies are applied to this coat of Protein G and bind via their Fc domains leaving the Fab domains free to interact with cells. The Fab domains are also further from the solid support providing greater accessibility of CD antigens on cell membranes to antibodies.

The array of antibodies is also constructed on a membrane or a coverslip. In this case, the antibodies are covalently linked to the membrane as duplicate spots in a two-dimensional matrix. The spots are arranged in a matrix such as but not limited to a 15×15 matrix. The antibodies are monoclonal and are specific for the cluster of differentiation (cluster designation) antigens (CD antigens) and myeloid (MY) antigens expressed on leukemia cells. Antibodies specific for LY antigens may also be included. Details of CD antigens are available at the website of the National Centre for Biotechnology Information (NCBI), a division of the National Library of Medicine (HLM) at the National Institutes of Health (NIH). The spots are of microscopic size and are produced by the application of a drop (~10 nanoliters) of antibody solution (e.g. $10^F$ g protein/ml) on designated portions of a membrane or glass surface such as a coverslip, first washed with a nonspecific protein absorbent such as 30% w/v skim milk (Dutch Jug, Bonlac Foods Ltd., Melbourne, Australia) and then also recorded using a relative scale of +/−, +, ++, +++.

EXAMPLE 2

Preparation of Sample

Blood samples are used as a source of antigens or cell-surface expressed antigens after treatment to prevent clot formation. Peripheral blood lymphocytes may be fractionated by centrifugation to produce a "buffy coat" or more specifically by Ficoll-Hypaque density media. Further fractionation of lymphocyte or other cell sub-populations may be conducted using Dynabeads which are magnetic beads covalently linked to a specific antibody. Generally, cells are resuspended in Hank's solution at a density of $2 \times 10^6$ cells/ml and are applied to an antibody array as a uniform suspension of 200 μL. The Hanks solution is isotonic and contains glucose which maintains the viability and integrity of the cells during this binding step. After incubation of the cell suspension with the antibody array for 30-60 minutes (e.g. 30 minutes) at 37° C. in a humid atmosphere, the unbound cells are washed from the array with phosphate buffered saline (PBS; two aliquots of 20 μL) which is then decanted. Alternatively, the unbound cells are suspended by gentle rocking and the array is subject to washing with pre-warmed Hanks solution (3×1 mL).

EXAMPLE 3

Improved Method of Preparing Sample

A panel of antibodies (such as 51 spots of antibodies) is used to construct antibody arrays with the Cartesian Technologies PixSysTM 3200 Aspirate and Dispense System. The monoclonal antibodies are chosen for diagnosis of common types of leukemias. Templates for the antibody arrays on the slides are presented in FIGS. 7A and 8A. Each antibody (5 nL) is dotted at 0.8 mm intervals to create a 0.65 cm×0.45 cm array on the nitrocellulose film on a microscope slide. After dotting, the slides are assessed on a light box and the corners of the arrays are marked gently with a lead pencil.

The antibody arrays are then immersed in 5% w/v blocking agent such as skim milk, bovine serum albumin (BSA), calf serum, Irish moss extract or other source of carrageenan or gelatin in PBS at 4° C. overnight, equivalent to a 90 min blocking at 37° C. After blocking, the slides are washed gently with purified water and allowed to dry thoroughly at room temperature for 90 mins. The slides are then wrapped in GladWrap (trade mark), sealed in an air-tight bag and stored at 4° C. in the dark.

Cells to be tested on the antibody arrays are freshly harvested or reconstituted from liquid nitrogen storage. Cells are washed in PBS and resuspended at a density of $1 \times 10^7$ cells/mL. Slides to be tested are unwrapped, warmed to room temperature and moistened with PBS. The nitrocellulose is then wiped dry around the edges of the marked array and placed in a petri dish lined with damp tissues. The cell suspension (300 μL) is carefully pipetted onto the slide within the wiped edges of the array. The array was incubated with the cells in the humidified closed petri dish for 30 mins at room temperature.

After incubation with the cells, the slide is carefully dipped into a 50 mL tube of PBS, then placed in a petri dish of PBS and gently swirled to wash off cells not bound specifically to the array. If significant background binding is still observed by microscopic examination of the slide, this step is repeated until the binding pattern is apparent.

EXAMPLE 4

Assay

Samples of cells or antigens are applied to the antibody-membrane array, incubated to enable maximal binding and non-bound material is then removed by a suitable washing solution. Generally, bound cells are fixed to the antibodies by chemical cross-linking. Cells bound to antibodies in the array are visualized microscopically to determine morphologies. Where necessary, cells are fixed to the array and stained, treated enzymatically and/or tested for enzymic and/or receptor expression.

Fixed cells may also be interacted with a second antibody labelled with a reporter molecule (e.g. fluorochrome). Alternatively, a series of "second" antibodies are used each with a different fluorochrome. Expression of multiple antigens on cells is then determined by fluorescence confocal microscopy.

Fixed cells are also stained or fluorescently labelled to enable quantification of cell densities in the original body fluid sample. This quantification may be automated with a programmable scanner which records cell densities at each antibody dot in the array. For example, a laser densitometer (Molecular Dynamics Inc, Sunnyvale, Calif., USA) which scans in two dimensions (resolution 50 $^F$m) is particularly useful. The degree of staining of the antibody spots is proportional to the number of cells bound to each antibody. For fluorescence detection, a FluorImager or Typhoon (Molecular Dynamics, Inc.) can be used (resolution 50 im).

The antibody array such as against CD and MY antigens provides a pattern of expression of the antigens and this is then matched to set patterns of antigen expression for different leukemias (e.g. acute myeloid leukemia [AML]). For AML (M4), for example, the following antigens are expressed: MY4 (CD14), MY7, MY9 and M01 (CD11b).

EXAMPLE 5

Detection of Human T and B Cell Lines

Figure 5A:
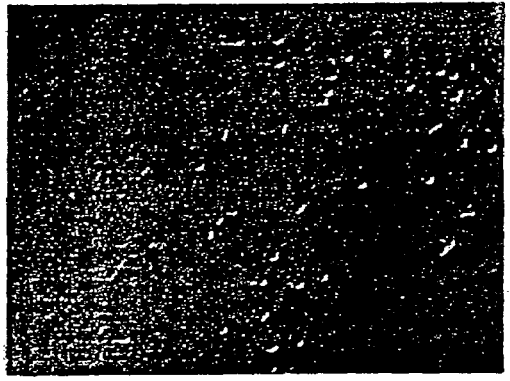
FIG. 5 shows Nomarski micrographs of human CCRF-CEM leukemia and Raji lymphoma cells bound to some of the spots of an antibody (Coulter Beckman) array absorbed to a nitrocellulose film on a glass microscope slide (Molecular Probes). The procedures used are described in Examples 1 and 2, except that antibodies were applied in a volume of 0.4 FL. A, CCRF-CEM cells; B, Raji cells.
Figure 5A:
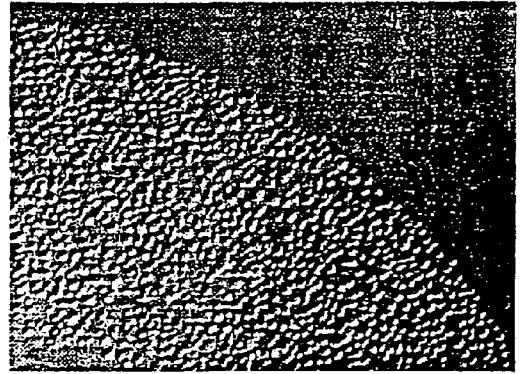
Figure 5A:
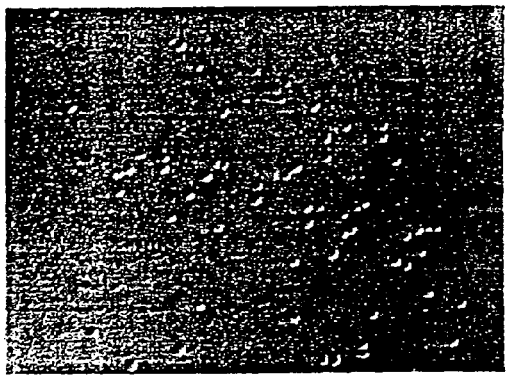
Figure 5A:
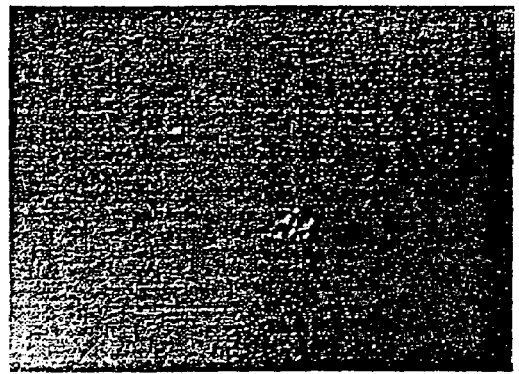
Figure 5A:
Figure 5A:
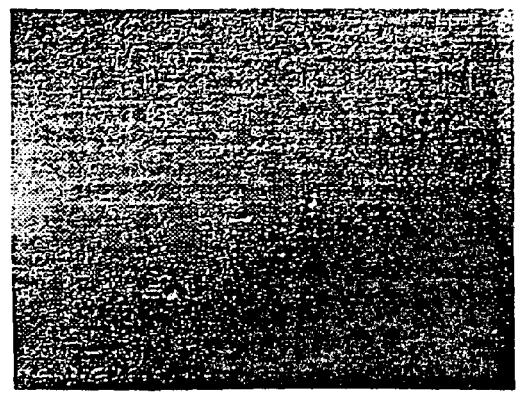
Figure 5B:
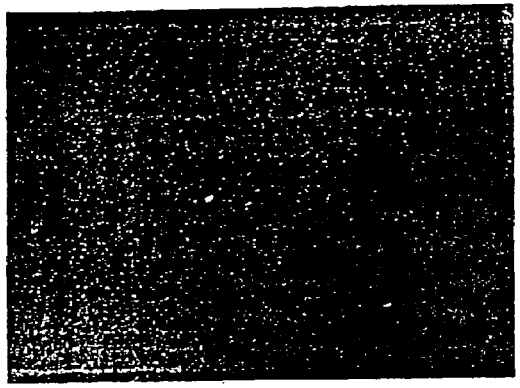
Figure 5B:
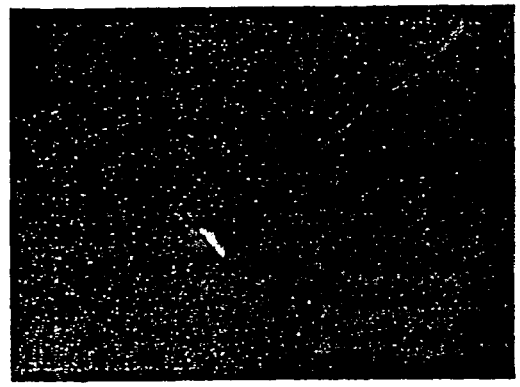
Figure 5B:
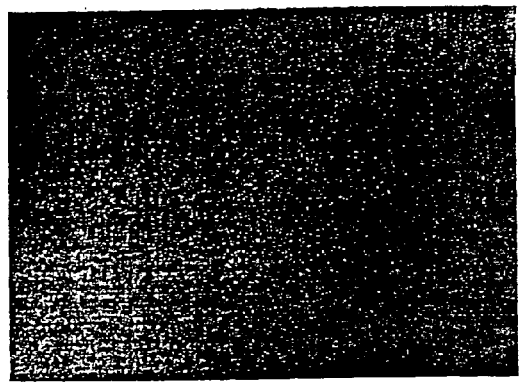
Figure 5B:
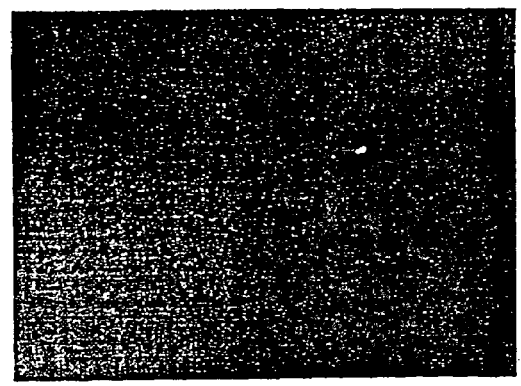
Figure 5B:
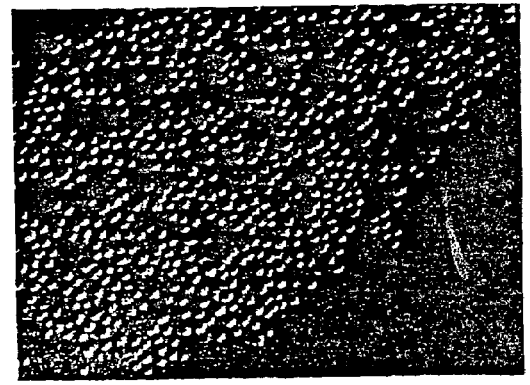
Figure 5B:
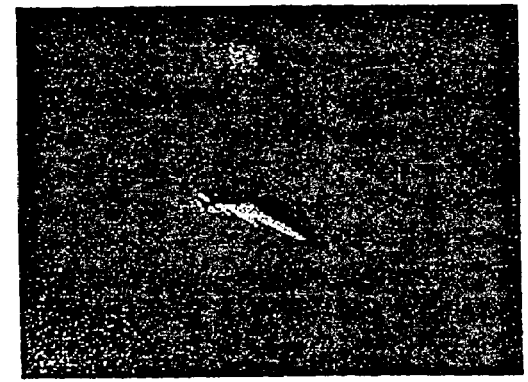

Samples (0.4 μL) of antibody solutions (10 μg/mL) for CD3, CD4, CD8, CD14, CD19 and CD56 (Coulter Beckman) are applied to a nitrocellulose film on a glass microscope slides (Molecular Probes) and maintained in a moist atmosphere in a Petrie dish. Suspensions (500 FL) of human CCRF-CEM leukemia and Raji B lymphoma cells ($10^7$ cells/mL) were applied to the arrays, incubated and washed with PBS as described in Example 2. The CCRF-CEM leukemia cells bound strongly to anti-CD4 and anti-CD8 with some binding to anti-CD3 and no binding to anti-CD19. The Raji cells only bound to anti-CD19. These results indicate that CCRF-CEM cells, for example, express high levels of CD4, intermediate levels of CD8, lower levels of CD3 and negligible levels of CD19, CD14 and CD56. Conversely, Raji cells express CD19 but not CD3, CD4, CD8, CD14 and CD56. These results, obtained using the CD antigen antibody array, were confirmed by flow cytometry (Becton Dickinson Facscalibur) using antibodies labelled with the fluorophore, FITC. These levels of expression of CD antigens are consistent with antigen expression reported for T and B cells (Bene and Martini, 1997). The results of these experiments are shown in FIGS. 5A and 5B.

EXAMPLE 6

Improved Method of Detection

The array is observed with an Olympus BX60 fluorescence microscope (Olympus Optical Company, Japan) using a UPLan 4× objective with the condensor set at the phase 1 position and a green filter over the light source. Images were captured and analyzed using a SenSys digital cooled CCD camera (1317×1035 Pixels, Photometrics), PCI Frame Grabber and Windows Image Processing and Analysis Software (Digital Optics). Images (6 antibody dots per frame) were processed for presentation using Adobe Photoshop version 3.0 software. The intensities for specific binding of cells to each antibody dot is also recorded using a relative scale of +/−, +, ++, +++.

After recording the results as computer files, the antibody arrays with bound cells are fixed by bathing the slide in FACS fixative (0.94% v/v formaldehyde, 2% D-glucose, 0.03% v/v $NaN_3$, PBS (pH 7.3)) for 30 mins. After rinsing in PBS, the bound cells are stained for 5 mins with Hemotoxylin counterstain (Immunotech, Marseille, France) which stains the nuclei of cells blue. Slides were rinsed in PBS, dried and stored at room temperature. The dried slides can be subsequently wetted with PBS and re-examined microscopically.

EXAMPLE 7

Visualization and Quantification of Cells Bound to an Antibody Array

There are several options for detecting whole cells or antigens from a blood sample bound to an antibody array.

(i) The cells or antigens are reacted with a reagent which covalently attaches fluorescent groups to amino or sulfhydryl groups on all proteins in the sample. Suitable fluorophores available as protein labelling kits are Alexa 488 and 3-(4-carboxybenzoyl)-quinoline-2-carboxaldehyde (CBQCA) which may be excited at 488 nm using an argon laser (further information on fluorophores can be found at the website of Molecular Probes). Alternatively, cells bound to an array are labelled with 5-chloromethylfluorescein diacetate (CM-FDA), a membrane-permeant probe deacetylated by intracellular esterases to form fluorescent 5-chloromethylfluorescein. This product undergoes a glutathione S-transferase$^B$ mediated reaction to produce a membrane-impermeant glutathione$^B$ fluorescent dye adduct which then reacts with thiols on proteins and peptides to form conjugates. Fluorescently-labelled cells bound to an antibody array are quantified using a scanning fluorimeter (e.g. FluorImager or Typhoon, Molecular Dynamics, Inc) or a confocal microscope. Mild reaction conditions are preferably used so that the majority of antigen binding sties are not affected. Different cells are labelled to different extents with different numbers of fluorophores. Cells are washed prior to reaction with the fluorophore.

(ii) Unlabelled cells bound to an array are reacted with soluble, fluorescently-labelled antibodies which bind to a different CD antigen on the cells enabling quantification of bound cells.

(iii) For some samples, the level of cellular CD antigen may exceed the number of antibodies available in a particular spot. CD antigens found to be expressed from an initial screen could be quantified subsequently using a row of dilutions of a particular antibody. When the number of antibodies in a spot on this array exceeded the number of CD antigens on cells applied in the sample, there is no further increase in fluorescence. A plot of fluorescence versus amount of antibody gives the density of cells expressing that CD antigen in the plasma sample. From these data, the number of a particular CD antigen per cell is calculated. Levels of bound cells on this quantitative array are determined using procedures (i) or (ii) above.

EXAMPLE 8

Detection of Fixed Cells

Bound cells on the antibody-membrane array are visualized microscopically to determine their morphologies. The cells are fixed to the array and stained, hybridized with a radioactively- or fluorescently-labelled oligonucleotide probe, treated enzymatically or tested for enzymic activities, for determination of their morphologies. The fixed cells may also be reacted with a second labelled soluble antibody (for example with a fluorochrome attached), or indeed with a number of different soluble secondary antibodies, each with a distinct fluorochrome. Expression of multiple antigens by the membrane-bound cancer cells (e.g. leukemia) on the array is then determined by fluorescence microscopy such as confocal microscopy.

In an alternative method, the fixed cells are lysed or otherwise treated to expose intracellular antigens and then reacted with a second labelled soluble antibody (for example with a fluorochrome attached) specific for an intracellular antigen, or indeed with a number of different soluble secondary antibodies, each with a distinct fluorochrome. Expression of multiple intracellular antigens by the membrane-bound cancer cells (e.g. leukemia) bound to the array is then determined by fluorescence confocal microscopy.

Fixed cells are stained or fluorescently labelled to enable quantification of cell densities in the original body fluid sample. This quantification may be automated with a programmable scanner which records cell densities at each antibody dot in the array, for different antibodies (e.g. CD, MY and/or LY). For cell mixtures containing unknown proportions of cell sub-types, densities of cells expressing a particular surface antigen are quantified by binding cells to a series of uniformly-sized antibody dots which differ in the densities of the same antibody by factors of 10-fold. The density of a particular cell sub-type is determined by densitometric or fluorimetric scanning of fixed and stained cells bound to these serially-diluted antibody dots to determine when the density of antibodies in a particular dot exceeded the density of cells in the sample of cell suspension. A second form of analysis is to run a cell suspension down a strip of a particular antibody linked to a membrane, fix and stain the bound cells, and then measure the length of the stripe of bound cells relative to the length of the total antibody stripe. The density of cells expressing a particular antigen is then calculated from the known binding capacity of antibodies in the stripe. For serially-diluted antibody dots or an antibody stripe, an internal standard is run for an antigen expressed on normal leukocytes not related to the cancer cells.

Using an array of monoclonal antibodies (e.g. against CD, MY or LY antigens), the pattern of expression of particular antigens identified by this array is matched to set patterns of antigen expression for different leukemias (e.g. M4 AML (acute myeloid leukemia): MY4(CD14), MY7, MY9, MO1 (CD11b)). The cellular morphology provides a second criterion for diagnosis. The diagnosis may be automated with fluorometric or spectrophotometric scanning of the arrays to determine which antibody spots bound cells, with computerized recognition of patterns of antigen expression for particular cancers. This method enables automated diagnosis of a wide variety of leukemias, lymphomas and other metastatic cancers. Using a complete array of antibodies against CD, MY or LY antigens, new types of leukemias and lymphomas may be discovered.

Identification of particular antigens on cancer cells provides essential information for subsequent immunotherapy of the patient with humanized monoclonal antibodies, or immunotoxins where a toxin or drug is covalently linked to the antibody. Progressive remission induced by chemotherapy and/or radiotherapy and subsequent relapse due to growth of drug-resistant cells is monitored in patients using periodic cell samples.

Other arrays of antibodies specific for antigens expressed by metastatic colon, breast, melanoma or other cancers could be made to detect very low levels of metastatic cells in body fluids (e.g. blood or cerebrospinal fluid) in patients with large primary tumors who would be at risk for metastasis. Such surveillance would be of particular importance for rapidly growing cancers such as melanomas.

A "user-friendly interface" may also be created with an antibody array by arranging antibodies which correspond to, for example, acute myeloid leukemia (AML) in the form of a character, say, "M" for this leukemia. The same antibody array could have antibodies for acute lymphocytic leukemia (ALL) arranged in an "L". In this way, a single array could give a direct diagnosis based upon known patterns of surface antigen expression for different cancers. The small size of the antibody dots and arrays of dots would enable several different tests to be performed on the same sample without significantly adding to the cost of the test. This is particularly true for 1-5 nanoliter-sized spots where each antibody would cost a small fraction of one cent.

A variety of non-neoplastic disorders of the immune system result in abnormal populations of circulating lymphocytes. Autoimmune diseases such as Type 1 diabetes, multiple sclerosis, myasthenia gravis, pernicious anaemia, psoriasis, rheumatoid arthritis, scleroderma and systemic lupus erythematosis are caused by sub-sets of T cells which may express CD4, and production of antibodies against auto-antigens by sub-sets of B cells which may express CD19. For example, quantitative abnormalities have been observed in lymphocyte populations of patients with systemic lupus erythematosis (↓ CD4+, CD45+ T lymphocytes; ↑ CD8+, CD57+ T lymphocytes). The antibody array detects expanded clones of T and B cells directed against the auto-antigen.

Children suffering from recurrent infections may have congenital immunodeficiency. Immunophenotyping by flow cytometry is used to detect deficiencies in lymphocyte sub-sets. Severe Combined Immunodeficiency Syndrome (SCIDS) is caused by a deficiency in the enzyme, adenosine deaminase, with very low levels of peripheral blood lymphocytes, such as T (CD3) and B (CD19) and Natural Killer (CD16) cells. A deficiency of purine nucleoside phosphorylase results in a deficiency of B cells. A variety of immunodeficiency disorders can be diagnosed by immunophenotyping but additional enzymic assays and karyotyping are currently required for definitive diagnosis. The antibody array of the present invention provides definitive information on the sub-sets of lymphocytes which are deficient when other criteria may not be required.

The Human Immunodeficiency Virus (HIV) infects mainly CD4+ lymphocytes because the gp120 protein of HIV binds to CD4. In the course of development of AIDS, there is irreversible depletion of CD4+ lymphocytes. However, many other cell types are infected by HIV including macrophages, B lymphocytes and microglial cells. Currently, the population of CD4 lymphocytes is monitored in patients with HIV, but immunophenotyping should be more extensive as recommended by the Centre for Disease Control (CDC, Atlanta, USA). The following double labelling tests are done by flow cytometry: negative controls, CD45/CD14, CD3/CD4, CD3/CD8, CD3/CD19, CD3/CD16, CD3/CD56 and CD4/CD8. This labour-intensive procedure is replaced by a single-step procedure using an array containing antibodies against these CD antigens and additional antigens which would further define the sub-sets of affected lymphocytes. When patients are infected with HIV, there is a rapid decline in CD4+ lymphocytes to a minimal value at approximately 6 weeks followed by a partial recovery in their levels by 12 weeks. In the longer term, there is a progressive decline in CD4+ lymphocytes leading to death after approximately 11 years (Shinton, 1998). Treatment with zidovudine (AZT) induces a transient increase in CD4+ lymphocytes; the effect of chemotherapy on various sub-sets of lymphocytes is monitored with an antibody array to follow the clinical progression of HIV patients.

Immunophenotyping is also useful for bone marrow and organ transplantation for determination of the degree of immunosuppression and complications such as rejection or infection (Bene and Martini, 1997). Flow cytometry is employed before transplantation for tissue typing using monoclonal antibodies to detect HLA-specificities, or cross-matching. Tolerance to transplanted tissues is induced by administration of cyclosporin to the patient. Treatment at the time of transplantation forces the level of peripheral blood lymphocytes to almost zero. The disappearance of T cells from the blood is monitored by flow cytometry for CD3+ cells. Following transplantation, an increase in CD8+ cells signals possible rejection and increases in CD8+ and CD16+, CD56+ and/or CD57+ cells may indicate viral infection. This surveillance of the immune state of the transplant patient is done more rapidly and extensively using an antibody array.

Some cancer patients receive high-dose chemotherapy and then require a bone marrow transplant to replace their depleted immune system. The transplanted marrow. then enables haematopoietic reconstitution but unusual subsets of lymphocytes sometimes appear, such as CD5+ T cells. Opportunistic infections and graft-versus-host disease may occur in such patients giving an increase in CD8+ cells in both cases and on elevation of Natural Killer cells. Replacement of flow cytometry with an antibody array for CD antigens simplifies the monitoring of patients and provides more extensive information.

Antibody arrays for CD antigens are also useful for monitoring changes in lymphocyte sub-sets during desensitisation therapy to insect or spider venom where the numbers of CD4+CD45RA+ increase and CD4+ CD45RO+ decrease from elevated levels. Patients with Chronic Fatigue Syndrome may have immunological abnormalities consistent with a viral infection with activated CD8+ lymphocytes. A detailed analysis of lymphocyte sub-sets by the antibody array of the present invention establishes new diagnostic criteria and provides fundamental information on this disorder.

EXAMPLE 9

Antibody Array to Diagnose Leukemias

CCRF-CEM T cell leukemia and Raji B cell lymphoma are distinguishable using an array of antibodies against CD3, 4, 8, 14, 19 and 56 bound to a microscope slide. The distinguishing array appears as follows (where "+" indicates level of binding):

|  | CEM | Raji |
|---|---|---|
| CD3 | + | − |
| CD4 | +++++ | − |
| CD8 | ++ | − |
| CD14 | − | − |
| CD19 | − | ++++ |
| CD56 | − | − |

This array is tested with whole blood and peripheral blood lymphocytes. All spots bind cells with different sub-populations of cells on some of the spots. Sub-populations of cells are detected using antibodies against the following CD antigens:

CD2, 7, 3, 4, 5, 8, 9, 10, 11b, 11c, 13, 14, 15, 16, 19, 20, 21, 22, 23, 24, 25, 33, 34, 36, 37, 38, 41, 42, 45, 56, 57, 95, 122.

Large arrays are set up with these antibodies to investigate the binding properties of leukemia cells taken from patients. A particular focus is upon patients with AML, CLL and ALL but the present invention covers any cancer. By using this approach, the antibody array is capable of defining new subsets of leukemias based upon extensive information on antigen expression available using this single step assay.

EXAMPLE 10

Nitrocellulose-Based Antibody Array

Figure 4:
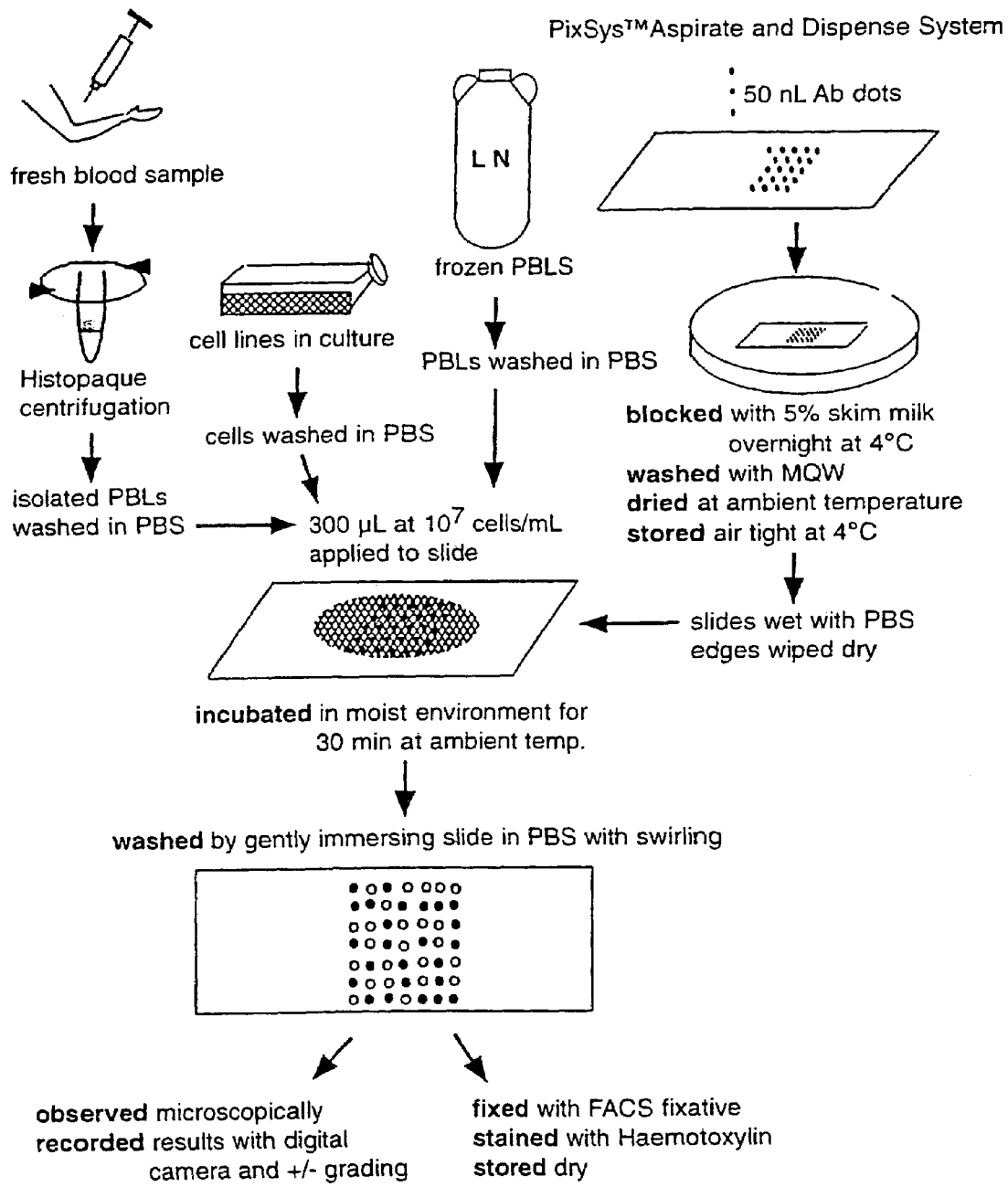
FIG. 4 is a diagrammatic representation showing an antibody array procedure.

The procedures used to prepare the assay are illustrated as a flow chart in FIG. 4. The antibody arrays are constructed using a Biodot Aspirate and Dispense System (Cartesian Technologies) where 5 nL dots are applied to a nitrocellulose film on glass microscope slides (Schleicher and Schuell, Cat. No. 10484182). Purified monoclonal antibodies (Beckman Coulter, Becton Dickinson or Biosource International) are used at concentrations recommended for flow cytometric analysis and are applied in the same buffers as supplied by the manufacturers. The nitrocellulose is then blocked by incubation with 5% w/v skim milk (Dutch Jug) for 1.5 h at 37° C. These blocking conditions are chosen to minimize background binding.

The dry arrays are stored for more than 3 months at 4° C. with no loss of binding capacity for human CCRF-CEM T-cell leukemia and Raji B-cell lymphoma cell lines (Tables 1 & 2). A comparison of dry arrays stored with desiccant at 4° C., room temperature (22° C.) or 37° C. for 1 month showed little or no deterioration at 4° C., minimal deterioration at room temperature and only partial loss of binding activity at 37° C. when tested with normal PBLs (Table 3). Shaded antibodies continued to show strong binding activity even after 1 month at 37° C. The stability of the arrays is further enhanced by adding protein stabilizing agents to the antibodies (e.g. polyethylene glycol or stabilizer products commercially available from Surmodics, Minn., USA).

Normal leukocytes or leukemia cells are prepared by Histopaque centrifugation and are washed and resuspended to $10^7$ cells/L in phosphate-buffered saline (PBS). The use of PBS results in cells which are metabolically depleted and results in reduced non-specific background binding to blocked antibody arrays. The cell suspensions are applied to the array and incubated at room temperature for 30 min, fixed with a glucose/formaldehyde/PBS solution and then washed with PBS. Cells bound to the array are photographed and the digital images are matched to consensus patterns for normal PBLs or leukemias. Since some of the samples show background binding to the nitrocellulose, steps are taken to minimise the background. Inclusion of the chelating agent 1 mM EDTA in the PBS for cell suspension significantly reduces background binding without interfering with specific antibody binding. An AML sample is found to bind very strongly to isotype control antibodies, suggesting Fc receptor binding. This is overcome by pre-incubation of the cells with 10% v/v heat inactivated human AB serum. To further reduce the problem of background binding, the following compounds are used to reduce the binding capacity of leukocytes by inhibiting protein synthesis and/or by blocking the Mac-1 adhesion molecule expressed on many activated leukocytes: heparin, high molecular weight kininogen, Mocimycin, pentoxifylline, benzydamine (Tantum), lidocaine and naftifine.

Figure 6:
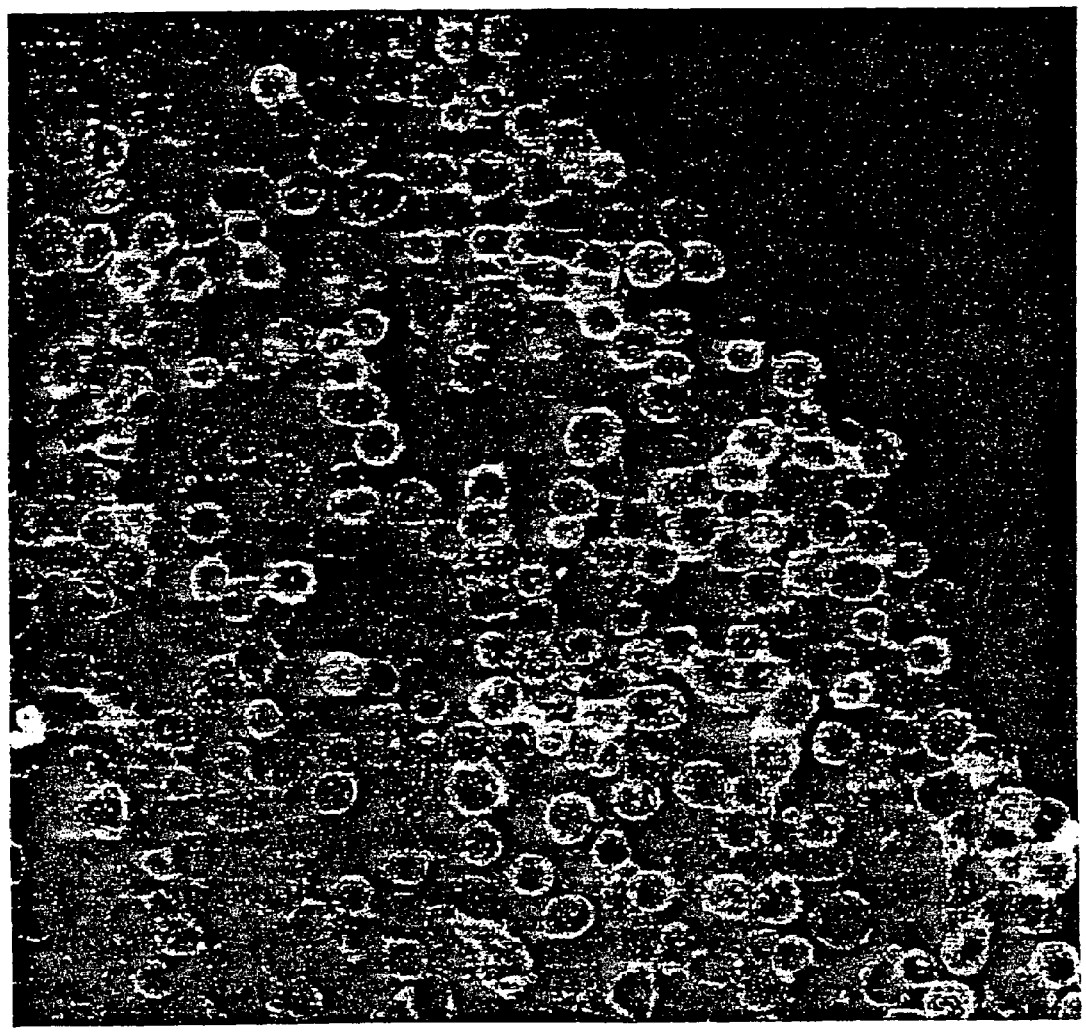
FIG. 6 is a photographic representation of CCRF-CEM cells bound to a CD4 antibody dot and labelled with Alexa-488 conjugated CD45 antibody.

Wet slides are reviewed using dark-field microscopy at 400× magnification. Dots are photographed in groups of 6 and a composite picture produced using Adobe Photoshop software. Cell density on each antibody dot is quantified from the digital images using computer software or recorded by densitometric or fluorimetric scanning. The leukocytes bound on the array are stained by Alexa 488-conjugated anti-CD45 (leukocyte common antigen) and observed by fluorescence microscopy (FIG. 6). Three colour confocal microscopy is thus used for further identification and characterisation of cells bound to individual antibody dots. Histochemical stains (e.g. myeloperoxidase) is used on the cells bound to the arrays to confirm identification of some leukemia sub-types (e.g. AML).

Figure 7B:
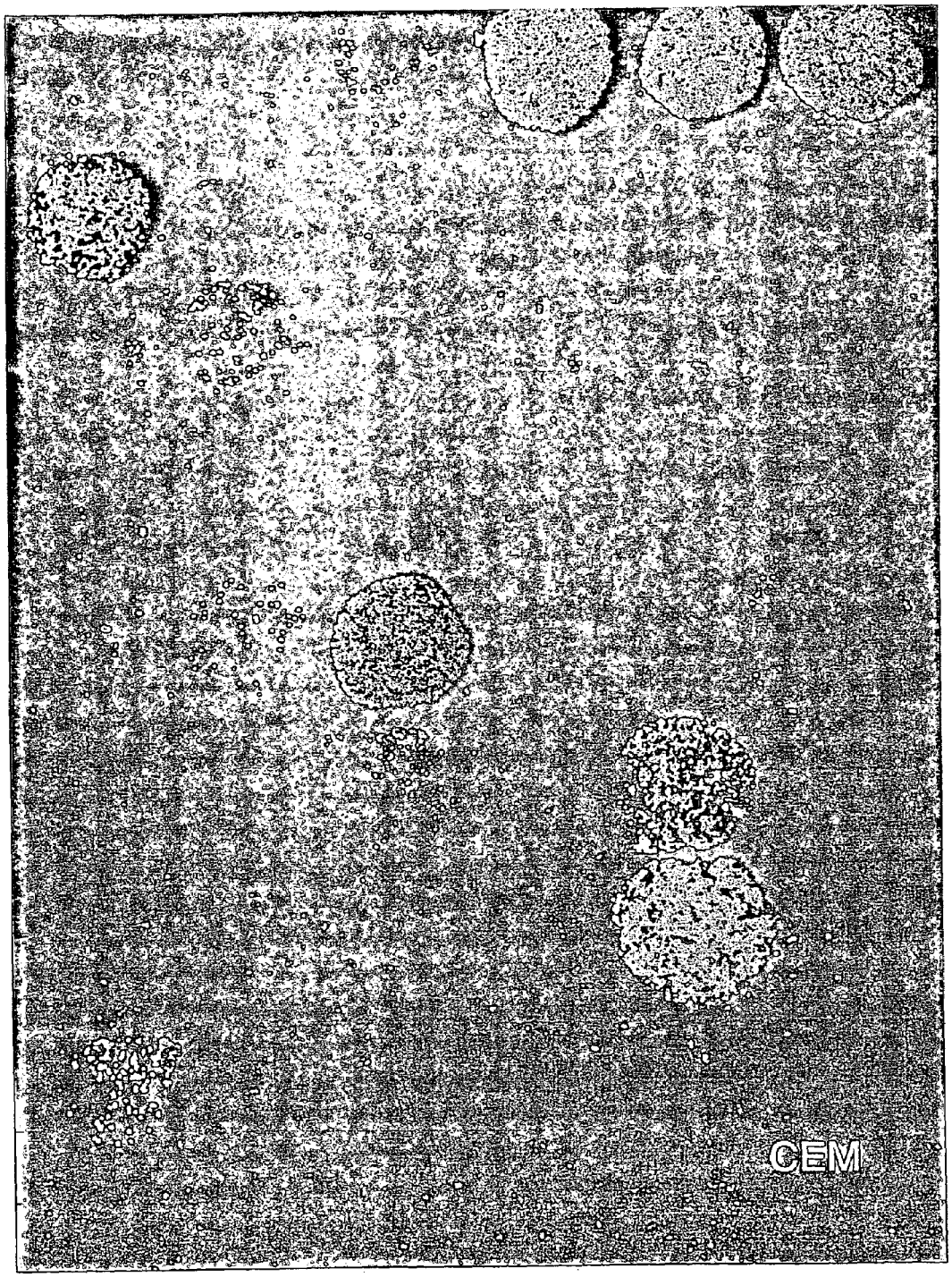
FIG. 7 is a representation of antibody arrays tested with cell lines. (a) tabulated key for the position of antibody dots in the array; (b) CCRF-CEM T-cell leukemia; (c) Raji B-cell lymphoma; (d) NB4 myeloid cells. Cells were suspended in PBS. MIgG1, mIgG2a, b mIgM are isotype control antibodies. The numbers denote antibodies to the relevant CD molecule (eg. 2 denotes anti-CD2). GPA is anti-glycophorin A, a marker on human red blood cells; HLA-DR is anti-HLA-DR class II; KOR is an antibody to granulocyte KOR-SA3544 antigen; FMC7 is an antibody to a marker which distinguishes various B cell leukemias.
Figure 7C:
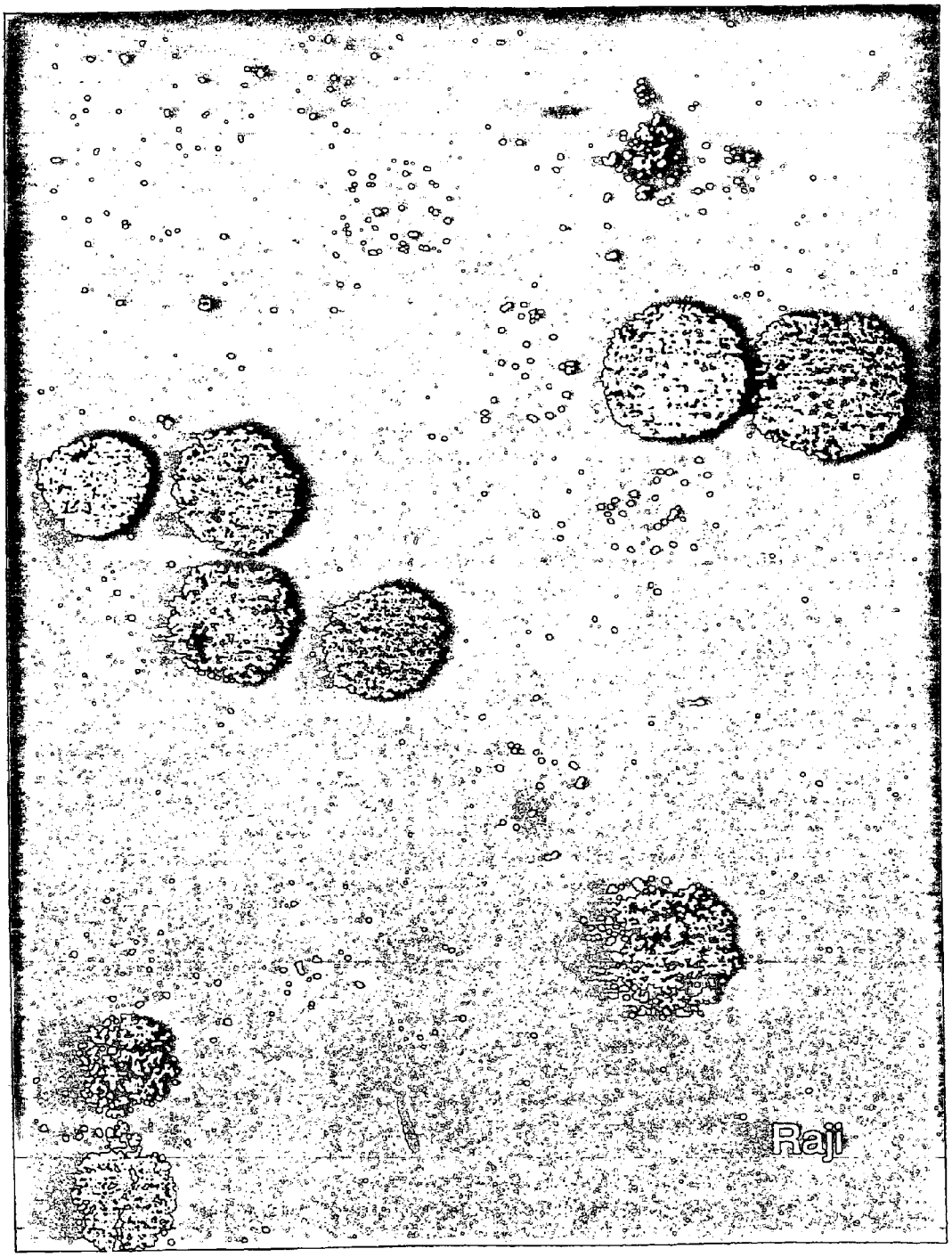
Figure 7D:
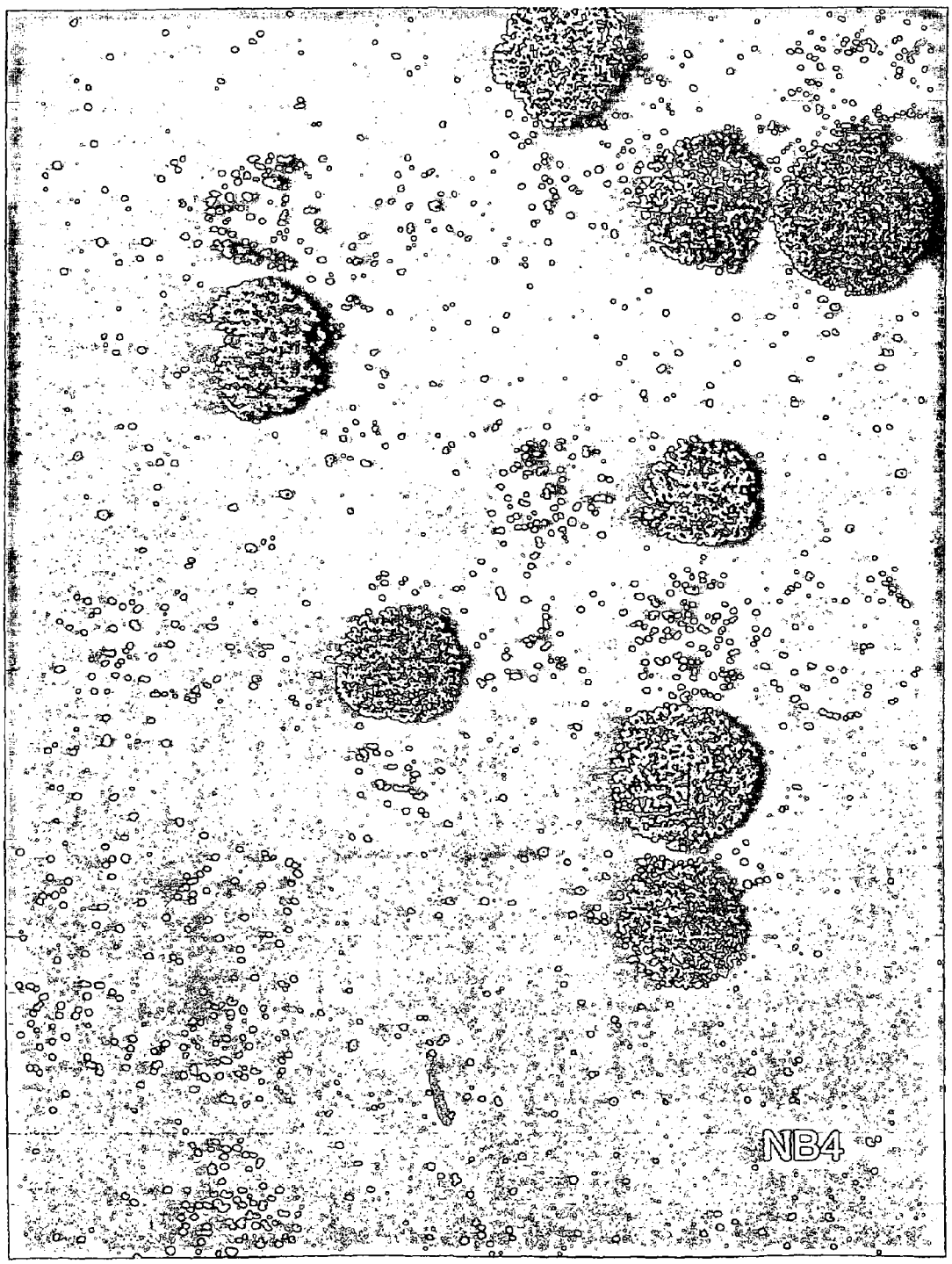

Initially, 3 cell lines are tested on an array of 54 10 nL antibody dots (FIGS. 7a-d). The key for the positions of antibodies is shown in FIG. 7a. Distinct dot patterns are detected with the CCRF-CEM T-cell leukemia (FIG. 7b), Raji B-cell lymphoma (FIG. 7c) and the NB4 myeloid cell lines (FIG. 7D). These results are summarized in Table 4.

Figure 8B:
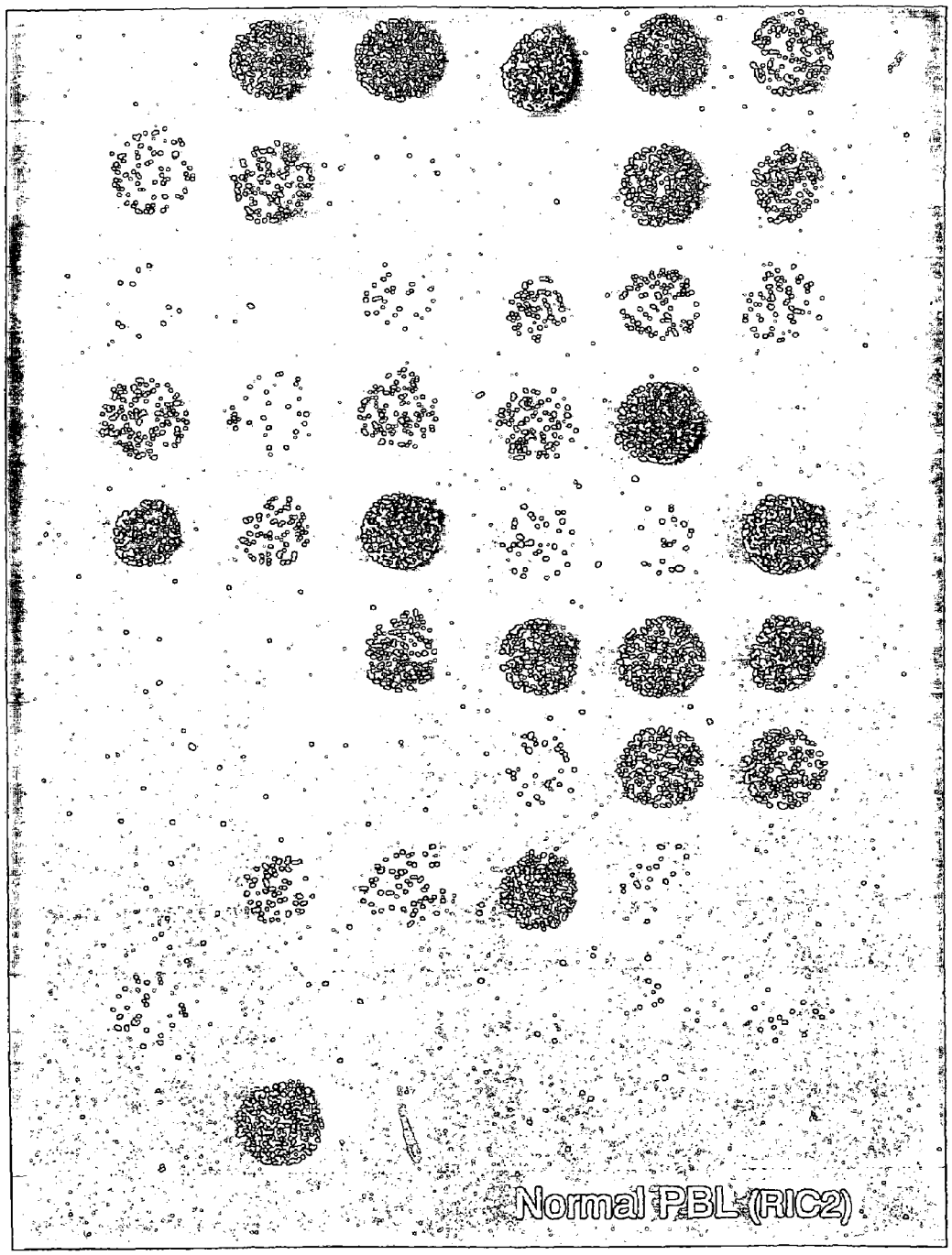
FIG. 8 is a photographic representation of antibody arrays tested with leukocytes purified from peripheral blood showing (a) a key for the position of antibody dots in the array; (b) normal PBL RIC2; (c) CLL patient KB (WBC count 10×10$^9$ cells/ml); (d) CLL patient EH2 (WBC count 30×10$^9$ cells/ml); (e) HCL patient RD; (f) AML patient GT; (g) B-cell lymphoma (BCL) patient KR. Cells were bound to arrays in PBS with EDTA and 10% v/v human AB serum. All results are from frozen cell samples.
Figure 8C:
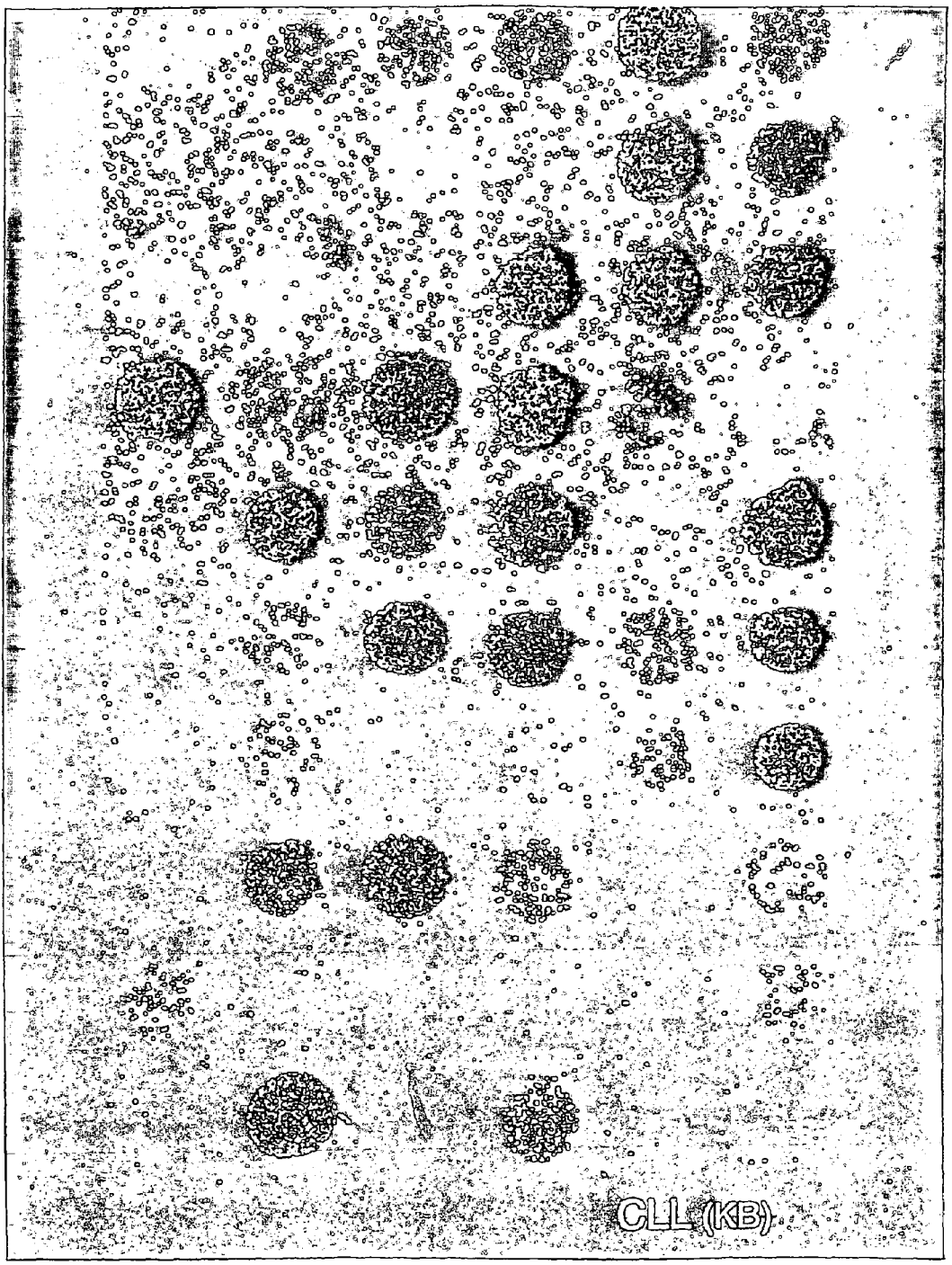
Figure 8D:
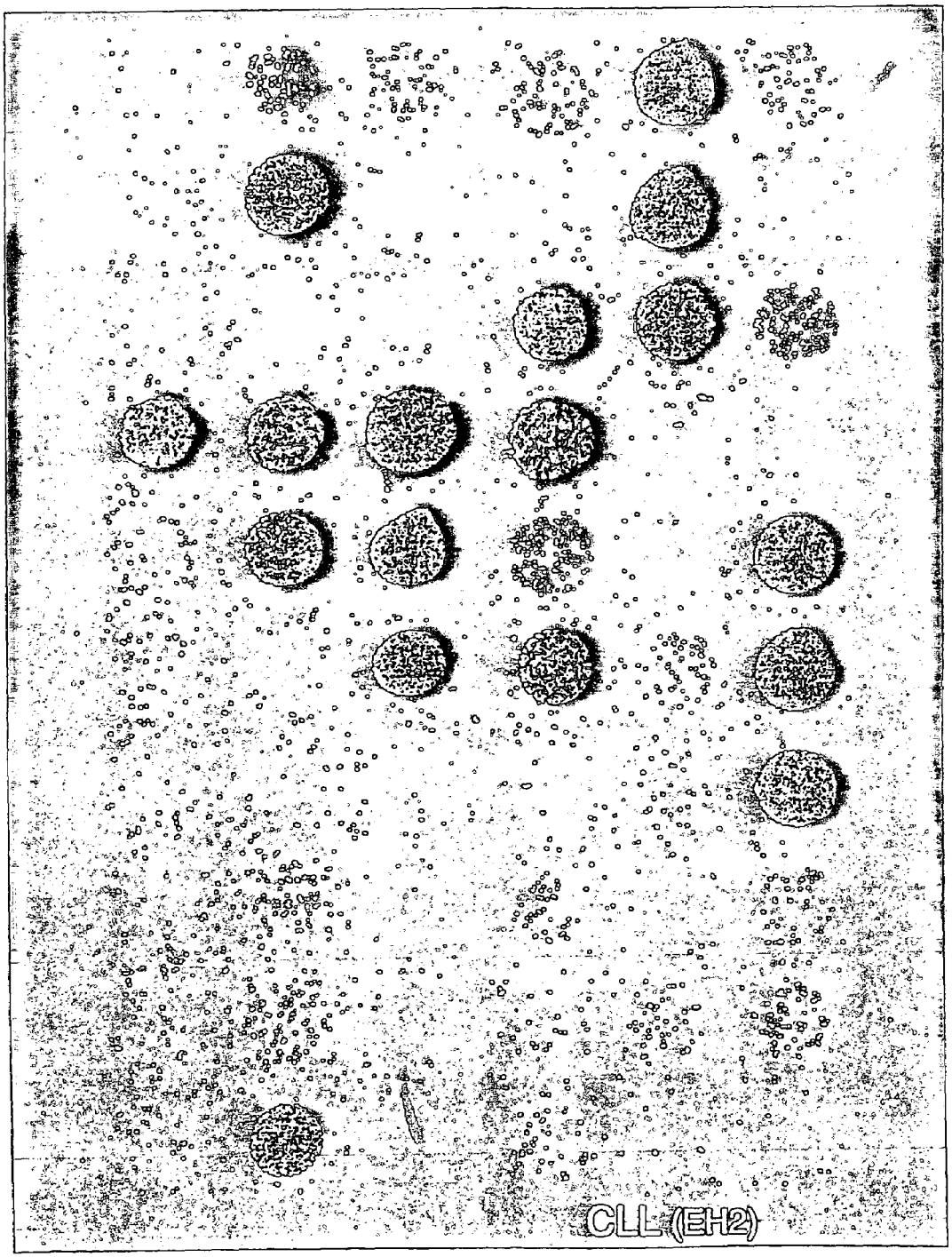
Figure 8E:
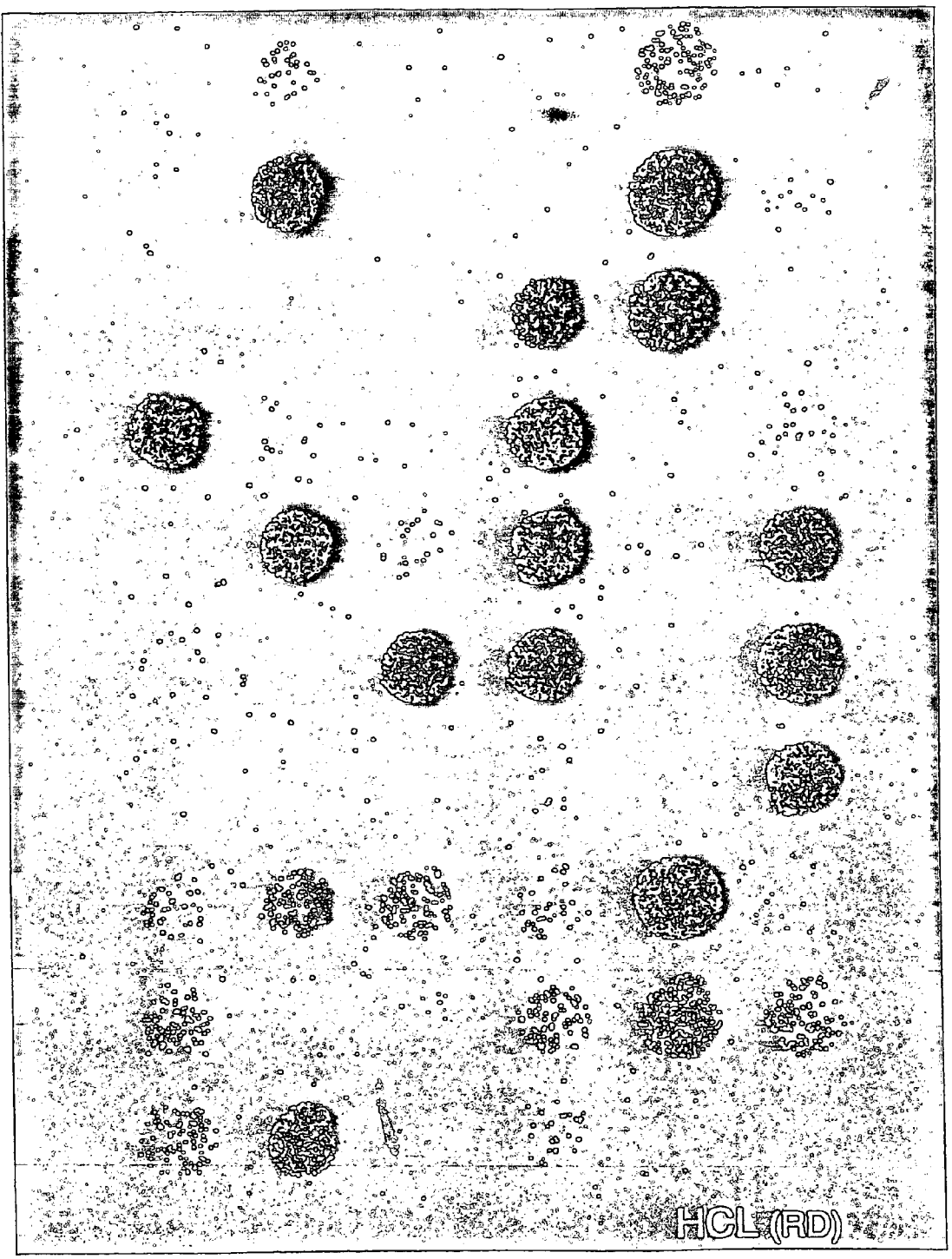
Figure 8F:
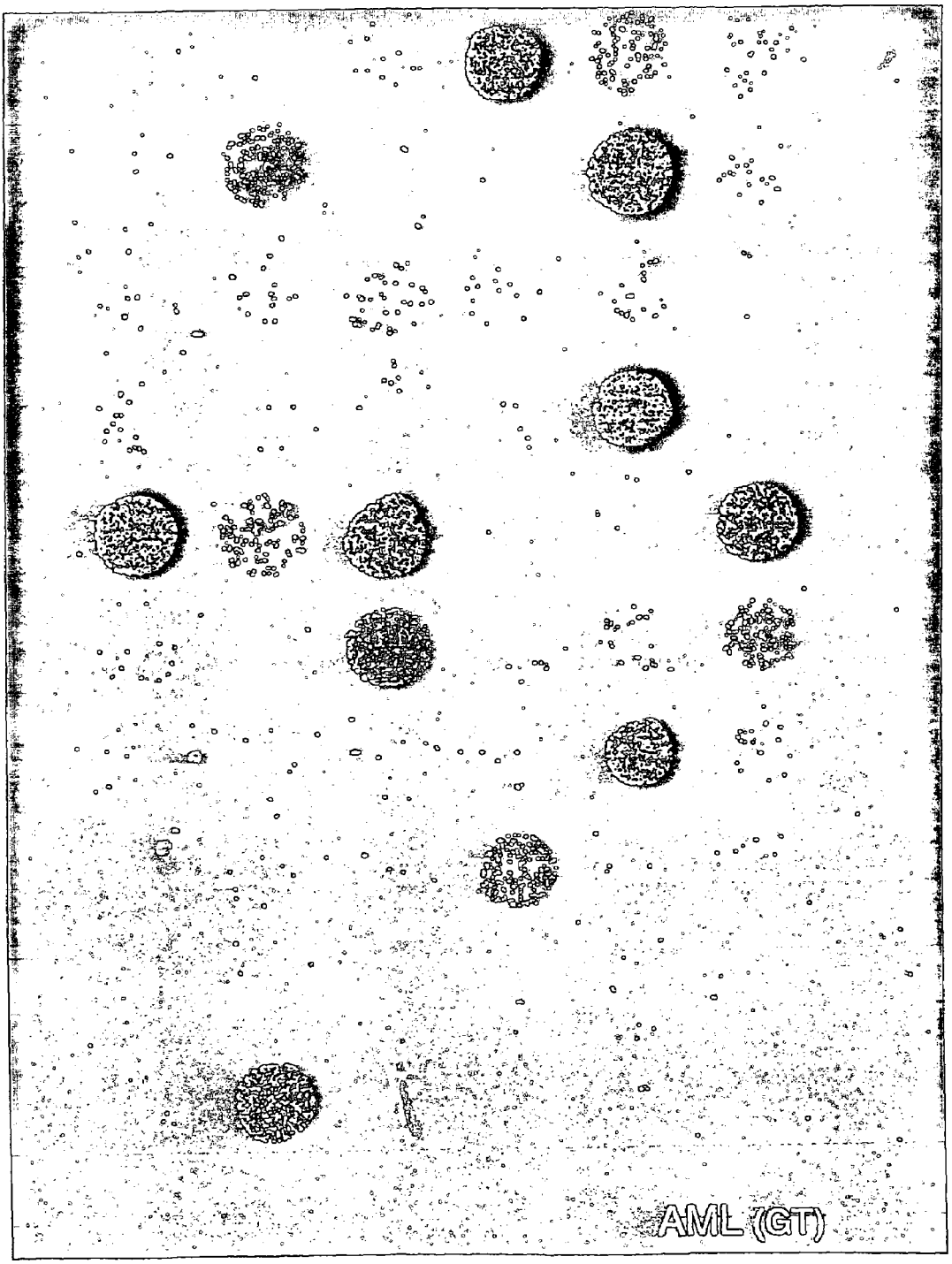
Figure 8G:
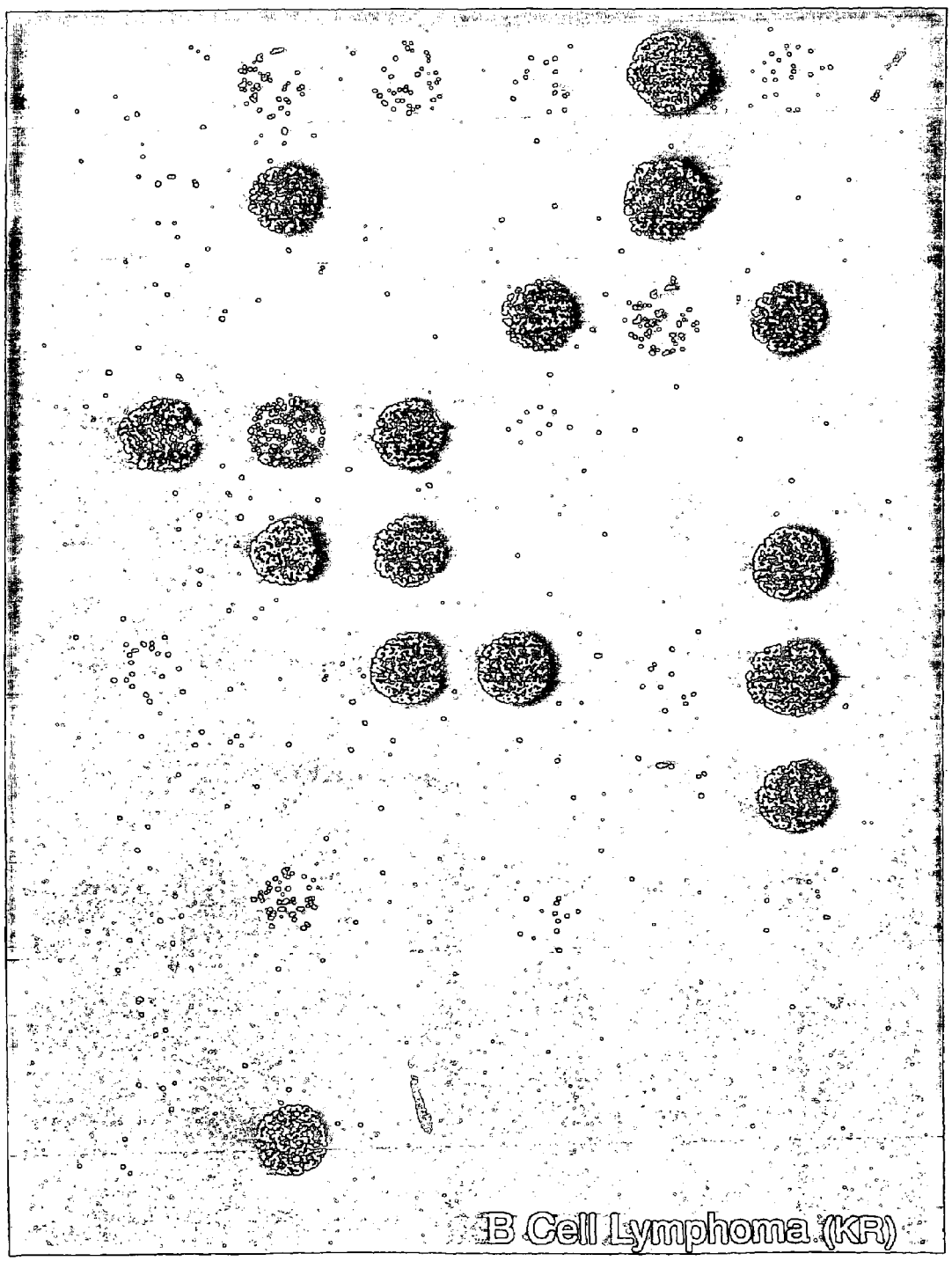

Typical dot patterns for normal PBLs, Chronic Lymphocytic Leukemia (CLL), Hairy Cell Leukemia (HCL), Acute Myeloid Leukemia (AML) and B-cell Lymphoma (BCL) are shown in FIGS. 8a-g with the key for the positions of antibodies (FIG. 8a). Patterns of CD antigen expression for PBLs are summarized in Table 5, with the shaded CD antigens indicating a common pattern of expression. Freshly isolated PBLs (RIC) give similar results to the same PBLs which had been frozen in liquid nitrogen and then thawed (shown in Table 8). This observation enables the use of frozen leukocytes and leukemias for analysis with antibody arrays. Table 6 summarizes patterns of CD antigen expression for CLL cells from 9 leukemia patients. When CLL samples are frozen and retested, the patterns obtained are highly reproducible. All tested CLLs strongly expressed CD5, 11c, 19, 20, 21, 22, 23, 24, 37, 38, 45, 52 and HLA-DR, which are characteristic cell surface markers for CLLs of the B-cell type.

Table 7 shows a comparison between a normal PBL, two CLLs and samples from PLL (prolymphocytic leukemia), HCL, BCL and AML patients. CLL sample KB is from an early diagnosis with WBC density within the range for normal individuals ($10 \times 10^9$ cells/L), while the EH2 sample came from a patient with more advanced disease and a raised WBC count of $30 \times 10^9$ cells/L. The shading illustrates the similarities and differences in the major antigens expressed by these different leukemias.

A rigorous comparison is made between analysis of PBLs and CLLs using the antibody array and flow cytometry (Table 8). There is a strong correlation between the results from the two analyses, with the exceptions of CD2, CD11b, 14, 15, 16, 56, 57, 95, 103, 154, KOR and FMC7. In most of these cases, flow cytometry is positive, while the antibody array is negative. Also, the percentage of positive cells detected by flow cytometry is low or the staining is weak. Flow cytometry uses soluble antibodies while arrays use antibodies immobilized on a solid support. Antibodies in free solution have greater access to CD antigens on cells than antibodies on an array where steric hindrance may occur. Also, a higher affinity of binding is required to retain cells bound to a solid phase. Storage of antibodies in solution at $4^EC$ results in a gradual loss of binding activity on subsequent antibody arrays. In most cases, binding activity is restored with fresh antibody. In other cases, higher concentrations of antibody are required. In one case (CD2), antibody from a different hybridoma clone binds cells. These modifications significantly improve the correlation between solid phase and FACS analysis.

Where CD expression is negative by flow cytometry, but positive by antibody array (ie. CD103 and KOR with RIC PBL), this difference is resolved by inclusion of human AB serum with RIC PBLs before testing by antibody array; both CD103 and KOR were then negative (see FIG. 8b). Inclusion of human AB serum, which contains immunoglobulins, also blocked detection of immunoglobulin (Ig) on the surface of B-cell CLLs. In addition, human serum may contain soluble forms of other cell surface markers which may block the binding cells expression these markers (eg. CD154, CD95). It is recommend that samples be tested initially in EDTA/PBS without addition of human AB serum. Only those samples which show strong Fc receptor binding in the initial test are then retested with human AB serum.

Figure 9:
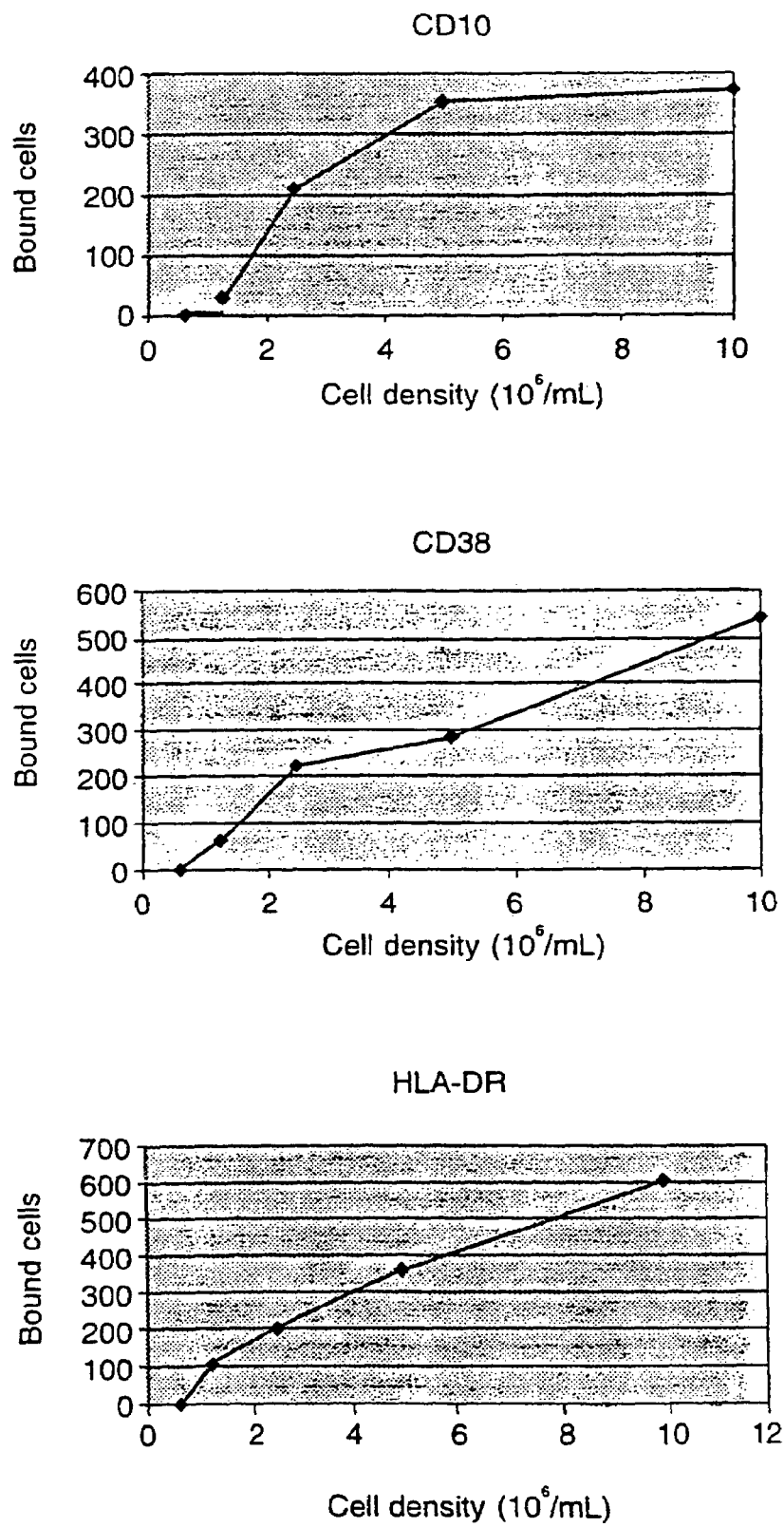
FIG. 9 is a graphical representation showing the relationship between Raji cell density and the number of cells bound to antibody cell dots.
Figure 10:
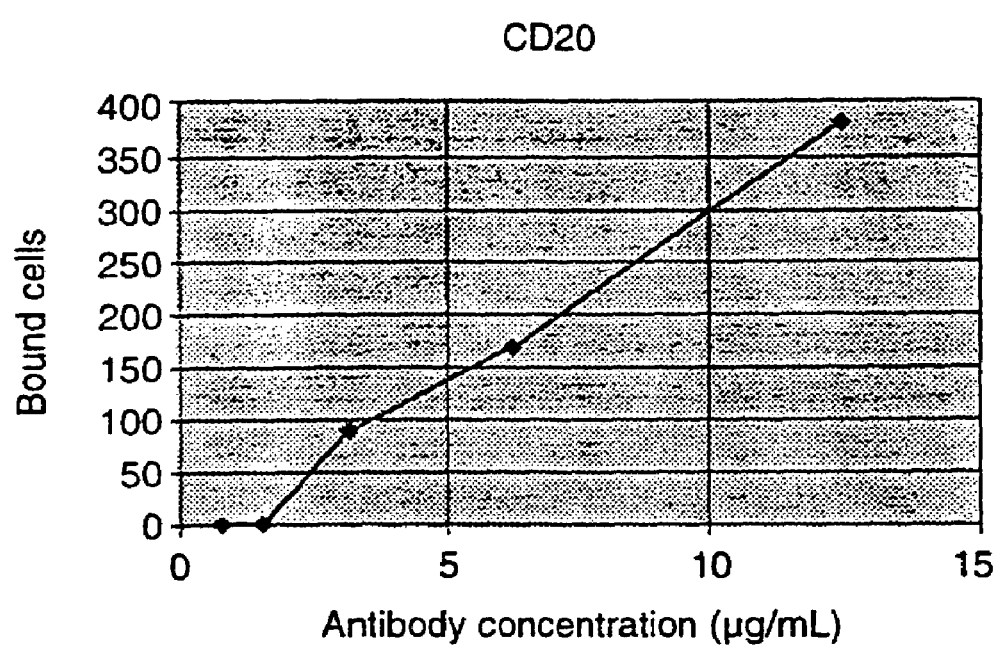
FIG. 10 is a graphical representation showing the relationship between antibody concentration and the number of Raji cells bound to antibody dots.

For some applications, cell binding to the antibody dots is quantified by comparison with an internal standard. FIG. 9 shows the relationship between cell binding and the density of Raji cells incubated with dots of antibodies against 3 different surface markers. For CD38 and HLA-DR, there is a direct correlation between cell density and number of cells bound to the dot at cell concentrations up to $10 \times 10^6$ cells/nL. For HLA-DR, the correlation is linear from $1-10 \times 10^6$ cells/mL. For CD10, a plateau was reached at approximately $5 \times 10^6$ cells/mL, suggesting saturation of antibody binding sites. FIG. 10 shows that correlation between cell binding and CD10 antibody concentration was linear at antibody concentrations between 0.16 and 1.25 µg/ml. These results demonstrate that quantification of cell binding should be possible provided conditions are optimized for each antibody.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The assay of the present invention is referred to as the "LD Array" and is dedicated to a patient, Mrs Lee Dixon, who had acute myeloid leukemia (AML, M4).

TABLE LEGENDS

Table 1: Stability of Antibody Array for Binding of CCRF-CEM Cells

Antibody arrays were dried at room temperature, blocked, washed in water, dried then stored at 4° C., wrapped in cling-wrap in an air-tight plastic bag. Results were recorded as — (no binding), +/− (a few cells), + (weak positive), ++ (strong positive), +++ (cells entirely cover antibody dot), ++++ (thick coverage of antibody dot).

Table 2: Stability of Antibody Array for Binding of Raji Cells
Experimental procedure as for Table 1. (b/g results obscured by background binding of cells to nitrocellulose).

Table 3: Binding Patterns for PBLs on Arrays Stored at 4° C., 22° C. and 37° C.
PBL (RIC2) stored in liquid nitrogen were reconstituted and bound to the arrays in PBS containing EDTA and human AB serum by the established procedure. Shaded CD markers indicate strong binding after storage for 1 month at all 3 temperatures.

Table 4: Binding Patterns for Cell Lines on Antibody Arrays.
Cultured cells resuspended in PBS were bound to arrays as for Table 3. Shaded CD markers indicate strong binding.

Table 5: Binding Patterns for PBLs on Antibody Arrays.
PBLs from two subjects (RIC and LB) and three buffy coats from the Red Cross Blook Bank (PBL1, 2, 3) were bound to arrays as for Table 3. All procedures were as for Table 3.

Table 6: Binding Patterns for Chronic Lymphocytic Leukemia Samples from 9 Patients.
All procedures were as for Table 3, but samples were tested in PBS, except EH2, KB and NH to which EDTA and human AB serum were added. Shaded CD markers indicate consistent binding for all patients.

Table 7: Binding Patterns for PBL, CLL, PLL, HCL, BCL and AML Samples.
All procedures were as for Table 3. Shaded CD markers indicate strong binding.

Table 8: Comparison of FACS Analysis and Antibody Array Results for Fresh and Frozen PBLs and for Two Different CLL Samples.
Antibody array procedures were as for Table 3, except no human serum or EDTA was added. FACS analysis was routinely carried out on cells with 10% human AB serum. Shaded areas highlight the differences between the two methods.

TABLE 1

Stability of antibody array for binding of CCRF-CEM cells

| CD Marker | Initial | 3 days | 1 week | 2 weeks | 7 weeks | 3 months |
|---|---|---|---|---|---|---|
| 2 | +/− | +/− | +/− | − | + | +/− |
| 3 | +/− | + | +/− | +/− | +/− | − |
| 4 | +++ | +++ | +++ | +++ | +++ | +++ |
| 5 | + | +++ | +++ | +++ | +++ | +++ |
| 8 | − | ++ | + | +/− | + | ++ |
| 95 | +++ | +++ | +++ | +++ | +++ | +++ |
| 103 | − | − | − | − | − | − |
| HLA-DR | − | − | − | − | − | − |

TABLE 2

Stability of antibody array for binding of Raji cells

| CD marker | Initial | 3 days | 1 week | 2 weeks | 7 weeks | 3 months |
|---|---|---|---|---|---|---|
| 10 | ++ | ++ | ++ | +++ | +++ | +++ |
| 19 | +++ | +++ | ++ | +++ | +++ | +++ |
| 20 | b/g | + | +/− | + | +++ | ++ |
| 21 | b/g | +++ | +++ | +++ | +++ | +++ |
| 22 | +++ | +++ | +++ | +++ | +++ | +++ |
| 23 | ++ | ++ | ++ | ++ | ++ | +++ |
| 25 | +/− | +/− | +/− | +/− | +/− | +/− |
| 37 | +++ | +++ | +++ | +++ | +++ | +++ |
| 45 | ++ | ++ | +/− | ++ | ++ | ++ |
| 95 | +++ | +++ | +++ | +++ | +++ | +++ |
| HLA-DR | +++ | +++ | ++ | +++ | +++ | +++ |

TABLE 3

Binding patterns for PBLs on arrays stored dry at 4°, 22° and 37° C.

| CD marker | Day 1 4° C. | after 1 month storage 4° C. | 22° C. | 37° C. |
|---|---|---|---|---|
| mIgG1 | − | − | − | − |
| 2 | ++ | ++ | ++ | ++ |
| 3 | ++ | ++ | ++ | +/− |
| 4 | ++ | ++ | ++ | ++ |

TABLE 3-continued

Binding patterns for PBLs on arrays stored dry at 4°, 22° and 37° C.

| CD marker | Day 1 4° C. | after 1 month storage 4° C. | 22° C. | 37° C. |
|---|---|---|---|---|
| 5 | + | + | ++ | +/− |
| 7 | ++ | ++ | ++ | + |
| 8 | + | + | + | +/− |
| 9 | + | + | + | − |
| 10 | − | − | − | − |
| 11b | +/− | +/− | +/− | − |
| 11c | ++ | ++ | ++ | ++ |
| 13 | + | + | +/− | − |
| 14 | − | − | − | − |
| 15 | − | − | − | − |
| 16 | + | +/− | − | − |
| 19 | +/− | + | + | +/− |
| 20 | + | + | +/− | +/− |
| 21 | +/− | + | + | + |
| 22 | + | + | + | +/− |
| 23 | +/− | +/− | +/− | +/− |
| 24 | +/− | + | + | +/− |
| 25 | ++ | + | + | +/− |
| 33 | ++ | +/− | ++ | ++ |
| 34 | − | − | − | − |
| 36 | +++ | +++ | +++ | +++ |
| 37 | + | + | + | + |
| 38 | ++ | ++ | ++ | ++ |
| 41 | +/− | +/− | +/− | +/− |
| 42a | + | +/− | +/− | +/− |
| 45 | + | + | − | +/− |
| 45RA | + | + | +/− | +/− |
| 45RO | ++ | ++ | + | + |
| 52 | ++ | ++ | + | ++ |
| 56 | − | − | − | − |
| 57 | − | − | − | − |
| 60 | − | − | − | − |
| 61 | +/− | +/− | +/− | +/− |
| 71 | +/− | +/− | +/− | +/− |
| 79a | − | + | − | − |
| 95 | +/− | + | +/− | − |
| 103 | − | − | − | − |
| 117 | − | − | − | − |
| 122 | +/− | + | +/− | +/− |
| 154 | − | − | − | − |
| GPA | − | − | − | − |
| HLA-DR | ++ | ++ | ++ | ++ |
| KOR | − | − | − | − |
| FMC7 | +/− | + | − | − |

TABLE 4

Binding patterns for cell lines on antibody arrays.

| Antibody | CEM | Raji | NB4 |
|---|---|---|---|
| mIgG1 | − | − | − |
| mIgG2a | − | − | − |
| mIgG2b | − | − | − |
| mIgM | − | − | − |
| 2 | +/− | − | − |
| 3 | +/− | − | − |
| 4 | ++++ | − | +++ |
| 5 | ++++ | − | − |
| 7 | ++++ | − | + |
| 8 | +++ | − | − |
| 9 | − | − | + |
| 10 | − | +++ | +/− |
| 11b | − | − | +/− |
| 11c | − | − | ++ |
| 13 | − | − | +++ |
| 14 | − | − | − |
| 15 | + | − | ++ |
| 16 | − | − | − |
| 19 | − | +++ | − |
| 20 | − | ++++ | − |
| 21 | − | +++ | − |
| 22 | − | ++++ | − |
| 23 | − | ++++ | − |
| 24 | − | − | − |
| 25 | − | − | + |
| 33 | − | − | ++ |
| 34 | − | − | − |
| 36 | − | − | +/− |
| 37 | +/− | ++++ | − |
| 38 | ++++ | +++ | +++ |
| 41 | − | − | +/− |
| 42a | − | − | + |
| 45 | ++ | ++ | ++ |
| 45RA | − | +++ | − |
| 45RO | ++ | − | +++ |
| 52 | − | − | − |
| 56 | − | − | +/− |
| 57 | − | − | +/− |
| 60 | − | − | − |
| 61 | − | − | − |
| 71 | ++++ | ++ | +++ |
| 79a | − | − | − |
| 95 | + | ++ | +/− |
| 103 | − | − | + |
| 117 | − | − | − |
| 122 | − | − | − |
| 154 | − | − | − |
| GPA | − | − | − |
| HLA-DR | − | +++ | − |
| KOR | − | − | + |
| FMC7 | − | − | − |

TABLE 5

Binding patterns for PBLs on antibody arrays

| Marker | Normal PBLs | | | | |
|---|---|---|---|---|---|
| | RIC | PBL1 | PBL2 | PBL3 | LB |
| mIgG1 | − | − | − | − | − |
| 2 | +++ | − | +/− | + | − |
| 3 | +++ | +++ | +++ | +++ | +++ |
| 4 | +++ | +++ | +++ | +++ | ++++ |
| 5 | +++ | +++ | +++ | +++ | ++++ |
| 7 | ++ | ++ | ++ | ++ | +++ |
| 8 | + | + | ++ | − | +++ |
| 9 | ++ | − | + | +++ | ++ |
| 10 | − | − | + | + | − |
| 11b | − | − | − | − | − |
| 11c | ++ | ++ | ++ | ++ | +++ |
| 13 | + | ++ | + | + | − |
| 14 | − | − | +/− | +/− | − |
| 15 | − | − | − | − | − |
| 16 | − | − | +/− | +/− | − |
| 19 | + | + | + | +/− | + |
| 20 | + | + | + | + | + |
| 21 | + | + | + | + | + |
| 22 | ++ | +++ | ++ | ++ | − |
| 23 | +/− | + | + | +/− | + |
| 24 | +/− | + | +/− | +/− | + |
| 25 | ++ | ++ | +++ | +++ | ++ |
| 33 | ++ | ++ | +++ | +++ | +++ |
| 34 | − | − | − | − | − |
| 36 | ++ | ++ | +++ | +++ | ++++ |
| 37 | + | − | ++ | + | + |
| 38 | ++ | ++ | +++ | +++ | ++++ |
| 41 | ++ | + | +++ | + | +/− |
| 42a | ++ | ++ | + | ++ | + |
| 45 | ++ | +++ | +++ | + | ++++ |
| 45RA | ++ | + | +++ | +/− | + |

TABLE 5-continued

Binding patterns for PBLs on antibody arrays

Normal PBLs

| Marker | RIC | PBL1 | PBL2 | PBL3 | LB |
|---|---|---|---|---|---|
| 45RO | ++ | ++ | ++ | +++ | ++++ |
| 52 | +++ | − | ++ | − | − |
| 56 | − | − | − | − | − |
| 57 | − | − | − | − | − |
| 60 | − | − | − | − | − |
| 61 | + | − | − | − | + |
| 71 | − | +/− | +/− | +/− | +/− |
| 79a | − | +/− | +/− | − | − |
| 95 | + | +/− | +/− | − | ++ |
| 103 | ++ | ++ | ++ | + | − |
| 117 | − | − | − | − | − |
| 122 | + | + | − | − | +/− |
| 154 | − | +/− | + | − | − |
| GPA | − | +/− | +/− | − | − |
| HLA-DR | +++ | nd | nd | nd | + |
| KOR | +++ | ++ | + | ++ | +/− |
| FMC7 | − | − | − | − | − |
| anti-hIg | nd | nd | nd | nd | − | nd not done

TABLE 6

Binding patterns for Chronic Lymphocytic Leukaemia samples from 9 patients

CLL

| Marker | AW | YI | FS | PN | PL | DD | EH2 | KB | NH |
|---|---|---|---|---|---|---|---|---|---|
| mIgG1 | − | − | − | − | − | − | − | − | − |
| 2 | − | − | − | − | − | − | ++ | ++ | ++ |
| 3 | − | − | − | − | − | − | + | + | +++ |
| 4 | − | − | − | − | − | − | + | + | ++ |
| 5 | +++ | +++ | +++ | +++ | ++++ | ++++ | ++++ | +++ | +++ |
| 7 | nd | nd | nd | − | − | − | + | + | ++ |
| 8 | − | − | − | − | − | +/− | +/− | − | ++ |
| 9 | +++ | − | +++ | − | +/− | ++ | ++++ | − | + |
| 10 | − | − | − | − | − | − | − | + | + |
| 11b | − | − | − | − | − | − | − | +/− | − |
| 11c | nd | nd | nd | +++ | +++ | ++++ | ++++ | +++ | ++ |
| 13 | − | − | − | − | − | − | − | +++ | − |
| 14 | − | − | − | − | − | − | − | − | − |
| 15 | − | − | − | +/− | − | − | − | − | − |
| 16 | − | − | − | − | − | +++ | − | ++ | +++ |
| 19 | +++ | +++ | +++ | +++ | +++ | ++++ | ++++ | +++ | +++ |
| 20 | +++ | +++ | +++ | +++ | +++ | +++ | ++++ | +++ | ++ |
| 21 | +++ | ++ | +++ | +++ | ++ | ++++ | ++ | +++ | +++ |
| 22 | +++ | +++ | +++ | +++ | ++ | ++++ | ++++ | +++ | + |
| 23 | +++ | +++ | +++ | +++ | ++++ | +++ | ++++ | ++ | +++ |
| 24 | nd | nd | nd | ++ | ++ | +++ | ++++ | +++ | ++ |
| 25 | ++ | ++ | − | − | +++ | +++ | +++ | +++ | + |
| 33 | − | − | − | − | − | − | − | + | − |
| 34 | − | − | − | − | − | − | − | − | − |
| 36 | − | + | − | − | − | − | +/− | +/− | − |
| 37 | +++ | +++ | +++ | +++ | ++++ | ++++ | ++++ | +++ | +++ |
| 38 | nd | nd | nd | ++ | ++ | ++++ | ++++ | + | + |
| 41 | ++ | +/− | ++ | − | − | − | ++ | − | − |
| 42a | nd | nd | nd | − | − | − | − | − | − |
| 45 | ++ | ++ | + | ++ | +++ | ++++ | ++++ | +++ | ++ |
| 45RA | nd | nd | nd | +++ | − | ++++ | +++ | +++ | + |
| 45RO | nd | nd | nd | − | +++ | ++ | +/− | + | ++ |
| 52 | nd | nd | nd | +++ | ++++ | ++++ | ++++ | +++ | +++ |
| 56 | − | − | − | − | − | − | − | − | − |
| 57 | nd | nd | nd | − | + | − | − | − | − |
| 60 | nd | nd | nd | − | +++ | − | − | − | − |
| 61 | − | − | − | − | − | − | − | − | − |
| 71 | + | − | + | ++ | +++ | +++ | ++++ | ++ | ++ |
| 79a | nd | nd | nd | + | +++ | ++ | − | ++ | − |
| 95 | ++ | +++ | +/− | − | − | +/− | +/− | + | − |
| 103 | + | − | − | + | − | − | − | − | − |

TABLE 6-continued

Binding patterns for Chronic Lymphocytic Leukaemia samples from 9 patients

CLL

| Marker | AW | YI | FS | PN | PL | DD | EH2 | KB | NH |
|---|---|---|---|---|---|---|---|---|---|
| 117 | − | − | − | − | − | − | +/− | − | − |
| 122 | nd | nd | nd | − | − | − | − | + | − |
| 154 | nd | nd | nd | − | − | − | +/− | +/− | − |
| GPA | nd | nd | nd | ++++ | − | − | − | − | − |
| HLA-DR | +++ | ++ | +++ | +++ | ++++ | ++++ | ++++ | +++ | +++ |
| KOR | nd | nd | nd | − | − | +++ | − | ++ | ++ |
| FMC7 | nd | nd | nd | ++ | ++ | +++ | +/− | +++ | + |
| anti-hIg | nd | nd | nd | +++ | ++ | − | − | ++ | − | nd not done

TABLE 7

Binding patterns for PBL, CLL, PLL, HCL, BCL and AML

| | PBL | CLL | | PLL | HCL | BCL | AML |
|---|---|---|---|---|---|---|---|
| Marker | RIC2 | KB | EH2 | AR | RD | KR | GT |
| mIgG1 | − | − | − | − | − | − | − |
| 2 | +++ | ++ | ++ | + | +/− | +/− | +++ |
| 3 | ++++ | + | + | + | − | +/− | +/− |
| 4 | ++++ | + | + | + | − | +/− | +++ |
| 5 | ++++ | +++ | ++++ | + | + | ++++ | +/− |
| 7 | +++ | + | + | − | − | +/− | +/− |
| 8 | +++ | +/− | +/− | − | − | − | − |
| 9 | ++ | − | ++++ | − | +++ | +++ | +/− |
| 10 | − | + | − | − | − | − | − |
| 11b | − | +/− | − | − | − | − | ++ |
| 11c | +++ | +++ | ++++ | ++ | ++++ | +++ | ++++ |
| 13 | − | +++ | − | − | +/− | − | + |
| 14 | − | − | − | − | − | − | + |
| 15 | − | − | − | − | − | − | + |
| 16 | − | ++ | − | − | − | − | +/− |
| 19 | + | +++ | ++++ | +++ | ++ | +++ | − |
| 20 | + | +++ | ++++ | +++ | ++ | + | +/− |
| 21 | + | +++ | ++ | ++ | − | +++ | − |
| 22 | − | +++ | ++++ | +++ | +++ | +++ | − |
| 23 | + | ++ | ++++ | ++ | +/− | ++ | − |
| 24 | + | +++ | ++++ | +++ | − | +++ | − |
| 25 | ++ | +++ | +++ | ++ | +++ | − | − |
| 33 | +++ | + | − | − | − | − | ++++ |
| 34 | − | − | − | − | +/− | − | − |
| 36 | ++++ | +/− | +/− | − | − | − | ++++ |
| 37 | + | +++ | ++++ | +++ | +++ | ++++ | ++ |
| 38 | ++++ | + | ++++ | + | +/− | +++ | +++ |
| 41 | +/− | − | ++ | + | ++ | − | − |
| 42a | + | − | − | − | − | − | − |
| 45 | ++++ | +++ | +++ | ++ | +++ | ++++ | ++ |
| 45RA | + | +++ | +++ | ++ | +++ | +++ | +++ |
| 45RO | ++++ | + | +/− | +/− | − | − | + |
| 52 | − | +++ | ++++ | +++ | +++ | ++++ | +/− |
| 56 | − | − | − | − | − | − | +/− |
| 57 | − | − | − | − | − | − | +/− |
| 60 | − | − | − | − | − | − | +/− |
| 61 | + | − | − | − | − | − | − |
| 71 | +/− | ++ | ++++ | − | + | +++ | − |
| 79a | − | ++ | − | ++ | +/− | ++ | +/− |
| 95 | ++ | + | +/− | + | +/− | + | ++ |
| 103 | − | − | − | + | +++ | + | − |
| 117 | − | − | +/− | − | − | − | − |
| 122 | +/− | + | − | + | ++ | + | − |
| 154 | − | +/− | +/− | − | ++ | − | − |
| GPA | − | − | − | ++++ | + | − | − |
| HLA-DR | + | +++ | ++++ | +++ | +++ | ++++ | +++ |
| KOR | +/− | ++ | − | − | − | − | +/− |
| FMC7 | − | +++ | +/− | +/− | + | +/− | − |
| anti-hIg | − | ++ | − | nd | − | − | − | nd not done

TABLE 8

Comparison of FACS analysis and Antibody Array Results

| CD marker | RIC PBL FACS % positive | RIC PBL Dot array | RIC PBL fr FACS % positive | RIC PBL fr Dot Array | PL CLL FACS % positive | PL CLL Dot Array | AD CLL FACS % positive | AD CLL Dot Array |
|---|---|---|---|---|---|---|---|---|
| mIgG1 | – | – | – | – | – | – | – | – |
| 2 | 78 | – | 73 | nd | 16 | +/– | 14 | – |
| 3 | 47 | +++ | 65 | +++ | 17 | +/– | 6 | – |
| 4 | 52 | +++ | 48 | +++ | – | +/– | – | – |
| 5 | 48 | +++ | 61 | +++ | 97 | +++ | 93 | +++ |
| 7 | 47 | ++ | 60 | +++ | 9 | +/– | – | – |
| 8 | 16 | + | 22 | ++ | 7 | – | – | – |
| 9 | 64 | ++ | 36 | ++ | 18 dim | + | >34 | ++ |
| 10 | – | – | – | +/– | – | – | 8 | – |
| 11b | 52 | – | 27 | – | 8 dim | – | 7 | – |
| 11c | 46 | ++ | 15 | + | 71 | +++ | 29 | ++ |
| 13 | 35 | + | 10 | + | 11 | – | – | – |
| 14 | 30 | +/– | 12 | – | 16 | – | 12 dim | – |
| 15 | 27 | – | 5 | – | – | +/– | – | – |
| 16 | 8 | – | 12 | – | – | – | – | – |
| 19 | 23 | + | 12 | + | 95 | +++ | 96 | +++ |
| 20 | 44 | + | 12 | + | 95 | +++ | 93 | +++ |
| 21 | 12 | +/– | 10 | + | 70 | ++ | 86 | ++ |
| 22 | 14 | ++ | 11 | ++ | 64 | ++ | ? | +++ |
| 23 | 11 | +/– | – | +/– | 94 | +++ | 80 | +++ |
| 24 | 15 | +/– | 16 | + | 83 | ++ | 48 | ++ |
| 25 | 5 | ++ | 20 dim | + | 11 | +++ | 85 | +++ |
| 33 | 35 | ++ | 7 | – | 7 | +/– | – | +/– |
| 34 | – | – | – | – | – | – | – | – |
| 36 | 30 | ++ | 7 | ++ | – | – | 8 | +/– |
| 37 | 40 (11 br) | + | 40 (17 br) | + | 99 | +++ | 97 | +++ |
| 38 | 45 | ++ | 22 | ++ | – | +/– | 15 | + |
| 41 | 46 | ++ | 14 | ++ | – | +/– | 11 | +/– |
| 42a | 42 | ++ | 11 | + | – | – | 6 | +/– |
| 45 | 97 | ++ | 86 | nd | 100 | ++ | 98 | ++ |
| 45RA | 29 | ++ | 42 | + | 36 | + | 74 | +++ |
| 45RO | 70 | ++ | 58 | ++ | 96 | +++ | 78 | ++ |
| 52 | 96 | +++ | 82 | nd | 100 | ++++ | 96 | nd |
| 56 | 16 | – | 19 | – | – | – | 11 | – |
| 57 | – | – | 10 | – | 11 | – | 7 | – |
| 61 | 43 | + | 12 | + | – | – | 13 dim | – |
| 71 | – | – | – | – | 81 | +++ | 29 | ++ |
| 95 | 34 | + | 49 | + | 12 dim | – | 17 dim | – |
| 103 | – | ++ | – | +/– | – | – | – | – |
| 117 | – | – | – | – | – | – | – | – |
| 122 | – | +/– | 61 (9 br) | + | 9 | +/– | – | – |
| 154 | 19 dim | – | 36 dim | – | – | – | 13 dim | – |
| GPA | – | – | – | + | – | – | 12 dim | – |
| HLA-DR | 45 | +++ | 21 | nd | 97 | ++++ | 94 | +++ |
| KOR | – | +++ | – | ++ | – | – | – | – |
| FMC7 | 13 | – | 9 | – | 52 | ++ | 28 | – | fr fresh blood
nd not done
br bright

BIBLIOGRAPHY

Bene, M. -C. and Martini, E. (1997). *Immunophenotyping of Blood and Bone Marrow Leukocytes,* Harwood Academic Publishers, Australia.

Chang, T. -W. (1983) *J. Immunol. Methods* 65, 217-223.

Cooper, G. M. (1993). *The Cancer Book,* p. 158, Jones and Bartlett Publishers.

de Matos, O. and Vale, C. E. (1996). U.S. Pat. No. 5,538,855.

Goward C R, Murphy J P, Atkinson T, Barstow D A (1990). *Biochem. J.* 267, 171-177.

Kishimoto, T et al. (1997). *Leukocyte typing VI. White cell differentiation antigens.* Proceedings of the Sixth International Workshop and Conference held in Kobe, Japan, 10-14 Nov. 1996; Garland Publishing Inc, NY, USA.

Mage, M. G., McHugh, L. L. and Rothstein, T. L. (1977). *J. Immunol. Methods* 15, 47-56.Shinton, N. K. (1998) *CRC Desk Reference for Hematology* CRC Press, Boca Raton.

van Dongen, J. J. M. et al. *Neth. J. Med.* (1988). 33: 298-314.

Wysocki, L. J. and Sato, V. L. (1978). *Proc. Natl. Acad. Sci. USA* 75, 2844-2848.

What is claimed is:

1. A method for distinguishing a leukemia of T cell, B cell, or myeloid lineage in a human subject comprising the steps of:

providing a single assay device comprising a derivatised solid support selected from the group consisting of glass, cellulose, ceramic material, nitrocellulose, polyacrylamide, nylon, polystyrene, polystyrene derivatives, polyvinylidene difluoride, methacrylate, methacrylate derivatives, polyvinyl chloride, and polypropylene, the derivatised solid support having an array of immunoglobulin molecules immobilized in discrete regions on the derivatised solid support, wherein the immunoglobulin molecules are specific for the single cell surface marker antigens of CD3, CD4, CD8, CD14, CD19, and CD56, and wherein each immunoglobulin region specific for said single surface marker is present only once in the array;

contacting a biological sample containing leukocytes with the assay device, wherein said biological sample is obtained from a human subject in need of a diagnosis of T cell, B cell, or myeloid lineage leukemia;

allowing leukocytes in the biological sample to bind to the immunoglobulin molecules on the solid support via cell surface marker antigens on the leukocytes to form a pattern of binding on an array of discrete regions each being specific for a single cell surface marker presented only once in the array; and determining the relative scale of the pattern of simultaneous binding with which the cell surface marker antigens CD3, CD4, CD8, CD14, CD19, and CD56 on the leukocytes have bound to the immunoglobulin molecules on the array, wherein the relative scale of the pattern of CD3, CD4, CD8, CD14, CD19, and CD56 binding on the array distinguishes leukemia of T cell, B cell, or myeloid lineage in the subject.

2. The method according to claim 1, wherein the solid support further contains, in addition to immunoglobulin molecules specific for the single cell surface marker antigens CD3, CD4, CD8, CD14, CD19 and CD56 of claim 1, discrete regions of immunoglobulin molecules specific for single cell surface marker antigens of a T cell, B cell, or myeloid lineage consisting of CD2, CD5, CD7, CD9, CD10, CD11b, CD11c, CD13, CD15, CD16, CD20, CD21, CD22, CD23, CD24, CD25, CD33, CD34, CD36, CD37, CD38, CD41 CD42, CD45, CD57, CD95, and CD122.

3. The method according to claim 1, wherein the solid support, in addition to immunoglobulin molecules specific for the single cell surface marker antigens CD3, CD4, CD8, CD14, CD19 and CD56 of claim 1, further contains immunoglobulins specific for antigens mIgG1, CD2, CD5, CD7, CD9, CD10, CD11b, CD11c, CD13, CD15, CD16, CD20, CD21, CD22, CD23, CD24, CD25, CD33, CD34, CD36, CD37, CD38, CD41, CD42a, CD45, CD45RA, CD45RO, CD52, CD57, CD61, CD71, CD95, CD103, CD117, CD122, CD154, GPA, HLA-DR, KOR, and FMC7.

4. The method according to claim 1, wherein the solid support, in addition to immunoglobulin molecules specific for the single cell surface marker antigens CD3, CD4, CD8, CD14, CD19 and CD56 of claim 1, further contains immunoglobulins specific for antigens mIgG1, mIgG2a, mIgG2b, mIgM, CD2, CD5, CD7, CD9, CD10, CD11b, CD11c, CD13, CD15, CD16, CD20, CD21, CD22, CD23, CD24, CD25, CD33, CD34, CD36, CD37, CD38, CD41, CD42a, CD45, CD45RA, CD45RO, CD52, CD57, CD60, CD61, CD71, CD79a, CD95, CD103, CD117, CD122, CD154, GPA, HLA-DR, KOR, FMC7, and anti-hIg.

5. The method according to claim 1, wherein the solid support, in addition to immunoglobulin molecules specific for the single cell surface marker antigens CD3, CD4, CD8, CD14, CD19 and CD56 of claim 1, further contains immunoglobulins specific for antigens mIgG1, CD2, CD5, CD7, CD9, CD10, CD11b, CD11c, CD13, CD15, CD16, CD20, CD21, CD22, CD23, CD24, CD25, CD33, CD34, CD36, CD37, CD38, CD41, CD42a, CD45, CD45RA, CD45RO, CD52, CD57, CD60, CD61, CD71, CD79a, CD95, CD103, CD117, CD122, CD154, GPA, HLA-DR, KOR, FMC7, and anti-hIg.

6. The method according to claim 1, wherein the solid support, in addition to immunoglobulin molecules specific for the single cell surface marker antigens CD3, CD4, CD8, CD14, CD19 and CD56 of claim 1, further contains immunoglobulins specific for antigens mIgG1, CD2, CD5, CD7, CD9, CD10, CD11b, CD11c, CD13, CD15, CD16, CD20, CD21, CD22, CD23, CD24, CD25, CD33, CD34, CD36, CD37, CD38, CD41, CD42a, CD44, CD44v3-10, CD44v6, CD45, CD45RA, CD45RO, CD52, CD57, CD60, CD61, CD71, CD79a, CD95, CD103, CD117, CD122, CD154, GPA, HLA-DR, KOR, FMC7, mIgG2a, mIg2b, and mIgM.

7. The method according to claim 1, wherein the solid support, in addition to immunoglobulin molecules specific for the single cell surface marker antigens CD3, CD4, CD8, CD14, CD19 and CD56 of claim 1, further contains immunoglobulins specific for antigens mIgG1, CD2, CD5, CD7, CD9, CD10, CD11b, CD11c, CD13, CD15, CD16, CD20, CD21, CD22, CD23, CD24, CD25, CD33, CD34, CD36, CD37, CD38, CD41, CD42a, CD44, CD44v3-10, CD44v6, CD45, CD45RA, CD45RO, CD52, CD57, CD60, CD61, CD64, CD71, CD79a, CD79b, CD95, CD103, CD117, CD122, CD134, CD138, CD154, Kappa, Lambda, GPA, HLA, KOR, FMC7, Anti-Ig, and IgG2a.

8. The method according to claim 1, wherein the relative scale of the pattern of simultaneous binding is detected microscopically, biochemically, histochemically or immunologically.

9. The method according to claim 8, wherein the relative scale of the pattern of simultaneous binding is detected microscopically.

10. The method according to claim 1, wherein the immunoglobulins are monoclonal antibodies.

11. The method according to claim 1, wherein the immunoglobulins are polyclonal antibodies.

12. The method according to claim 1, further comprising microscopic analysis of cellular morphology of the leukocytes.

13. The method according to claim 1, further comprising histochemical, biochemical, or immunological analysis.

14. The method according to claim 1, wherein the solid support is nitrocellulose film supported on glass.

* * * * *